(12) United States Patent
Ahmed et al.

(10) Patent No.: US 7,253,174 B2
(45) Date of Patent: Aug. 7, 2007

(54) N-HETEROCYCLIC INHIBITORS OF TNF-α EXPRESSION

(75) Inventors: Gulzar Ahmed, Yardley, PA (US); Axel Metzger, East Windsor, NJ (US); Ian Henderson, Hopewell, NJ (US); David J. Diller, Hightstown, NJ (US); Jun Wen, Dayton, NJ (US); Stephen T. Wrobleski, Whitehouse Station, NJ (US); Katerina Leftheris, Skillman, NJ (US); Chunjian Liu, Pennington, NJ (US)

(73) Assignees: Bristol-Myers Squibb Company, Princeton, NJ (US); Pharmacopeia, Inc., Cranbury, NJ (US)

( * ) Notice: Subject to any disclaimer, the term of this patent is extended or adjusted under 35 U.S.C. 154(b) by 0 days.

(21) Appl. No.: 11/485,075

(22) Filed: Jul. 12, 2006

(65) Prior Publication Data

US 2006/0276488 A1 Dec. 7, 2006

Related U.S. Application Data

(63) Continuation of application No. 10/183,179, filed on Jun. 26, 2002, now abandoned.

(60) Provisional application No. 60/301,020, filed on Jun. 26, 2001.

(51) Int. Cl.
*C07D 239/48* (2006.01)
*A61K 31/505* (2006.01)

(52) U.S. Cl. .............. 514/256; 514/275; 544/323; 544/324; 544/326; 544/328; 544/329

(58) Field of Classification Search ............... 544/323, 544/324, 326, 328, 329; 514/256, 275
See application file for complete search history.

(56) References Cited

U.S. PATENT DOCUMENTS

| | | | |
|---|---|---|---|
| 5,428,044 | A | 6/1995 | Bantick et al. |
| 6,107,301 | A | 8/2000 | Aldrich et al. |
| 6,342,503 | B1 | 1/2002 | Aldrich et al. |

FOREIGN PATENT DOCUMENTS

| | | |
|---|---|---|
| WO | WO01/19825 | 3/2001 |
| WO | WO01/27089 | 4/2001 |
| WO | WO01/28561 | 4/2001 |
| WO | WO01/47897 | 7/2001 |
| WO | WO 01/72717 | * 10/2001 |
| WO | WO03/002542 | 1/2003 |
| WO | WO03/032994 | 4/2003 |
| WO | WO03/032997 | 4/2003 |
| WO | WO03/063794 | 8/2003 |

OTHER PUBLICATIONS

Ulrich, Chapter 4: Crystallization, Kirk-Othmer Encyclopedia of Chemical Technology, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Database Caplus, Accession No. 104:168491, JP61-10563 B (Ito et al.) Jan. 18, 1986 see CAS abstract.
Wissner et al., J. Med. Chem. 2000, 43, pp. 3244-3256.
Chen et al., Biochemistry 1998, 37, p. 17735-17744.

* cited by examiner

*Primary Examiner*—Deepak Rao
(74) *Attorney, Agent, or Firm*—Maureen P. O'Brien; Joseph C. Wang

(57) ABSTRACT

N-heterocyclic compounds that block cytokine production via inhibition of p38 kinase are disclosed. In one embodiment, compounds of the present invention are represented by Formula (I):

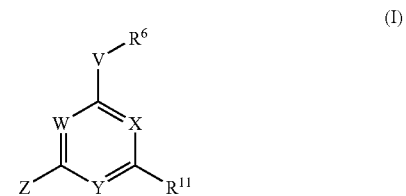

Methods of production, pharmaceutical compositions and methods of treating conditions associated with inappropriate p38 kinase activity or TNF-α expression utilizing compounds of the present invention are also disclosed.

8 Claims, No Drawings

N-HETEROCYCLIC INHIBITORS OF TNF-α EXPRESSION

CROSS-REFERENCE TO RELATED APPLICATIONS

This application is a continuation of Ser. No. 10/183,179, filed Jun. 26, 2002, now abandoned, which claims priority to provisional Application Ser. No. 60/301,020, filed Jun. 26, 2001, both of which are incorporated herein by reference in their entirety.

FIELD OF THE INVENTION

This invention relates to N-heterocyclic compounds that are effective in blocking cytokine production, and in particular the expression of TNF-alpha (TNF-α), via inhibition of p38 kinase. Compounds of the present invention are useful in the treatment of inflammatory diseases such as, for example, rheumatoid arthritis.

BACKGROUND OF THE INVENTION

Overproduction of cytokines such as IL-1 and TNF-α is implicated in a wide variety of inflammatory diseases, including rheumatoid arthritis (RA), psoriasis, multiple sclerosis, inflammatory bowel disease, endotoxin shock, osteoporosis, Alzheimer's disease and congestive heart failure, among others [Henry et al., *Drugs Fut.*, 24:1345-1354 (1999); Salituro et al., *Curr. Med. Chem.*, 6:807-823 (1999)]. There is convincing evidence in human patients that protein antagonists of cytokines, such as, for example, monoclonal antibody to TNF-α (Enbrel) [Rankin et al., *Br. J. Rheumatol.*, 34:334-342 (1995)], soluble TNF-α receptor-Fc fusion protein (Etanercept) [Moreland et al., *Ann. Intern. Med.*, 130:478-486 (1999)] and or IL-1 receptor antagonist [Bresnihan et al., *Arthritis Rheum.*, 41:2196-2204 (1998)], can provide effective treatment for chronic inflammatory diseases. As none of the current treatments for inflammatory diseases provide complete relief of symptoms, and as most current treatments are associated with various drawbacks such as side effects, improved methods for treating inflammatory diseases are desirable.

TNF-α is a protein whose synthesis occurs in many cell types in response to an external stimulus, such as, for example, a mitogen, an infectious organism, or trauma. Signaling from the cell surface to the nucleus proceeds via several intracellular mediators including kinases that catalyze phosphorylation of proteins downstream in the signaling cascade. Important mediators for the production of TNF-α cytokine are the mitogen-activated protein (MAP) kinases, and in particular, p38 kinase.

p38 Kinases are activated in response to various stress stimuli, including, but not limited to, proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif, characteristic of p38 isozymes.

Four iso-forms of p38 have been described. The α and β forms are expressed in inflammatory cells and are thought to be key mediators of TNF-α production. Inhibition of the enzymes p38α and β in cells results in reduced levels of expression of TNF-α, and such inhibitors are effective in animal models of inflammatory disease.

Molecular cloning of human p38α identified two isozymes, which are the splice variant product of a single gene. Three additional gene products have subsequently been identified, p38β, p38γ, and p38δ. p38 kinases phosphorylate and activate the transcription factors, ATF-2, MAX, CHOP, and C/ERPb, suggesting a role of p38 kinases in gene regulation. In addition, p38 kinases phosphorylate other protein kinases, such as MAPK activated protein kinase-2/3 (MAPKAP-K2/3, or MK2/3), and MAP-kinase-interacting kinase 1/2 (MNK1/2). Recently, activation of MK2 has been shown to be essential for LPS-induced TNF-α expression [Kotlyarov et al., *Nature Cell Biol.*, 1:94-97 (1999)]. Mice lacking MK2 exhibit a 90% reduction in the production of TNF-α and are resistant to shock induced by LPS. The reduction in TNF-α amounts is due not to decreased production of the TNF-α mRNA, but rather to diminished production of the TNF-α protein, suggesting that MK2 regulates biosynthesis of TNF-α at a post-transcriptional level.

Ample evidence indicates that the p38 pathway serves an important role in inflammatory process mediated by IL-1 and TNF-α.

Small molecule inhibitors of p38 are expected to have several advantages over protein inhibitors of TNF-α or IL-1. p38 inhibitors not only block the production of TNF-α and IL-1, but also directly interfere with many of their secondary biological effects. In addition, small molecule inhibitors are unlikely to induce immune reaction in patients, and are believed active following oral administration.

The present invention provides novel compounds that are potent and selective inhibitors of p38α and β, and as such, are also potent inhibitors of TNF-α expression in human cells. Compounds of the present invention are useful in the treatment of p38- and TNF-α expression-mediated inflammatory and other disorders, including, but not limited to, bone resorption, graft vs. host reaction, atherosclerosis, arthritis, osteoarthritis, rheumatoid arthritis, gout, psoriasis, topical inflammatory disease states, adult respiratory distress syndrome, asthma, chronic pulmonary inflammatory disease, cardiac reperfusion injury, renal reperfusion injury, thrombus, glomerulonephritis, Chron's disease, ulcerative colitis, inflammatory bowel disease, multiple sclerosis, endotoxin shock, osteoporosis, Alzheimer's disease, congestive heart failure and cachexia.

SUMMARY OF THE INVENTION

The compounds of the present invention are effective as inhibitors of inappropriate p38 activity, especially iso forms α and β, and in turn, of cytokine production, and in particular, of cellular TNF-alpha (TNF-α) expression. Accordingly, compounds of the invention are useful for the inhibition, prevention and suppression of various pathologies associated with such activity, such as, for example, inflammation, asthma, arthritis, atherosclerosis, multiple sclerosis, psoriasis, autoimmune diseases, Alzeheimers disease and congestive heart failure, among others.

In one embodiment, the principles of the present invention provide a compound, including isomers, enantiomers, diastereomers, tautomers, pharmaceutically acceptable salts, prodrugs and solvates thereof, represented by Formula (I):

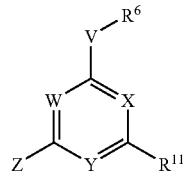

wherein:
one or two of W, Y and X are =N—;
one of W, Y and X is selected from =C—CN, =C—F, =C—NO$_2$, =C—Br, =C—NH$_2$, =C—NHC(O)CH$_3$ and =C—Cl;
the remaining W, Y or X is =CH—;
V is —NR$^5$—;
Z is halogen or —N(R$^1$)(R$^2$);
R$^1$ and R$^2$ are the same or different and are selected from hydrogen, alkyl, substituted alkyl, aryl, substituted aryl, cycloalkyl, substituted cycloalkyl, heterocyclyl or substituted heterocyclyl;
R$^5$ is hydrogen or alkyl;
R$^6$ is

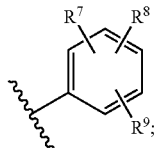

R$^7$ is hydrogen, alkyl, substituted alkyl, alkoxy, or halogen;
R$^8$ is hydrogen, alkyl, alkyloxy or cyano;
R$^9$ is —C(O)R$^{10}$ or unsubstituted or substituted heterocyclyl;
R$^{10}$ is —N(R$^{31}$)(R$^{32}$);
R$^{31}$ and R$^{32}$ are the same or different and are selected from hydrogen, alkyl, substituted alkyl, alkoxy, aryl, substituted aryl, cycloalkyl, substituted cycloalkyl, heterocyclyl or substituted heterocyclyl;
R$^{11}$ is hydrogen, halogen, O—R$^{35}$ or —N(R$^{12}$)(R$^{13}$);
R$^{12}$ is hydrogen, alkyl, or substituted alkyl;
R$^{13}$ is —(CH$_2$)$_m$R$^{14}$;
—N(R$^{12}$)(R$^{13}$) taken together may form a heterocyclyl or substituted heterocyclyl;
m is 0, 1, 2 or 3;
R$^{14}$ is hydrogen, alkyl, substituted alkyl, —C(O)N(R$^{31}$)(R$^{32}$), —N(R$^{33}$)C(O)R$^{34}$, aryl, substituted aryl, cycloalkyl, substituted cycloalkyl, heterocyclyl, substituted heterocyclyl, heteroaryl, substituted heteroaryl or

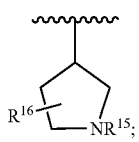

R$^{15}$ is hydrogen, alkyl or substituted alkyl;
R$^{16}$ is hydrogen or alkyl; or R$^{33}$ is hydrogen, alkyl, or substituted alkyl;
R$^{34}$ is alkyl, substituted alkyl, aryl or substituted aryl;

R$^{35}$ is hydrogen or -(lower alkyl)-R$^{36}$;
R$^{36}$ is N(R$^{37}$)(R$^{38}$);
R$^{37}$ is hydrogen, alkyl, or substituted alkyl;
R$^{38}$ is -(substituted alkyl)-R$^{14}$; and
N(R$^{37}$)(R$^{38}$) taken together may form a heterocyclyl or substituted heterocyclyl.

Preferred compounds of this invention are those of Formula (I) including a pharmaceutically acceptable salt thereof wherein:
one or two of W, Y and X are =N—;
one of W, Y and X is selected from =C—CN, =C—F, =C—NO$_2$, =C—Br, =C—NH$_2$, =C—NHC(O)CH$_3$ and =C—Cl;
the remaining W, Y or X is =CH—;
V is —NH—;
Z is —N(R$^1$)(R$^2$);
R$^1$ and R$^2$ are the same or different and are selected from hydrogen, alkyl or substituted alkyl wherein alkyl is of 1 to 8 carbons;
R$^6$ is

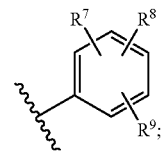

R$^7$ is hydrogen, alkyl of 1 to 4 carbons, alkoxy of 1 to 4 carbons, or halogen;
R$^8$ is hydrogen;
R$^9$ is —C(O)R$^{10}$ or unsubstituted or substituted heterocyclyl;
R$^{10}$ is —NH$_2$ or unsubstituted or substituted —NH-alkyl, —NH-alkoxy, —NH-heterocyclyl, —NH-phenyl, or —NH—CH$_2$-phenyl wherein alkyl and alkoxy are of 1 to 6 carbons;
R$^{11}$ is hydrogen, halogen, O—R$^{35}$ or —N(R$^{12}$)(R$^{13}$), wherein N(R$^{12}$)(R$^{13}$) taken together may form a monocyclic heterocyclyl or substituted heterocyclyl of 5 to 7 atoms containing 1, 2, or 3 additional nitrogen atoms or wherein
R$^{12}$ is hydrogen;
R$^{13}$ is alkyl of 1 to 4 carbons or

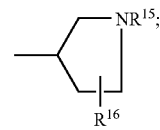

R$^{15}$ and R$^{16}$ are independently selected from hydrogen and methyl;
R$^{35}$ is hydrogen or -(lower alkyl)-R$^{36}$;
R$^{36}$ is N(R$^{37}$)(R$^{38}$);
R$^{37}$ is hydrogen, alkyl, or substituted alkyl;
R$^{38}$ is -(substituted alkyl)-R$^{14}$; and
N(R$^{37}$)(R$^{38}$) taken together may form a heterocyclyl or substituted heterocyclyl.

The principles of the present invention also provide methods of inhibiting TNF-α expression in a mammal, wherein the methods comprise administering to the mammal an effective amount of a compound represented by Formula (I), or a prodrug or salt thereof. As used herein, inhibiting TNF-α expression is intended to include inhibiting, suppressing and preventing conditions associated with inappropriate TNF-α expression, including, but not limited to, inflammation, asthma, arthritis, atherosclerosis, multiple sclerosis, psoriasis, autoimmune diseases, Alzheimer's disease and congestive heart failure.

The principles of the present invention further provide methods of treating p38 kinase and TNF-α mediated disorders in a mammal, the methods comprising administering to a mammal in need of such treatment, an effective amount of a compound represented by Formula (I), or a prodrug or salt thereof. As used herein, a p38 kinase mediated disorder means a disorder associated with inappropriate p38 kinase activity; a TNF-α mediated disorder means a disorder associated with inappropriate TNF-α expression. Such disorders include, but are not limited to, inflammation, asthma, arthritis, atherosclerosis, multiple sclerosis, psoriasis, autoimmune diseases, Alzheimer□s disease and congestive heart failure.

Accordingly, the compounds of the invention, as well as prodrugs or salts thereof, may be used in the manufacture of a pharmaceutical composition or medicament for the prophylactic or therapeutic treatment of disease states in mammals. The compounds of the present invention may be administered as pharmaceutical compositions as a monotherapy, or in combination with, for example, other anti-inflammatory, e.g. a steroid or NSAID (non-steroidal anti-inflammatory drug) and/or immunosuppressive agents. Such combination therapies can involve the administration of the various pharmaceuticals as a single dosage form or as multiple dosage forms administered simultaneously or sequentially.

Any suitable route of administration may be employed for providing a patient with an effective amount of a compound of the present invention. Suitable routes of administration may include, for example, oral, rectal, nasal, buccal, parenteral (such as, intravenous, intrathecal, subcutaneous, intramuscular, intrasternal, intrahepatic, intralesional, intracranial, intra-articular, and intra-synovial), transdermal (such as, for example, patches), and the like. Due to their ease of administration, oral dosage forms, such as, for example, tablets, troches, dispersions, suspensions, solutions, capsules, soft gelatin capsules, and the like, may be preferred. Administration may also be by controlled or sustained release means and delivery devices. Methods for the preparation of such dosage forms are well known in the art.

Pharmaceutical compositions incorporating compounds of the present invention may include excipients, a pharmaceutically acceptable carrier, in addition to other therapeutic ingredients. Excipients such as starches, sugars, microcrystalline cellulose, diluents, lubricants, binders, coloring agents, flavoring agents, granulating agents, disintegrating agents, and the like may be appropriate depending upon the route of administration. Because of their ease of administration, tablets and capsules represent the most advantageous oral dosage unit forms. If desired, tablets may be coated by standard aqueous or nonaqueous techniques.

The compounds of the present invention may be used in the form of pharmaceutically acceptable salts derived from inorganic or organic bases, and hydrates thereof. Included among such base salts are ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

DETAILED DESCRIPTION OF THE INVENTION

[1] Thus, in a first embodiment, the present invention provides a novel compound of Formula (I) including isomers, enantiomers, diastereomers, tautomers, pharmaceutically acceptable salts, prodrugs and solvates thereof, comprising:

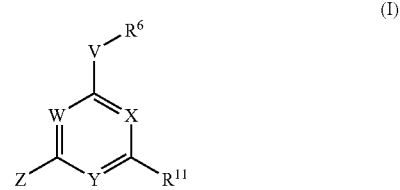

wherein:

one or two of W, Y and X are =N—;

one of W, Y and X is selected from =C—CN, =C—F, =C—NO$_2$, =C—Br, =C—NH$_2$, =C—NHC(O)CH$_3$ and =C—Cl;

the remaining W, Y or X is =CH—;

V is —NR$^5$—;

Z is halogen or —N(R$^1$)(R$^2$);

R$^1$ and R$^2$ are the same or different and are selected from hydrogen, alkyl, substituted alkyl, aryl, substituted aryl, cycloalkyl, substituted cycloalkyl, heterocyclyl or substituted heterocyclyl;

R$^5$ is hydrogen or alkyl;

R$^6$ is

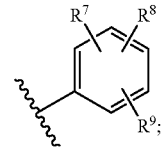

R$^7$ is hydrogen, alkyl, substituted alkyl, alkoxy, or halogen;

R$^8$ is hydrogen, alkyl, alkyloxy or cyano;

R$^9$ is —C(O)R$^{10}$ or unsubstituted or substituted heterocyclyl;

R$^{10}$ is —N(R$^{31}$)(R$^{32}$);

R$^{31}$ and R$^{32}$ are the same or different and are selected from hydrogen, alkyl, substituted alkyl, alkoxy, aryl, substituted aryl, cycloalkyl, substituted cycloalkyl, heterocyclyl or substituted heterocyclyl;

R$^{11}$ is hydrogen, halogen, O—R$^{35}$ or —N(R$^{12}$)(R$^{13}$);

R$^{12}$ is hydrogen, alkyl, or substituted alkyl;

R$^{13}$ is —(CH$_2$)$_m$R$^{14}$;

—N(R$^{12}$)(R$^{13}$) taken together may form a heterocyclyl or substituted heterocyclyl;

m is 0, 1, 2 or 3;

R$^{14}$ is hydrogen, alkyl, substituted alkyl, —C(O)N(R$^{31}$)(R$^{32}$), —N(R$^{33}$)C(O)R$^{34}$, aryl, substituted aryl, cycloalkyl, substituted cycloalkyl, heterocyclyl, substituted heterocyclyl, heteroaryl, substituted heteroaryl or

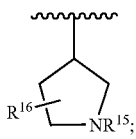

$R^{15}$ is hydrogen, alkyl or substituted alkyl;
$R^{16}$ is hydrogen or alkyl; or
$R^{33}$ is hydrogen, alkyl, or substituted alkyl;
$R^{34}$ is alkyl, substituted alkyl, aryl or substituted aryl;
$R^{35}$ is hydrogen or -(lower alkyl)-$R^{36}$;
$R^{36}$ is $N(R^{37})(R^{38})$;
$R^{37}$ is hydrogen, alkyl, or substituted alkyl;
$R^{38}$ is -(substituted alkyl)-$R^{14}$; and
$N(R^{37})(R^{38})$ taken together may form a heterocyclyl or substituted heterocyclyl.

[2] In a preferred embodiment, the present invention provides a compound of Formula (I) including isomers, enantiomers, diastereomers, tautomers, pharmaceutically acceptable salts, prodrugs and solvates thereof,
wherein:
one or two of W, Y and X are =N—;
one of W, Y and X is selected from =C—CN, =C—F, =C—NO$_2$, =C—Br, =C—NH$_2$, =C—NHC(O)CH$_3$ and =C—Cl;
the remaining W, Y or X is =CH—;
V is —NH—;
Z is —N(R$^1$)(R$^2$);
$R^1$ and $R^2$ are the same or different and are selected from hydrogen, alkyl or substituted alkyl wherein alkyl is of 1 to 8 carbons;
$R^6$ is

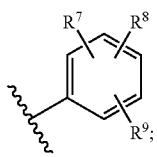

$R^7$ is hydrogen, alkyl of 1 to 4 carbons, alkoxy of 1 to 4 carbons, or halogen;
$R^8$ is hydrogen;
$R^9$ is —C(O)R$^{10}$ or unsubstituted or substituted heterocyclyl;
$R^{10}$ is —NH$_2$ or unsubstituted or substituted —NH-alkyl, —NH-alkoxy, —NH-heterocyclyl, —NH-phenyl, or —NH—CH$_2$-phenyl wherein alkyl and alkoxy are of 1 to 6 carbons;
$R^{11}$ is hydrogen, halogen, O—R$^{35}$ or —N(R$^{12}$)(R$^{13}$), wherein N(R$^{12}$)(R$^{13}$) taken together may form a monocyclic heterocyclyl or substituted heterocyclyl of 5 to 7 atoms containing 1, 2, or 3 additional nitrogen atoms or wherein $R^{12}$ is hydrogen;
$R^{13}$ is alkyl of 1 to 4 carbons or

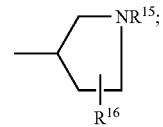

$R^{15}$ and $R^{16}$ are independently selected from hydrogen and methyl;
$R^{35}$ is hydrogen or -(lower alkyl)-$R^{36}$;
$R^{36}$ is $N(R^{37})(R^{38})$;
$R^{37}$ is hydrogen, alkyl, or substituted alkyl;
$R^{38}$ is -(substituted alkyl)-$R^{14}$; and
$N(R^{37})(R^{38})$ taken together may form a heterocyclyl or substituted heterocyclyl.

[3] In a more preferred embodiment, the present invention provides a compound of Formula (I) including isomers, enantiomers, diastereomers, tautomers, pharmaceutically acceptable salts, prodrugs and solvates thereof,
wherein:
one or two of W, Y and X are =N—;
one of W, Y and X is selected from =C—CN, =C—F, =C—NO$_2$, =C—Br, =C—NH$_2$, =C—NHC(O)CH$_3$ and =C—Cl;
the remaining W, Y or X is =CH—;
V is —NH—;
Z is —N(R$^1$)(R$^2$);
$R^1$ and $R^2$ are the same or different and are selected from hydrogen or alkyl of 1 to 8 carbons;
$R^6$ is

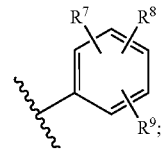

$R^7$ is hydrogen, methyl, methoxy, Cl, Br, or F;
$R^8$ is hydrogen;
$R^9$ is —C(O)R$^{10}$ or unsubstituted or substituted heterocyclyl;
$R^{10}$ is —NH$_2$, or unsubstituted or substituted —NH-alkyl, —NH-alkoxy, —NH-phenyl, or —NH—CH$_2$-phenyl wherein alkyl and alkoxy are of 1 to 6 carbons; and
$R^{11}$ is hydrogen, halogen, O—R$^{35}$ or —N(R$^{12}$)(R$^{13}$) wherein N(R$^{12}$)(R$^{13}$) taken together form a monocyclic heterocyclyl or substituted heterocyclyl of 5 to 7 atoms containing 1, 2, or 3 additional nitrogen atoms.

[4] In another preferred embodiment, the present invention provides a compound of Formula (I) including isomers, enantiomers, diastereomers, tautomers, pharmaceutically acceptable salts, prodrugs and solvates thereof,
wherein:
one of W, Y and X is =N—;
one of W, Y and X is selected from =C—CN, =C—F, =C—NO$_2$, =C—Br, =C—NH$_2$, =C—NHC(O)CH$_3$ and =C—Cl;
the remaining W, Y or X is =CH—;
V is —NH—;
Z is —N(R$^1$)(R$^2$);

$R^1$ and $R^2$ are the same or different and are selected from hydrogen or alkyl of 1 to 8 carbons;

$R^6$ is

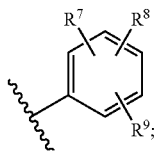

$R^7$ is hydrogen, methyl, methoxy, Cl, Br, or F;
$R^8$ is hydrogen;
$R^9$ is —C(O)$R^{10}$ or unsubstituted or substituted heterocyclyl;
$R^{10}$ is —$NH_2$, or unsubstituted or substituted —NH-alkyl, —NH-alkoxy, —NH-phenyl, or —NH—$CH_2$-phenyl wherein alkyl and alkoxy are of 1 to 6 carbons;
$R^{11}$ is hydrogen, halogen, —O—$R^{35}$ or —N($R^{12}$)($R^{13}$) wherein N($R^{12}$)($R^{13}$) taken together form a monocyclic heterocyclyl or substituted heterocyclyl of 5 to 7 atoms containing 1, 2, or 3 additional nitrogen atoms; and
$R^{15}$ and $R^{16}$ are independently selected from hydrogen and methyl.

[5] In another more preferred embodiment, the present invention provides a compound of Formula (I) including isomers, enantiomers, diastereomers, tautomers, pharmaceutically acceptable salts, prodrugs and solvates thereof, wherein:
$R^{10}$ is —$NH_2$, unsubstituted or substituted —NH—$CH_3$, —NH—$C_2H_5$, —NH—$OCH_3$, or —NH—$OC_2H_5$.

[6] In another more preferred embodiment, the present invention provides a compound of Formula (I) including isomers, enantiomers, diastereomers, tautomers, pharmaceutically acceptable salts, prodrugs and solvates thereof, wherein:
$R^9$ is unsubstituted or substituted triazole, thiazole, oxadiazole or imidazole.

[7] In another more preferred embodiment, the present invention provides a compound of Formula (I) including isomers, enantiomers, diastereomers, tautomers, pharmaceutically acceptable salts, prodrugs and solvates thereof, wherein:
$R^{11}$ is hydrogen, halogen, —O-(substituted alkyl), —NH— (substituted alkyl) or

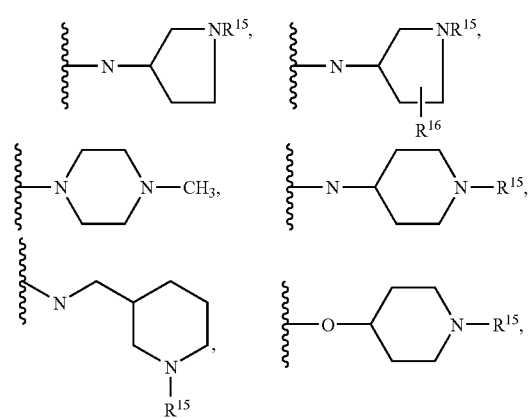

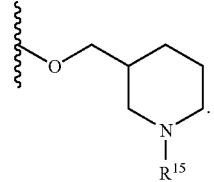

[8] In yet another preferred embodiment, the present invention provides a compound of Formula (I) including isomers, enantiomers, diastereomers, tautomers, pharmaceutically acceptable salts, prodrugs and solvates thereof, wherein:
$R^{11}$ is hydrogen, halogen, —O-(substituted alkyl), —NH-(substituted alkyl) or

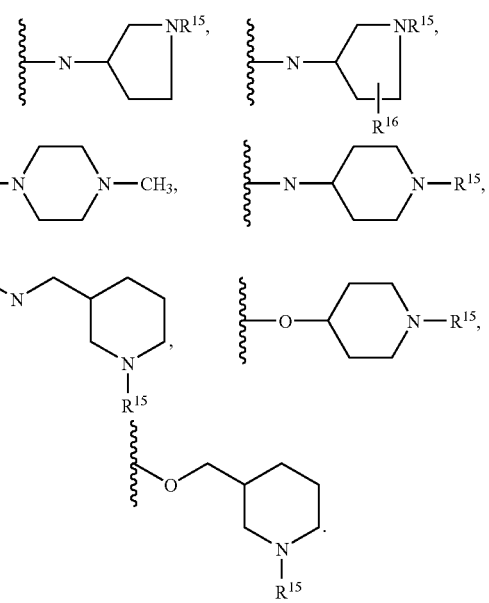

In yet another preferred embodiment, the present invention provides a compound of Formula (I) including isomers, enantiomers, diastereomers, tautomers, pharmaceutically acceptable salts, prodrugs and solvates thereof, wherein:
two of W, Y and X are =N—;
the remaining W, Y or X is selected from =C—CN, =C—F, =C—$NO_2$, =C—Br, =C—$NH_2$, =C—NHC(O)$CH_3$ and =C—Cl;
V is —NH—;
Z is —N($R^1$)($R^2$);
$R^1$ and $R^2$ are the same or different and are selected from hydrogen or alkyl of 1 to 8 carbons;
$R^6$ is

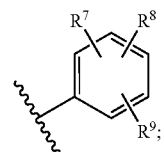

R[7] is hydrogen, methyl, methoxy, Cl, Br, or F;
R[8] is hydrogen;
R[9] is —C(O)R[10] or unsubstituted or substituted heterocyclyl;
R[10] is —NH$_2$, or unsubstituted or substituted —NH-alkyl, —NH-alkoxy, —NH-phenyl, or —NH—CH$_2$-phenyl wherein alkyl and alkoxy are of 1 to 6 carbons;
R[11] is hydrogen, halogen, —O—R[35] or —N(R[12])(R[13]), wherein N(R[12])(R[13]) taken together may form a monocyclic heterocyclyl or substituted heterocyclyl of 5 to 7 atoms containing 1, 2, or 3 additional nitrogen atoms; and
R[15] and R[16] are independently selected from hydrogen and methyl.

[10] In yet another more preferred embodiment, the present invention provides a compound of Formula (I) including isomers, enantiomers, diastereomers, tautomers, pharmaceutically acceptable salts, prodrugs and solvates thereof, wherein:
R[10] is —NH$_2$, unsubstituted or substituted —NH—CH$_3$, —NH—C$_2$H$_5$, —NH—OCH$_3$, or —NH—OC$_2$H$_5$.

[11] In yet another more preferred embodiment, the present invention provides a compound of Formula (I) including isomers, enantiomers, diastereomers, tautomers, pharmaceutically acceptable salts, prodrugs and solvates thereof, wherein:
R[9] is unsubstituted or substituted triazole, thiazole, oxadiazole or imidazole.

[12] In yet another more preferred embodiment, the present invention provides a compound of Formula (I) including isomers, enantiomers, diastereomers, tautomers, pharmaceutically acceptable salts, prodrugs and solvates thereof, wherein:
R[11] is hydrogen, halogen, —O-(substituted alkyl), —NH-(substituted alkyl) or

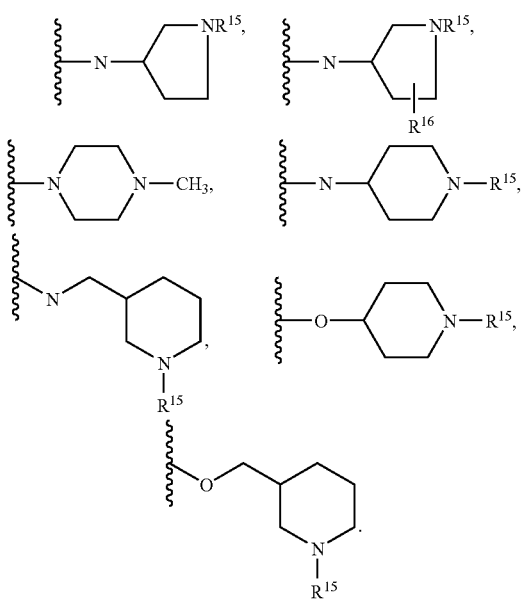

[13] In yet another more preferred embodiment, the present invention provides a compound of Formula (I) including isomers, enantiomers, diastereomers, tautomers, pharmaceutically acceptable salts, prodrugs and solvates thereof, wherein:
R[11] is hydrogen, halogen, —O-(substituted alkyl), —NH-(substituted alkyl) or

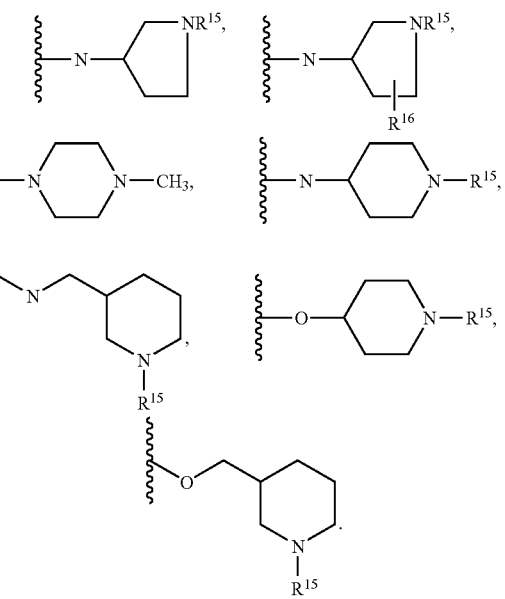

[14] In a second preferred embodiment, the present invention provides a pharmaceutical composition comprising as an active ingredient, a compound of the invention or a prodrug or salt thereof, and a pharmaceutically acceptable carrier.

[15] In a preferred embodiment, the present invention provides a pharmaceutical composition further comprising one or more additional active ingredients.

[16] In a more preferred embodiment, the present invention provides a pharmaceutical composition wherein the additional active ingredient is an anti-inflammatory compound or an immunosuppressive agent.

[17] In a more preferred embodiment, the present invention provides a pharmaceutical composition wherein the additional active ingredient is chosen from a steroid and an NSAID.

[18] In a third embodiment, the present invention provides a method of inhibiting TNF-α expression in a mammal comprising administering to the mammal an effective amount of the pharmaceutical composition of the invention.

[19] In a preferred embodiment, the present invention provides a method of treating TNF-α mediated disorder comprising administering to a mammal in need of such treatment, an effective amount of a pharmaceutical composition of the invention.

[20] In a more preferred embodiment, the present invention provides a method of treating TNF-α mediated disorder, wherein the TNF-α mediated disorder is an inflammatory disorder.

[21] In a more preferred embodiment, the present invention provides a method of treating TNF-α mediated disorder, wherein the TNF-α mediated disorder is chosen from bone resorption, graft vs. host reaction, atherosclerosis, arthritis, osteoarthritis, rheumatoid arthritis, gout, psoriasis, topical inflammatory disease states, adult respiratory distress syndrome, asthma, chronic pulmonary inflammatory disease, cardiac reperfusion injury, renal reperfusion injury, thrombus, glomerulonephritis, Chron's disease, ulcerative colitis, inflammatory bowel disease, multiple sclerosis, endotoxin shock, osteoporosis, Alzheimer's disease, congestive heart failure and cachexia.

[22] In a more preferred embodiment, the present invention provides a method of treating TNF-α mediated disorder wherein the pharmaceutical composition of the invention is administered with one or more additional anti-inflammatory or immunosuppressive agents as a single dose form or as separate dosage forms.

[23] In an even more preferred embodiment, the present invention provides a method of treating a condition associated with TNF-α expression in a mammal comprising administering to a mammal in need of such treatment, an effective amount of a pharmaceutical composition of the invention.

[24] In an even more preferred embodiment, the present invention provides a method of treating a condition associated with TNF-α expression in a mammal wherein the condition associated with TNF-α expression is an inflammatory disorder.

[25] In a more preferred embodiment, the present invention provides a method of treating a condition associated with TNF-α expression, wherein the condition associated with TNF-α expression is chosen from bone resorption, graft vs. host reaction, atherosclerosis, arthritis, osteoarthritis, rheumatoid arthritis, gout, psoriasis, topical inflammatory disease states, adult respiratory distress syndrome, asthma, chronic pulmonary inflammatory disease, cardiac reperfusion injury, renal reperfusion injury, thrombus, glomerulonephritis, Crohn's disease, ulcerative colitis, inflammatory bowel disease, multiple sclerosis, endotoxin shock, osteoporosis, Alzheimer's disease, congestive heart failure and cachexia.

[26] In a more preferred embodiment, the present invention provides a method of treating a condition associated with TNF-α expression wherein the pharmaceutical composition of the invention is administered with one or more additional anti-inflammatory or immunosuppressive agents as a single dose form or as separate dosage forms.

[27] In another more preferred embodiment, the present invention provides a method of treating a condition associated with p38 kinase activity in a mammal comprising administering to a mammal in need of such treatment, an effective amount of a pharmaceutical composition of the invention.

[28] In another more preferred embodiment, the present invention provides a method of treating a condition associated with p38 kinase activity in a mammal wherein the condition associated with p38 activity is an inflammatory disorder.

[29] In a more preferred embodiment, the present invention provides a method of treating a condition associated with p38 kinase activity is chosen from bone resorption, graft vs. host reaction, atherosclerosis, arthritis, osteoarthritis, rheumatoid arthritis, gout, psoriasis, topical inflammatory disease states, adult respiratory distress syndrome, asthma, chronic pulmonary inflammatory disease, cardiac reperfusion injury, renal reperfusion injury, thrombus, glomerulonephritis, Chron's disease, ulcerative colitis, inflammatory bowel disease, multiple sclerosis, endotoxin shock, osteoporosis, Alzheimer's disease, congestive heart failure and cachexia.

[30] In a more preferred embodiment, the present invention provides a method of treating a condition associated with p38 activity wherein the pharmaceutical composition of the invention is administered with one or more additional anti-inflammatory or immunosuppressive agents as a single dose form or as separate dosage forms.

[31] In a fourth embodiment, the present invention provides a compound including isomers, enantiomers, diastereomers, tautomers, pharmaceutically acceptable salts, prodrugs and solvates selected from:

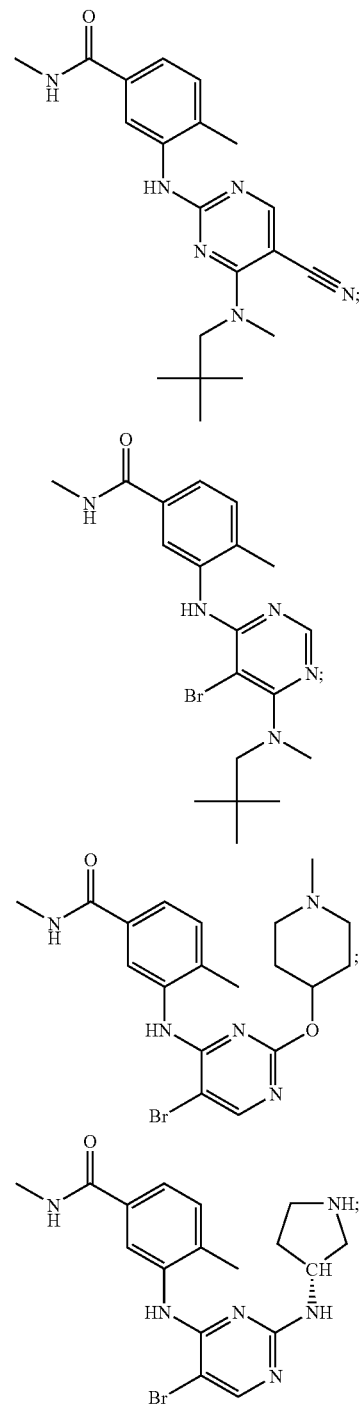

-continued
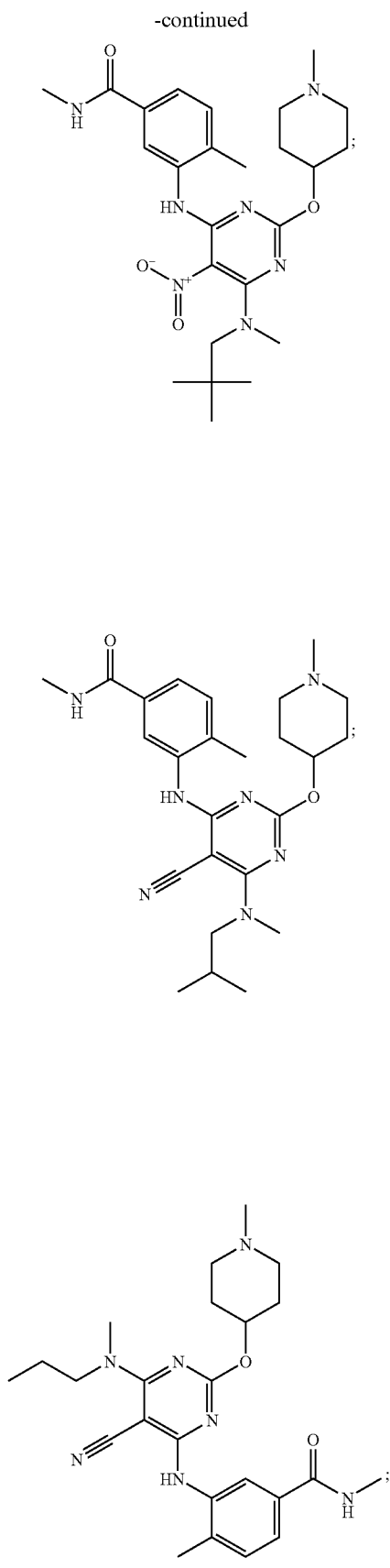
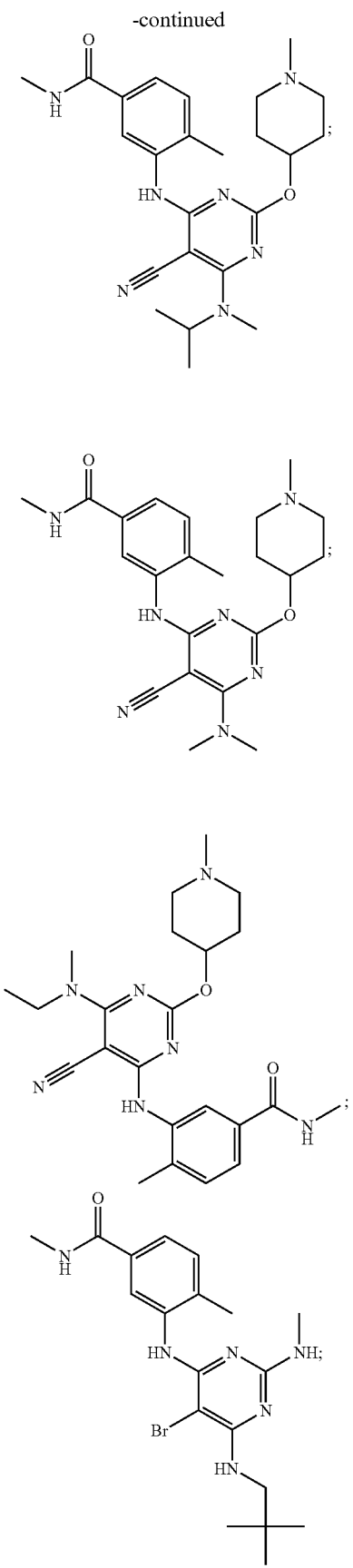

-continued
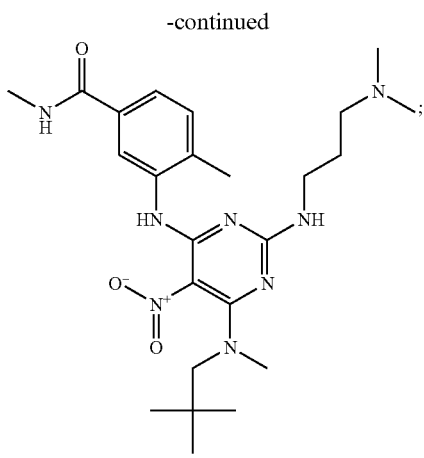
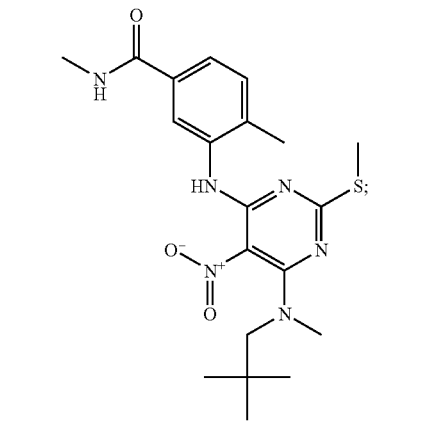
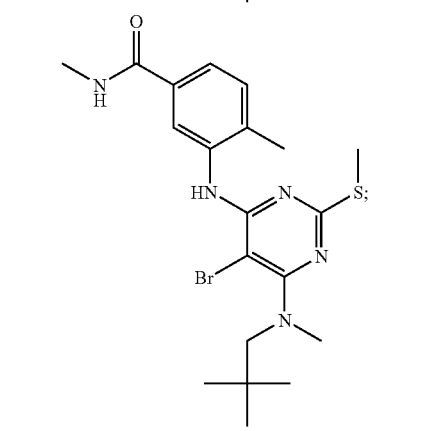
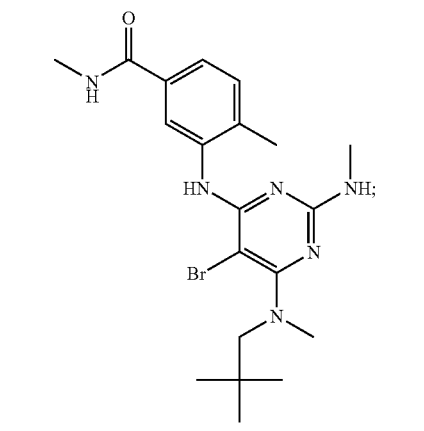
-continued
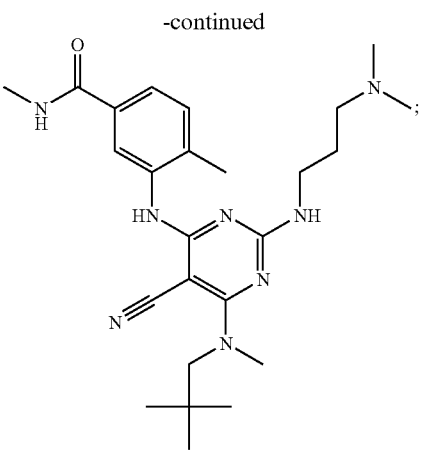
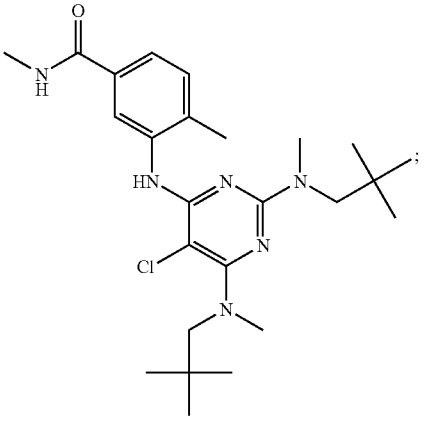
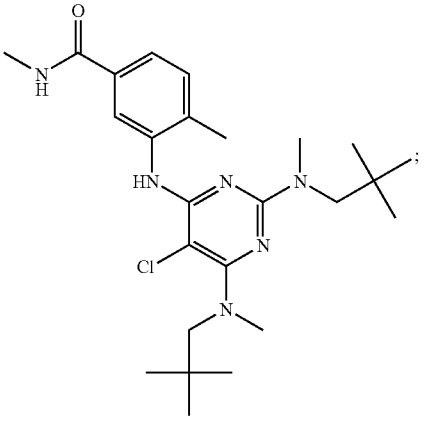

-continued
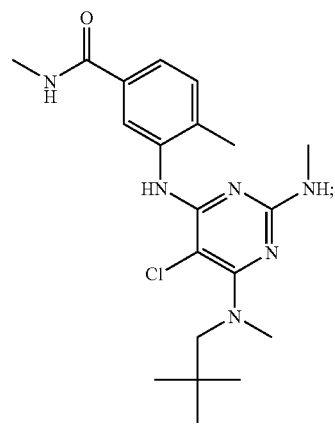
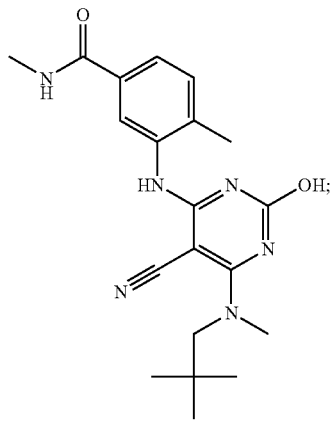
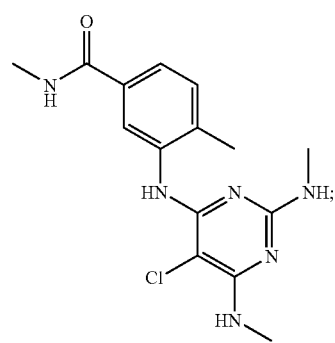
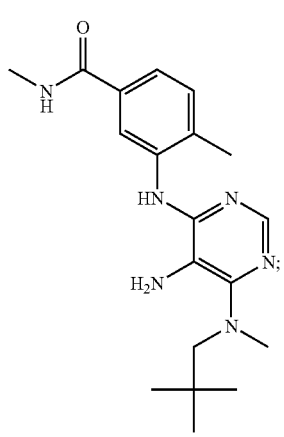
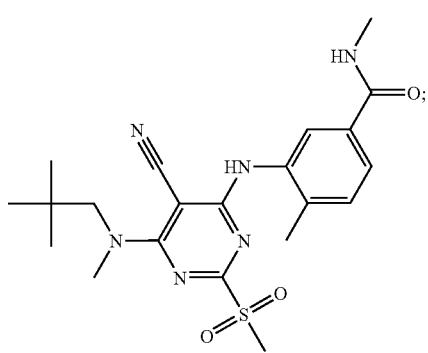
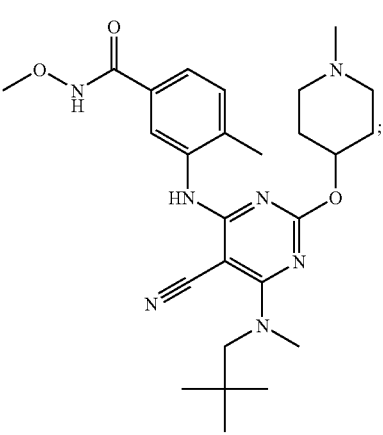
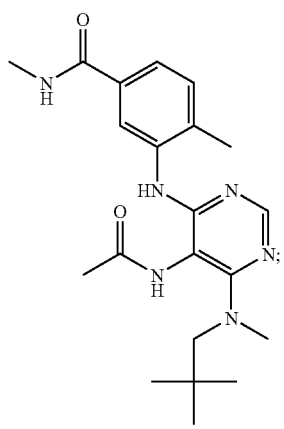

-continued
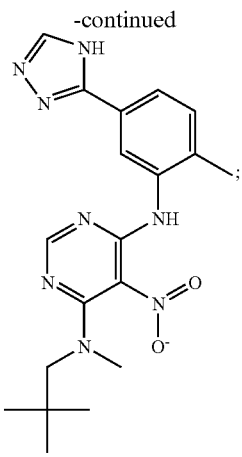
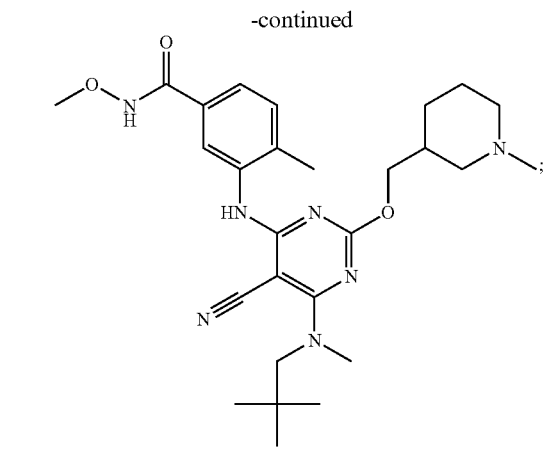
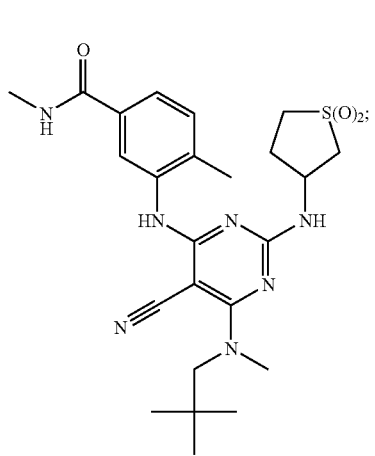
lp;3p
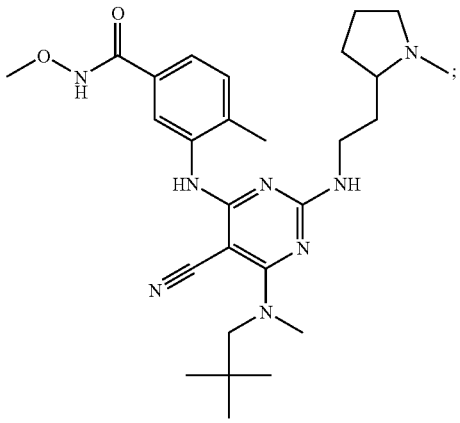
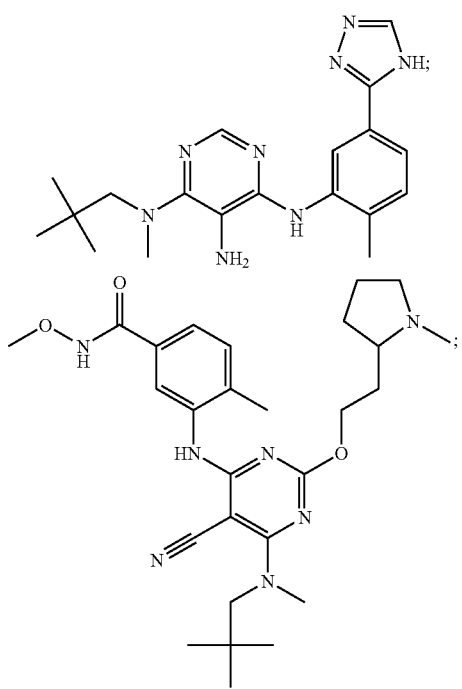
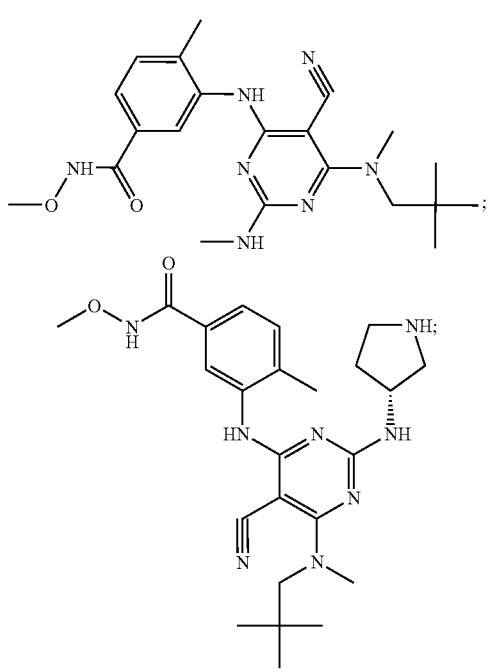

-continued
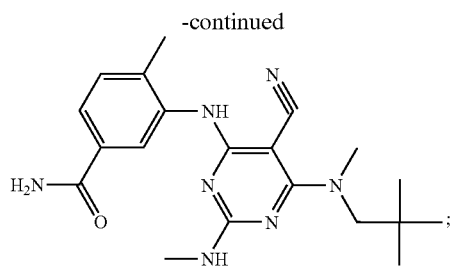
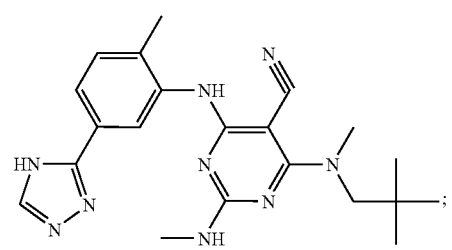
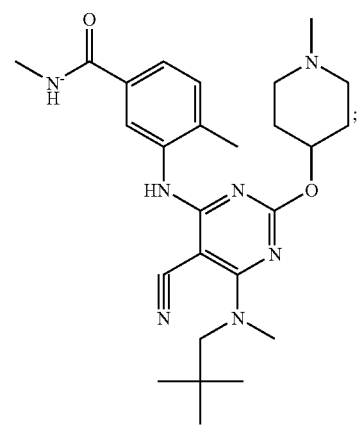
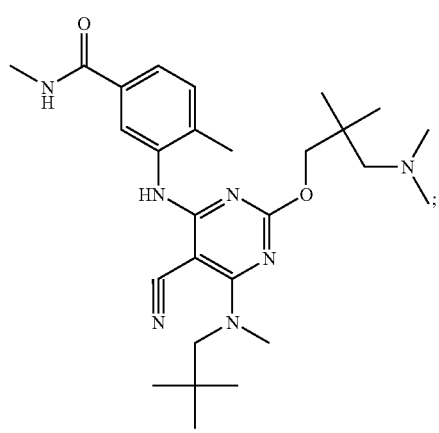
-continued
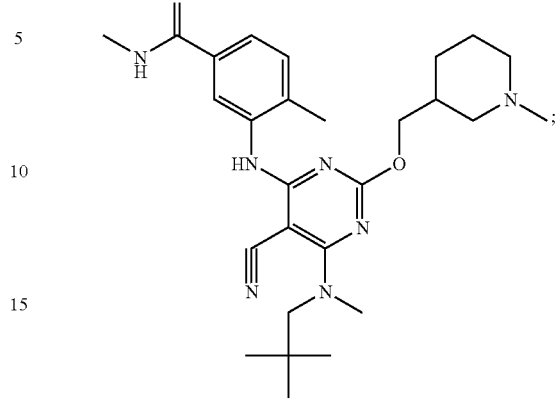
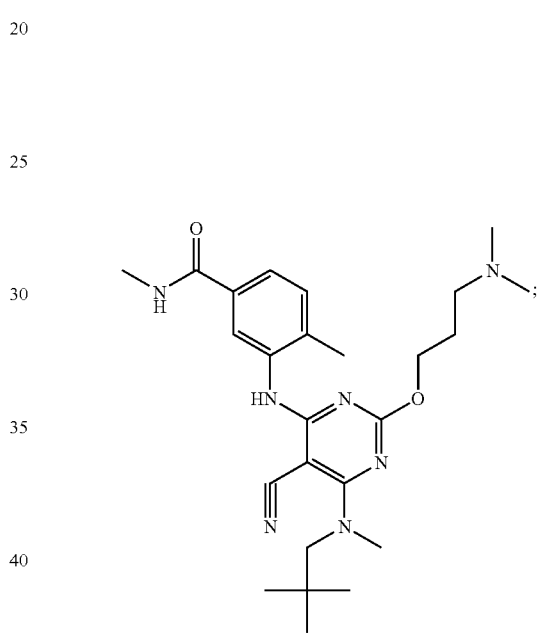
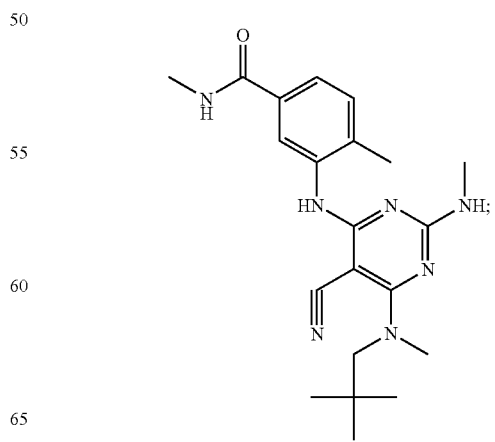

25
-continued
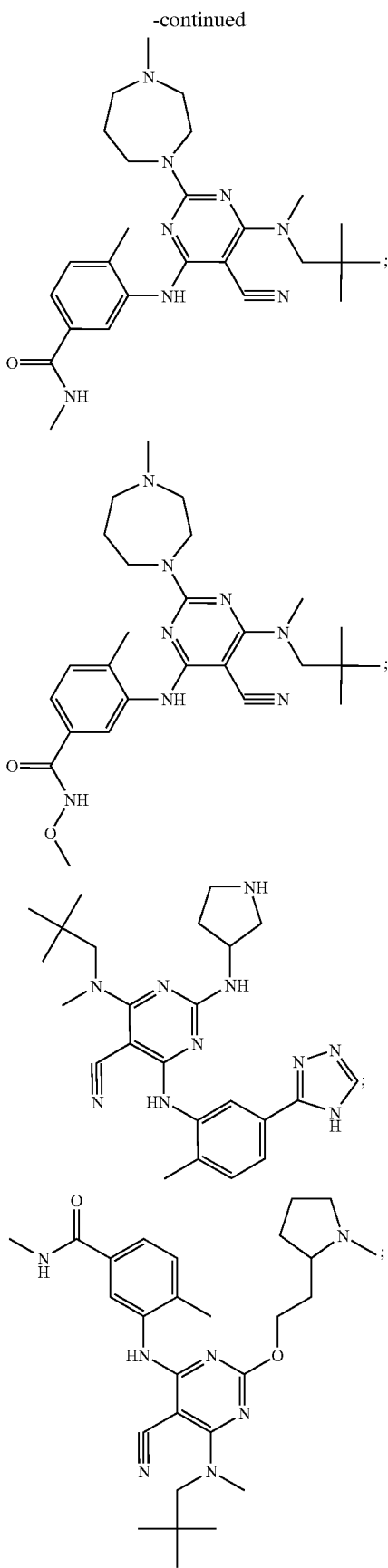
26
-continued
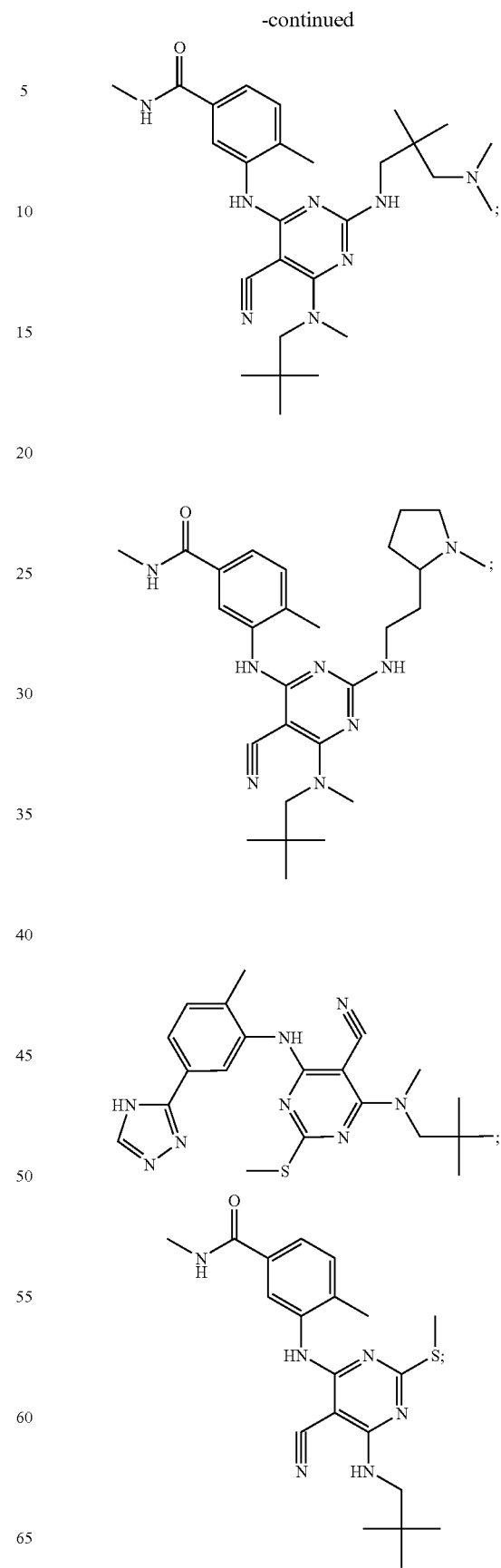

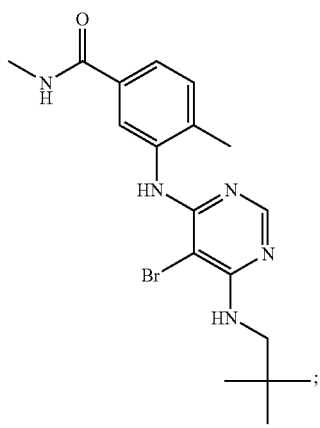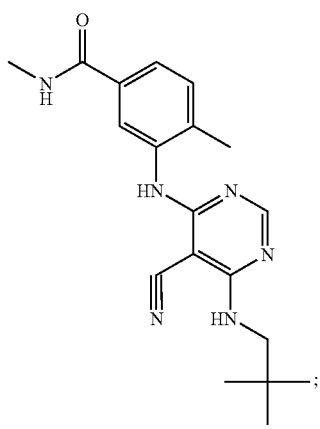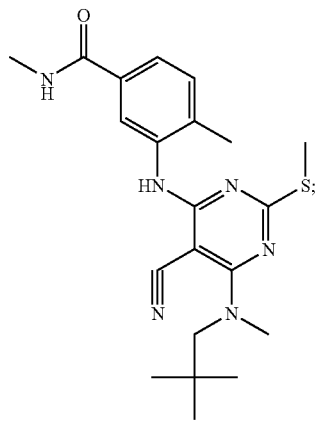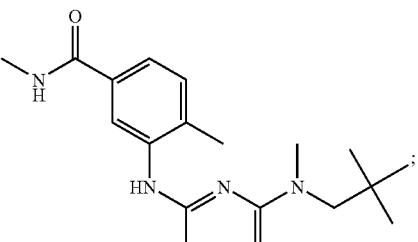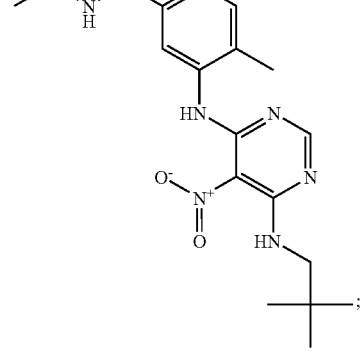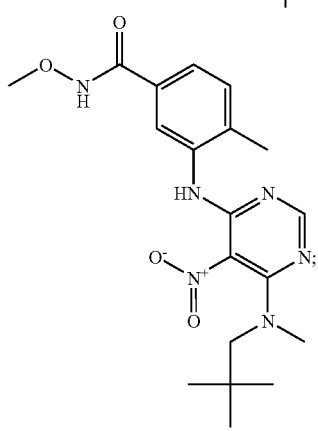

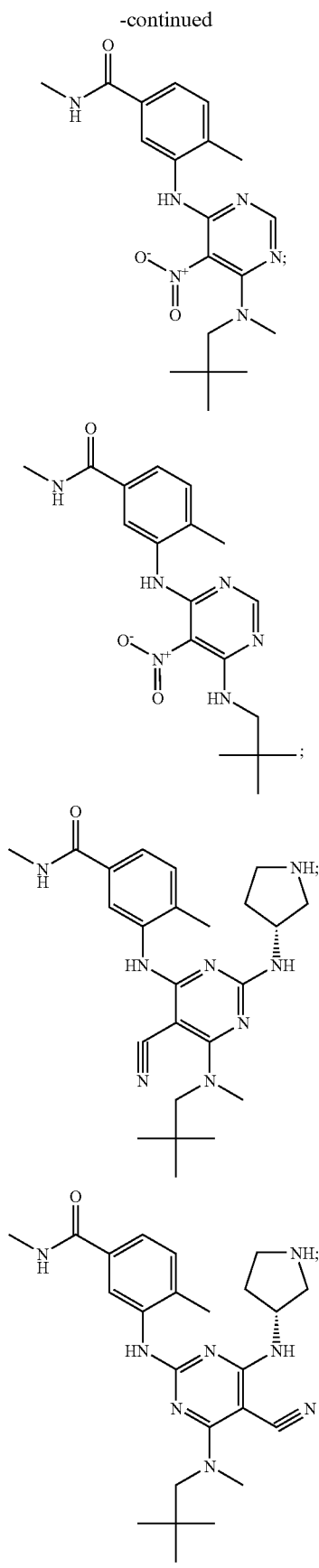
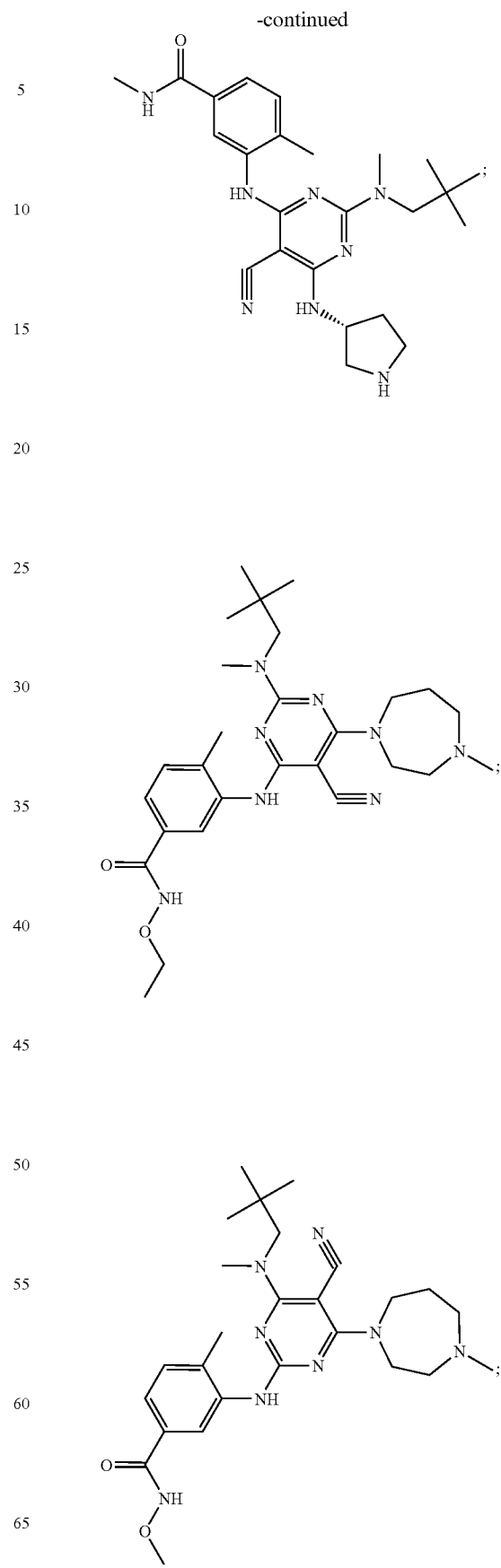

Abbreviations & Definitions

The following terms and abbreviations retain the indicated meaning throughout this disclosure.
ATP=adenosine triphosphate
cDNA=complementary DNA
DCE=dichloroethylene
DCM=dichloromethane=methylene chloride=$CH_2Cl_2$
DIC=diisopropylcarbodiimide
DIEA=N,N-diisopropylethylamine
DMF=N,N-dimethylformamide
DMSO=dimethyl sulfoxide
DTT=dithiothreitol
EDTA=ethylenediaminetetraacetic acid
EIA=enzyme immunoassay
ELISA=enzyme-linked immunosorbent assay
Fmoc=9-fluorenylmethoxycarbonyl
GST=glutathione S-transferase
HOBt=1-hydroxybenzotriazole
LPS=lipopolysaccharide
MBP=myelin basic protein
MES=2-(N-morpholino)ethanesulfonic acid
mRNA=messenger RNA
PCR=polymerase chain reaction
Pr$_2$NEt=dipropylethylamine
i-Pr$_2$NEt=diisopropylethylamine
RPMI=Roswell Park Memorial Institute
TBS=t-butyldimethylsilyl
TFA=trifluoroacetic acid
THF=tetrahydrofuran "Alkyl" is intended to include linear or branched hydrocarbon structures and combinations thereof of 1 to 20 carbons. "Lower alkyl" means alkyl groups of from 1 to about 10, preferably from 1 to about 8, and more preferably, from 1 to about 6 carbon atoms. Examples of such radicals include methyl, ethyl, n-propyl, isopropyl, n-butyl, isobutyl, s-butyl, t-butyl, pentyl, iso-amyl, hexyl, octyl and the like.

"Aryl" means an aromatic hydrocarbon radical of 6 to about 16 carbon atoms, preferably of 6 to about 12 carbon atoms, and more preferably of 6 to about 10 carbon atoms. Examples of aryl groups are phenyl, which is preferred, 1-naphthyl and 2-naphthyl.

"Cycloalkyl" refers to saturated hydrocarbon ring structures of from 3 to 12 carbon atoms, and preferably from 3 to 6 carbon atoms. Examples include cyclopropyl, cyclobutyl, cyclopentyl, cyclohexyl, norbornyl, adamantyl, and the like. "Lower cycloalkyl" refers to cycloalkyl of 3 to 6 carbons.

"Heterocyclyl" refers to saturated, partially saturated or unsaturated monocyclic structures of from 3 to 8 atoms, preferably 5 or 6 atoms, and bicyclic structures of 9 or 10 atoms containing one or more carbon atoms and from 1 to 4 heteroatoms chosen from O, N, and S. The point of attachment of the heterocyclyl structure is at an available carbon or nitrogen atom. Examples include: imidazole, pyridine, indole, thiophene, benzopyranone, thiazole, furan, benzimidazole, quinoline, isoquinoline, quinoxaline, pyrimidine, pyrazine, tetrazole, pyrazole, pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, imidazolinyl, imidazolidinyl, pyrazolinyl, pyrazolidinyl, isoxazolyl, isothiazolyl, 1,2,3-oxadiazolyl, 1,2,3-triazolyl, 1,2,4-triazolyl, 1,3,4-thiadiazolyl, 2H-pyranyl, 4H-pyranyl, piperidinyl, 1,4-dithianyl, thiomorpholinyl, pyrazinyl, piperazinyl, 1,3,5-triazinyl, 1,2,5-trithianyl, benzo(b)thiophenyl, benzimidazolyl, quinolinyl, and the like.

"Alkoxy" means a straight, branched or cyclic hydrocarbon configuration and combinations thereof, including from 1 to 20 carbon atoms, preferably from 1 to 8 carbon atoms, more preferably from 1 to about 4 carbon atoms, and an oxygen atom at the point of attachment. Suitable alkoxy groups include methoxy, ethoxy, n-propoxy, isopropoxy, n-butoxy, iso-butoxy, s-butoxy, t-butoxy, cyclopropyloxy, cyclohexyloxy, and the like. "Lower alkoxy" refers to alkoxy groups having from 1 to 4 carbon atoms. Similarly, "alkylthio" refers to such groups having a sulfur atom at the point of attachment.

"Alkenyl" refers to an unsaturated acyclic hydrocarbon radical in so much as it contains at least one double bond. "Lower alkenyl" refers to such radicals containing from about 2 to about 10 carbon atoms, preferably from about 2 to about 8 carbon atoms and more preferably 2 to about 6 carbon atoms. Examples of suitable alkenyl radicals include propenyl, buten-1-yl, isobutenyl, penten-1-yl, 2-methylbuten-1-yl, 3-methylbuten-1-yl, hexen-1-yl, hepten-1-yl, and octen-1-yl, and the like.

"Alkynyl" refers to an unsaturated acyclic hydrocarbon radical containing at least one triple bond. Examples include ethynyl, propynyl, and the like.

"Substituted alkyl" means an alkyl wherein one or more hydrogens, preferably one, two, or three hydrogens, attached to an aliphotic carbon are replaced with a substituent such as —N($R^{31}$)($R^{32}$), alkoxy, alkylthio, halogen, cyano, carboxyl, hydroxyl, —$SO_2$-alkyl, —$CO_2$-alkyl, —C(O)-alkyl, nitro, cycloalkyl, substituted cycloalkyl, aryl, substituted aryl, heterocyclyl, substituted heterocyclyl, —C(O)—N($R^{31}$)($R^{32}$), or —NH—C(O)-alkyl. Examples of such substituent groups include methoxy, ethoxy, propoxy, amino, methylamino, dimethylamino, phenyl naphthyl, chlorine, fluorine, and the like.

"Substituted cycloalkyl" means a cycloalkyl wherein one or more hydrogens, preferably one, two or three hydrogens, attached to a ring carbon are replaced with a substituent such as alkyl, substituted alkyl, —N($R^{31}$)($R^{32}$), alkoxy, alkylthio, aryl, substituted aryl, halogen, cyano, carboxyl, hydroxyl, nitro, —$SO_2$-alkyl, —$CO_2$-alkyl, —C(O)-alkyl, —C(O)—N($R^{31}$)$R^{32}$), or —NH—C(O)-alkyl. Examples of such groups include methyl, isopropyl, methoxy, ethoxy, propoxy, amino, methylamino, dimethylamino, phenyl, chlorine, fluorine and the like. Also included within this definition are cycloalkyl rings having a fused aryl, preferably phenyl, or cycloalkyl such as

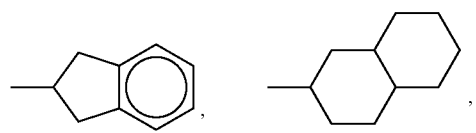

and the like.

"Substituted aryl" means an aryl wherein one or more hydrogens, preferably one, two or three hydrogens, attached to an aromatic carbon are replaced with a substituent such as alkyl, substituted alkyl, —N($R^{31}$)($R^{32}$), alkoxy, alkylthio, aryl, substituted aryl, halogen, cyano, nitro, carboxyl, hydroxyl, —$SO_2$-alkyl, —$CO_2$-alkyl, —C(O)-alkyl, —C(O)—N($R^{31}$)($R^{32}$), or —NH—C(O)-alkyl. Examples of such substituents include methyl, isopropyl, methoxy, ethoxy, propoxy, amino, methylamino, dimethylamino, phenyl, chlorine, fluorine, —$CO_2CH_3$, —C(O)—$NH_2$, and the like.

"Substituted heterocyclyl" means a heterocyclyl substituted at one or more available carbon or nitrogen atoms, preferably at one or two carbon and/or nitrogen atoms, with a substituent such as alkyl, substituted alkyl, —N($R^{31}$)($R^{32}$), alkoxy, alkylthio, aryl, substituted aryl, halogen, cyano, nitro, oxo, carboxyl, hydroxyl, —$SO_2$-alkyl, —$CO_2$-alkyl, —C(O)-alkyl, —C(O)—N($R^{31}$)($R^{32}$), or —NH—C(O)-alkyl. Examples of such groups include methyl isopropyl, methoxy, ethoxy, propoxy, amino, methylamino, dimethylamino, phenyl, chlorine, fluorine and the like.

"Halogen" is intended to include for example, F, Cl, Br and I.

The term "prodrug" refers to a chemical compound that is converted to an active agent by metabolic processes in vivo. [See, e.g., N. Boder and J. J. Kaminski, *Ann. Rep. Med. Chem.* 22:303 (1987) and H. Bundgarrd, *Adv. Drug Delivery Rev.*, 3:39 (1989)]. With regard to the present invention, a prodrug of a compound of Formula I is intended to mean any compound that is converted to a compound of Formula I by metabolic processes in vivo. The use of prodrugs of compounds of Formula I in any of the methods described herein is contemplated and is intended to be within the scope of the invention.

Terminology related to "protected," "protecting" and/or "deprotecting" functionalities is used throughout this application. Such terminology is well understood by persons of skill in the art and is used in the context of processes which involve sequential treatment with a series of reagents. In this context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups" for the functionalities involved.

In the case of the present invention, the typical functionalities that must be protected are amines. Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapter entitled "Protection for the Amino Group" (pages 309-405). Preferred protecting groups include BOC and Fmoc. Exemplary methods for protecting and deprotecting with these groups are found in Greene and Wuts on pages 318 and 327.

Optical Isomers-Diastereomers-Geometric Isomers

Some of the compounds described herein contain one or more asymmetric centers and may thus give rise to enantiomers, diastereomers, and other stereoisometric forms which may be defined in terms of absolute stereochemistry as (R)— or (S)—, or as (D)- or (L)- for amino acids. The present invention is meant to include all such possible diastereomers as well as their racemic and optically pure forms. Optically active (R)- and (S)- or (D)- and (L)-isomers may be prepared using chiral synthons or chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

Compounds of the invention which incorporate chiral diamines may be resolved into pairs of enantiomers by known techniques. Where pure enantiomers of starting materials are not commercially available, they may be obtained by classic resolution, which may employ, for example, fractional crystallization of diastereomeric salts. Compounds of the invention may have more than one chiral center, for example wherein reductive amination of a homochiral intermediate leads to a mixture of diastereomers. Racemic intermediates and compounds of the invention may also be resolved by chromatographic separation, such as for example, HPLC using a column loaded with a homochiral support, to yield pure isomeric compounds.

The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion.

In view of the above definitions, other chemical terms used throughout this application can be easily understood by those of skill in the art. Terms may be used alone or in any combination thereof. The preferred and more preferred chain lengths of the radicals apply to all such combinations.

Utility

The compounds of the present invention have demonstrated utility as selective inhibitors of inappropriate p38 kinase activity, and in particular, isoforms p38α and p38β. As such, compounds of the present invention have utility in the treatment of conditions associated with inappropriate p38 kinase activity. Such conditions include diseases in which cytokine levels are modulated as a consequence of intracellular signaling via p38, and in particular, diseases that are associated with an overproduction of such cytokines as Il-1, Il-4, IL-8, and in particular, TNF-α.

As inhibitors of p-38 kinase activity, compounds of the present invention are useful in the treatment and prevention of p-38 mediated conditions including, but not limited to, inflammatory diseases, autoimmune diseases, destructive bone disorders, proliferative disorders, angiogenic disorders, infectious diseases, neurodegenerative diseases, viral diseases, allergies, myocardial ischemia, reperfusion/ischemia in stroke, heart attacks, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented include, but are not limited to, acute pancreatitis, chronic pancreatitis, asthma, allergies and adult respiratory distress syndrome.

Autoimmune diseases which may be treated or prevented include, but are not limited to, glomerulonephritis, rheumatoid arthritis, systemic lupus erythematosis, scleroderma, chronic thyroiditis, Grave□s disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented include, but are not limited to, osteoporosis, osteoarthritis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Infectious diseases which may be treated or prevented include, but are not limited to, sepsis, septic shock, and Shigellosis.

Neurodegenerative diseases which may be treated or prevented by the compounds of this invention include, but are not limited to, Alzheimer's disease, Parkinson's disease, cerebral ischemias or neurodegenerative disease caused by traumatic injury.

Angiogenic disorders which may be treated or prevented include solid tumors, ocular neovasculization, infantile haemangiomas.

Viral diseases which may be treated or prevented include, but are not limited to, acute hepatitis infection (including hepatitis A, hepatitis B and hepatitis C), HIV infection and CMV retinitis.

In addition, p38 inhibitors of this invention also exhibit inhibition of the expression of inducible pro-inflammatory proteins such as prostaglandin endoperoxide synthase-2 (PGHS-2), also referred to as cyclooxygenase-2 (COX-2). Accordingly, additional p38 mediated conditions include edema, analgesia, fever and pain, such as neuromuscular pain, headache, pain caused by cancer, dental pain and arthritis pain.

As a result of their p38 inhibitory activity, compounds of the present invention have utility in the treatment and prevention of diseases associated with cytokine production. For example, compounds of the present invention are useful in the treatment and prevention of:

Il-1 mediated diseases such as, for example, rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes, pancreatic β-cell disease and Alzheimer's disease;

IL-8 mediated diseases or conditions such as, for example, those characterized by massive neutrophil infiltration, such as psoriasis, inflammatory bowel disease, asthma, cardiac and renal reperfusion injury, adult respiratory distress syndrome, thrombosis and glomerulonephritis; and TNF-mediated diseases or conditions such as rheumatoid arthritis, rheumatoid spondylitis, osteoarthritis, gouty arthritis and other arthritic conditions, sepsis, septic shock syndrome, adult respiratory distress syndrome, cerebral malaria, chronic pulmonary inflammatory disease, silicosis, pulmonary sarcoisosis, bone resorption disease, reperfusion injury, graft vs. host reaction, allograft rejections, fever and myalgias due to infection, cachexia secondary to infection, AIDS, ARC or malignancy, meloid formation, scar tissue formation, Crohn's disease, ulcerative colitis, pyresis, viral infections, such as HIV, CMV, influenza and herpes; and veterinary viral infections, such as lentivirus infections, including, but not limited to equine infectious anemia virus; or retro virus infections, including feline immunodeficiency virus, bovine immunodeficiency virus, or canine immunodeficiency virus.

The compounds of formula I including a pharmaceutically acceptable salt or hydrate thereof may be administered by any suitable route as described previously to treat the above mentioned diseases and conditions. The method of administration will, of course, vary depending upon the type of disease being treated. The amount of active compound administered will also vary according to the method of administration and the disease being treated. An effective amount will be within the dosage range of about 0.1 to about 100 mg/kg, preferably about 0.2 to about 50 mg/kg, in a single or multiple doses administered at appropriate intervals throughout the day.

The $IC_{50}$ values (concentration required to inhibit 50% of specific binding) of compounds of the present invention for inhibition of p38 activity are below 5 μM. Preferred compounds have an $IC_{50}$ below 1 μM.

Biological Assays

Generation of p38 Kinases cDNAs of human p38α, β and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.*, 1247-1255 (1996)].

TNF-α Production by LPS-Stimulated PBMCS

Heparinized human whole blood was obtained from healthy volunteers. Peripheral blood mononuclear cells (PBMCs) were purified from human whole blood by Ficoll-Hypaque density gradient centrifugation and resuspended at a concentration of 5×10⁶/ml in assay medium (RPMI medium containing 10% fetal bovine serum). 50 μl of cell suspension was incubated with 50 μl of test compound (4× concentration in assay medium containing 0.2% DMSO) in 96 well-tissue culture plates for 5 minutes at room temperature. 100 μl of LPS (200 ng/ml stock) was then added to the cell suspension and the plate was incubated for 6 hours at 37° C. Following incubation, the culture medium was collected and stored at −20° C. TNFα concentration in the medium was quantified using a standard ELISA kit (Pharmingen-San Diego, Calif.). Concentrations of TNFα and IC50 values for test compounds (concentration of compound that inhibited LPS-stimulated TNFα production by 50%) were calculated by linear regression analysis.

LPS-Induced TNF Production in THP-1 Cells

Human monocytic THP-1 cells were maintained in RPMI 1640 medium supplemented with 10% fetal bovine serum. Cells (40,000 cells in 80 μl) were added to wells of 96-well flat-bottomed plates. Tested compounds (10 μl) or vehicle (3% DMSO) were added to wells. Subsequently, LPS (Sigma, #L7261; 10 μl/well) was added to the cells for a final concentration of 1 μg/mL. Plates were incubated overnight at 37° C. and 5% $CO_2$. Supernatant (50 μl/well) was harvested for an ELISA assay. TNF was captured by an anti-human TNF antibody (R&D, #MAB610) which was pre-absorbed in high binding EIA plates (Costar, #3590). Captured TNF was recognized by a biotinlated anti-human TNF polyclonal antibody (R&D, #BAF210). Streptavidin conjugated with peroxidase was added to each well, and the activity of peroxidase was quantitated by a peroxide substrate kit (Pierce, #34062 and #34006).

p38 Assay

The assays were performed in V-bottomed 96-well plates. The final assay volume was 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 μl of 0.5 M EDTA to each sample. The reaction mixture was aspirated onto a pre-wet filtermat using a Skatron Micro96 Cell Harvester (Skatron, Inc.), then wash with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPad Software). The final concentration of reagents in the assays are ATP, 1 μM; [γ-$^{33}$P]ATP, 3 nM; MBP (Sigma, # M1891), 2 μg/well; p38, 10 nM; and DMSO, 0.3%.

Methods of Synthesis

General methods of synthesis for compounds of the present invention are illustrated by the following examples. Compounds of the invention may be prepared by standard techniques known in the art, involving both solution and solid phase chemistry. Starting materials are commercially available or may by readily prepared by one of skill in the art with known methods, or by methods disclosed herein. Specific embodiments described are presented by way of illustration only, and the invention is not limited thereto.

Modifications and variations in any give material or process step will be readily apparent to one of skill in the art and all are to be included within the scope of the invention.

As illustrated in Scheme 1 and Scheme 2, compounds of Formula I wherein V is —NR$^5$—; one or two of W, X and Y are N; and each of Z and R$^{11}$ are attached to the core pyrimidine or pyridine by —N— or —O—, may be prepared from trihalopyrimidine by sequential reactions with three different amines (1, 2, 3), or two different amines (1, 2) and an alcohol, and subsequent introduction of an additional substituent on the pyrimidine core. An alternative method of preparation may start from dihalocyano-methyl-sulfanyl-pyrimidine (Scheme 2). Preferably, one of the amines will be an aniline and another will be a diamine suitably protected on its distal N. The person of skill will recognize that the amines themselves, the sequence of the three substitutions, as well as the position of the nitrile may be varied, and are not limited by the particular example shown in Scheme 1 or Scheme 2.

Scheme 1

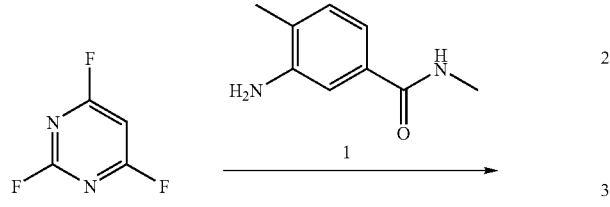

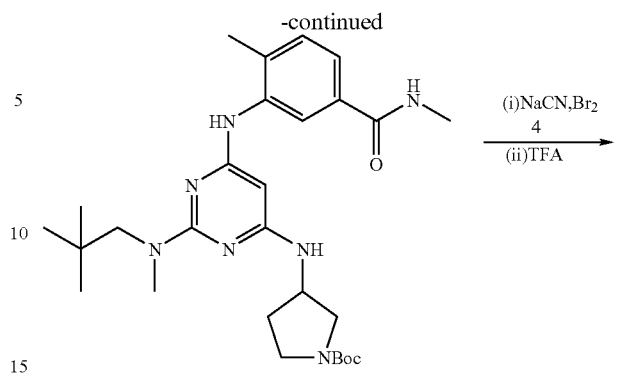

Scheme 2

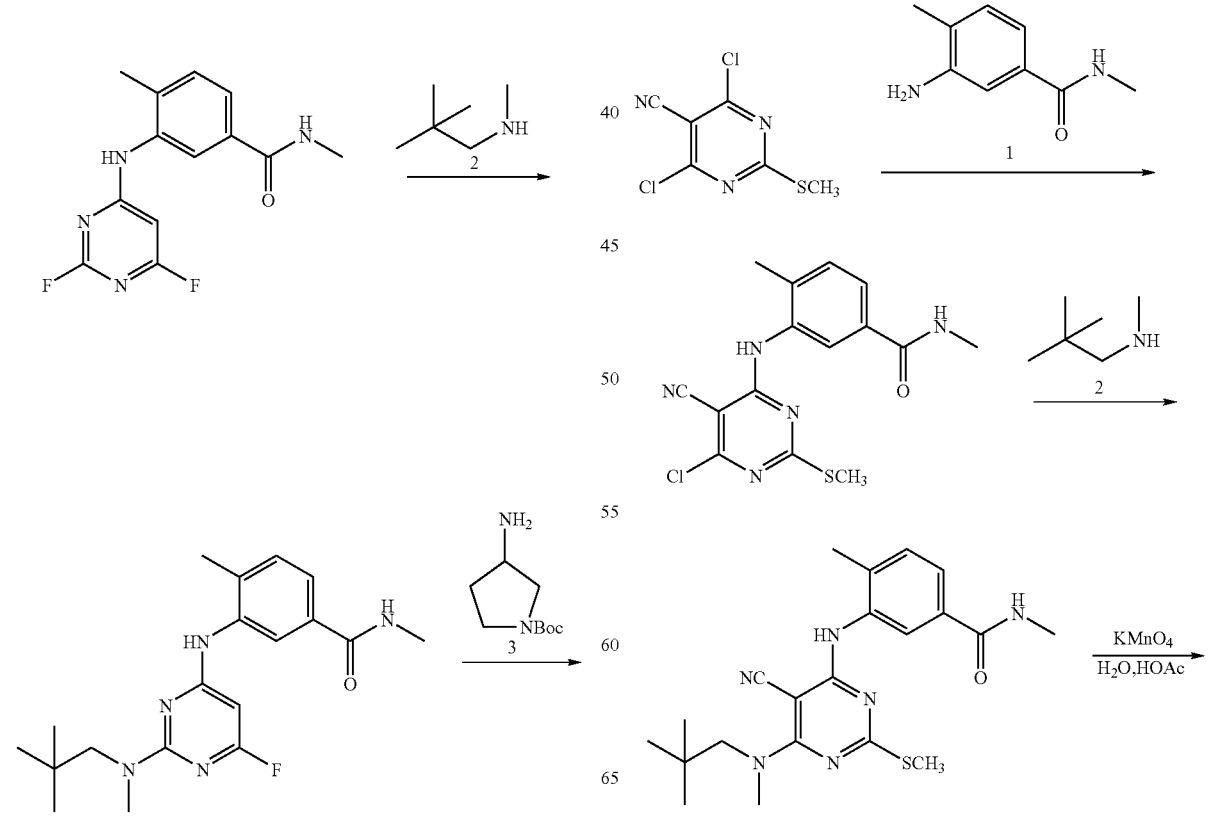

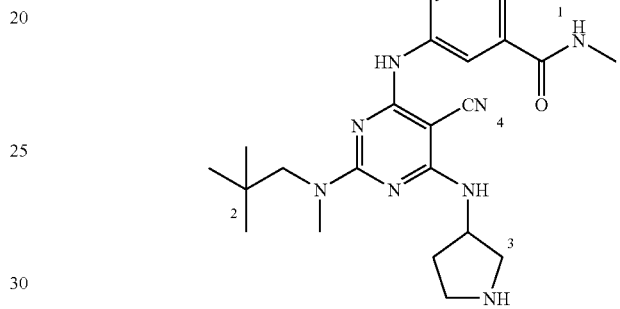

-continued

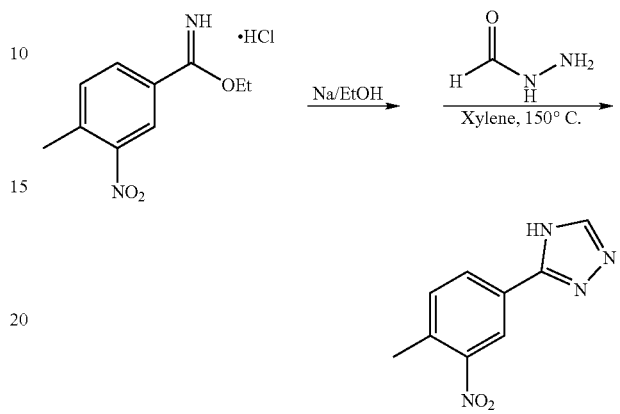

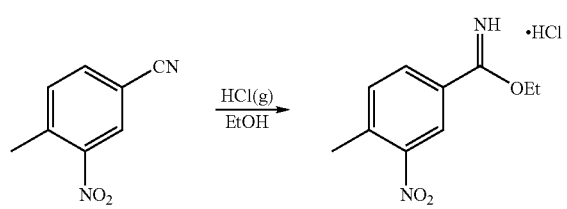

With respect to Formula I of the invention, Amine 1 corresponds to —N($R^5$)($R^6$); Amine 2 corresponds to -Z; and Amine 3 corresponds to —$R^{11}$ and such designations are used interchangeably in the description below.

Preparation of Amines 3-(4-Methyl-3-nitro-phenyl)-4H-[1,2,4]triazole

Hydrogen chloride was bubbled through a solution of 3-nitro-p-tolunitrile (0.49 g, 3 mmol) in 40 mL of ethanol at room temp for 10 min. The solution was continued stirring at room temp for 60 min and the solvent was then evaporated under vacuum to dryness to give a white solid.

The intermediate so obtained was dissolved in 20 mL of ethanol, neutralized with sodium ethoxide solution and the resulting precipitate was removed by filtration. To the filtrate was added at room temp formic hydrazide (0.2 g, 3 mmol) and the solution was continued stirring at room temp for 2 h. After removal of volatiles in vacuo, the residue was dissolved in 30 mL of m-xylene and refluxed at 150° C. for 16 h. Removal of volatiles in vacuo and purification using flash chromatography afforded 0.26 g of the final product. (Yield: 43%). MS (m/z) calcd for $C_9H_8N_4O_2$ (MH+) 205.2, found, 205.1.

Coupling of Substituted Pyridines with Amines

2-Chloro-6-[(2,2-dimethyl-propyl)-methyl-amino]-5-fluoro-nicotinonitrile

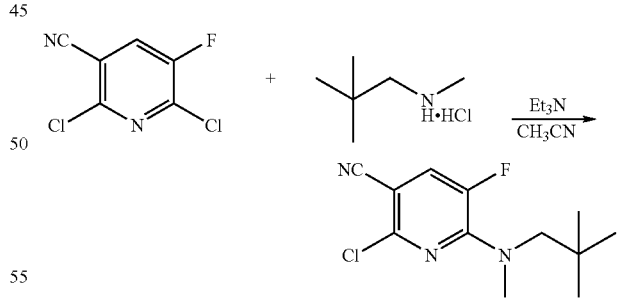

A solution of 2,6-dichloro-3-cyano-5-fluoropyridine (1.0 g, 5.23 mmol), N-methyl-neopentylamine hydrochloride (830 mg, 6.0 mmol) and triethylamine (1.6 mL) in acetonitrile (20 mL) was stirred at room temp for 4 hours. Then volatiles were removed in vacuo and the residue was partitioned between ethyl acetate and water. The organic layer was dried (sodium sulfate) and concentrated in vacuo to afford the product (1.11 g, 83%). $C_{12}H_{15}ClFN_3$ MS m/e=256 (M+H).

Preparation of Substituted Pyrimidines 4,6-Dichloro-2-methylsulfanyl-pyrimidine-5-carbaldehyde

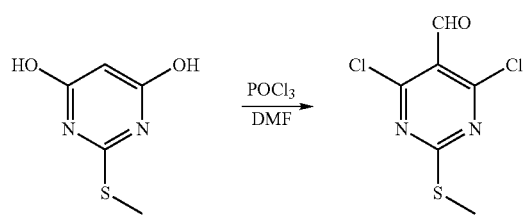

To phosphoryl chloride (108 mL) chilled in ice bath was added dimethylformamide (35 mL). The mixture was allowed to stand at 20 degree for one hour, then 25 g of 2-methylsulfanyl-pyrimidine-4,6-diol was added slowly. After 30 minutes, the reaction mixture was heated to 100° C. for 6 hours. The reaction mixture was poured onto crushed ice and the precipitate was collected by filtration. The crude product was purified with flash chromatography to afford 11.13 g of 4,6-Dichloro-2-methylsulfanyl-pyrimidine-5-carbaldehyde (Yield=32%). $^1$H-NMR (300 MHz, CDCl$_3$): δ 10.50 (s, 1H), 2.76 (s, 3H)

4,6-Dichloro-2-methylsulfanyl-pyrimidine-5-carbaldehyde oxime

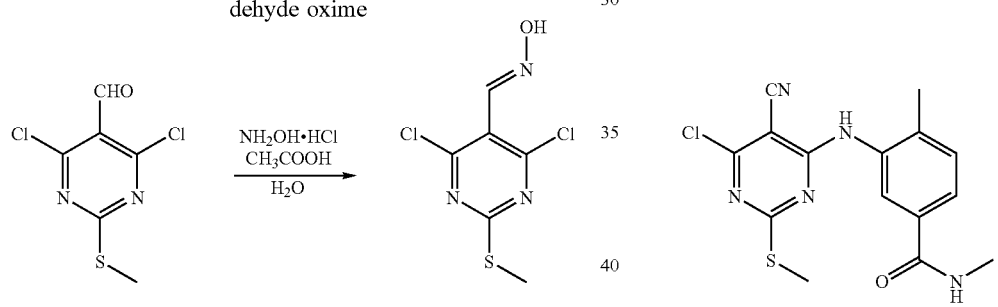

4,6-Dichloro-2-methylsulfanyl-pyrimidine-5-carbaldehyde (7.34 g, 33.09 mmol), hydroxylamine hydrochloride (2.31 g, 33.33 mmol), acetic acid (49.6 mL), and water (3.3 mL) were mixed, and heated to 60° C. for 2 hours. The reaction mixture was diluted with water and cooled under ice bath. The precipitate was collected and dried (Yield=6.41 g, 82%). MS (m/z): 238 (M+H).

4,6-Dichloro-2-methylsulfanyl-pyrimidine-5-carbonitrile

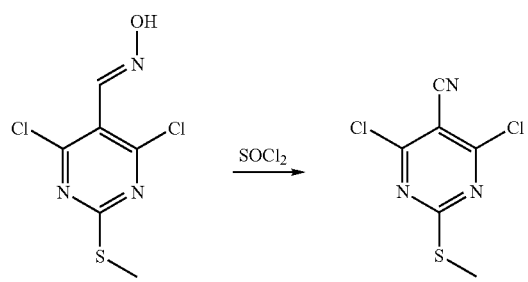

4,6-Dichloro-2-methylsulfanyl-pyrimidine-5-carbaldehyde oxime (7.20 g, 30.38 mmol) was added to neat thionyl chloride (29.63 g, 245 mmol), then the mixture was heated to reflux for 4 hours. The reaction mixture was poured onto ice-water. The precipitate of 4,6-dichloro-2-methylsulfanyl-pyrimidine-5-carbonitrile was collected and dried (Yield=6.15 g, 92%). $^1$H-NMR (300 MHz, CDCl$_3$) δ 2.75(s, 3H).

3-(6-Chloro-5-cyano-2-methylsulfanyl-pyrimidin-4-ylamino)-4,N-dimethyl-benzamide

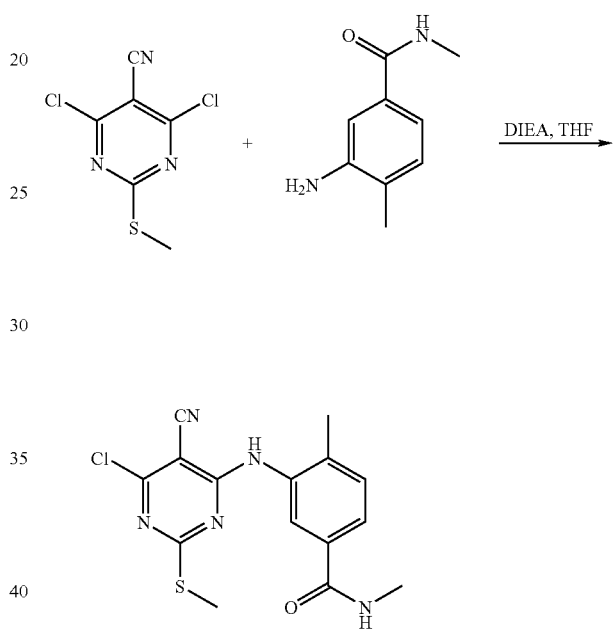

4,6-Dichloro-2-methylsulfanyl-pyrimidine-5-carbonitrile (2.19 g, 10 mmol), 3-amino-4,N-dimethyl-benzamide(1.64 g, 10 mmol), and DIEA(1.40 g, 18.8 mmol) were mixed in THF (20 mL). The resulting mixture was stirred at room temperature for overnight. The solvent was evaporated and the residue was partitioned between ethyl acetate and water. The organic layer was concentrated and the crude product was purified by flash chromatography to obtain 3-(6-chloro-5-cyano-2-methylsulfanyl-pyrimidin-4-ylamino)-4,N-dimethyl-benzamide (2.78 g, 80%). MS (m/z): 348 (M+H).

The following examples illustrate preferred embodiments of the present invention and do not limit the scope of the present invention, which is defined in the claims.

Compounds shown in Tables 1 and 2 have been synthesized according to the methods described herein and have been tested in accordance with the protocols described below. These compounds are provided by way of illustration only, and the invention is not intended to be limited thereto. Exemplary syntheses of some compounds are also provided.

TABLE 1

| Ex # | Structure | m/z | R$_t$ |
|---|---|---|---|
| 1 | | 367 | 4.67 |
| 2 | | 420, 422 | |
| 3 | | 433 | 3.09 |
| 4 | | 405 | 2.58 |

TABLE 1-continued
| Ex # | | m/z | R$_t$ |
|---|---|---|---|
| 5 | 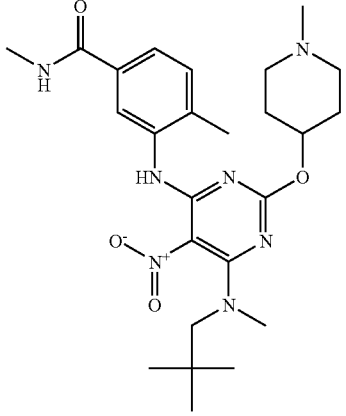 | 499 | |
| 6 | 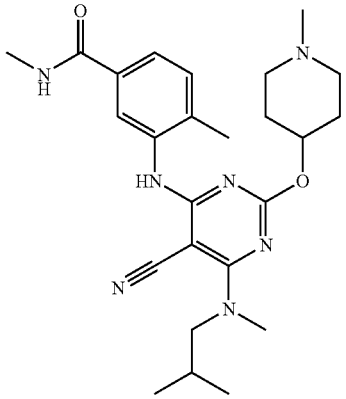 | 466 | 4.47 |
| 7 | 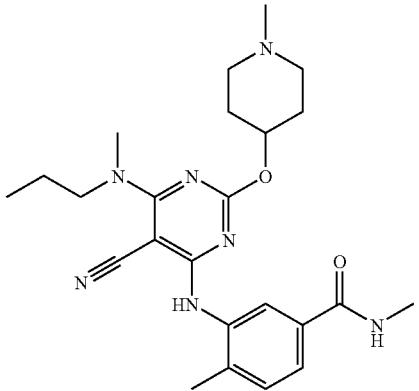 | 452 | 4.22 |

TABLE 1-continued

| Ex # | | m/z | R$_t$ |
|---|---|---|---|
| 8 | | 452 | 4.16 |
| 9 | | 424 | 3.56 |
| 10 | | 438 | 3.94 |
| 11 | | 435 | |

TABLE 1-continued
| Ex # | | m/z | R$_t$ |
|---|---|---|---|
| 12 | 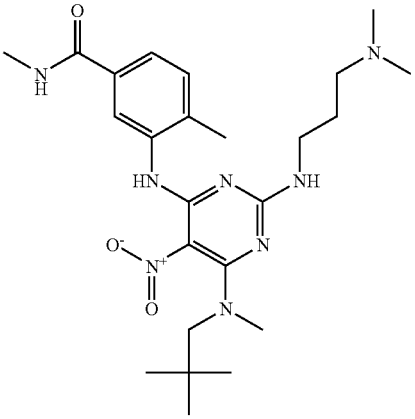 | 486 | |
| 13 | 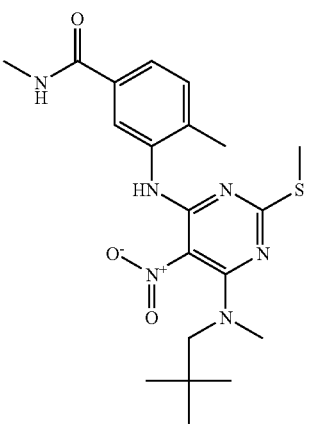 | 432 | |
| 14 | 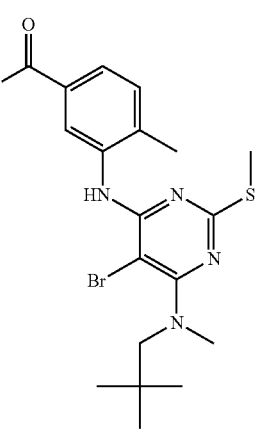 | 466 | |

TABLE 1-continued
| Ex # | | m/z | R_t |
|---|---|---|---|
| 15 | 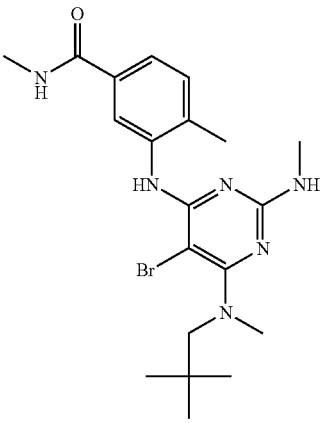 | 449 | |
| 16 | 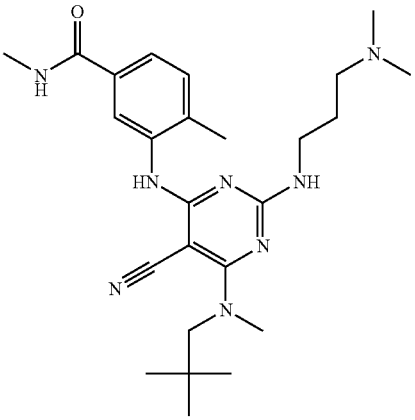 | 466 | |
| 17 | 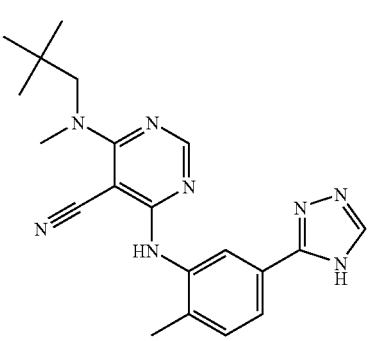 | 376 | |

TABLE 1-continued

| Ex # | | m/z | R_t |
|---|---|---|---|
| 18 | | 475 | 7.3 |
| 19 | | 405 | 6.2 |
| 20 | | 335 | 4.6 |
| 21 | | 445 | |

TABLE 1-continued

| Ex # | | m/z | R$_t$ |
|---|---|---|---|
| 22 | [structure] | 496 | 4.64 |
| 23 | [structure] | 383 | 10.3 |
| 24 | [structure] | 357 | |

TABLE 1-continued

| Ex # | | m/z | R$_t$ |
|---|---|---|---|
| 25 | | 399 | |
| 26 | | 396 | |
| 27 | | 500 | 11.0 |
| 28 | | 366 | |

TABLE 1-continued

| Ex # | | m/z | R_t |
|---|---|---|---|
| 29 | | 510 | 4.81 |
| 30 | | 509 | 4.84 |
| 31 | | 509 | 4.28 |
| 32 | | 412 | 6.0 |

TABLE 1-continued
| Ex # | | m/z | R$_t$ |
|---|---|---|---|
| 33 | 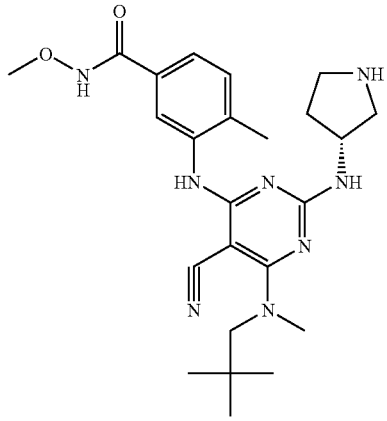 | 467 | |
| 34 | 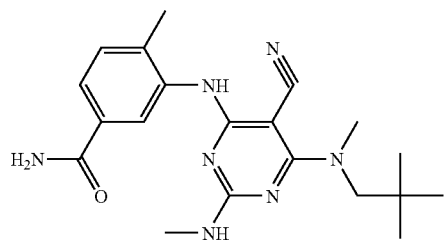 | | |
| 35 | 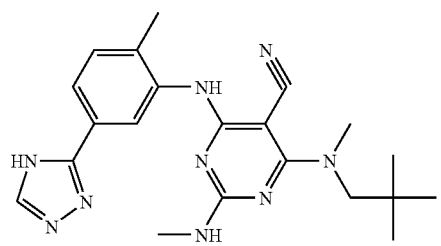 | 405 | 5.96 |

TABLE 1-continued
| Ex # | | m/z | R$_t$ |
|---|---|---|---|
| 36 | 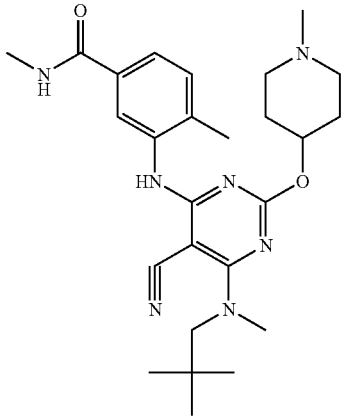 | 480 | 4.67 |
| 37 | 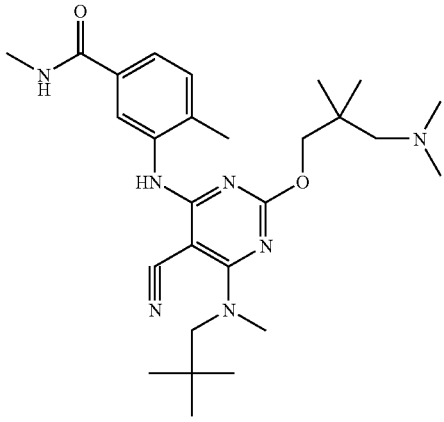 | 496 | 5.06 |
| 38 | 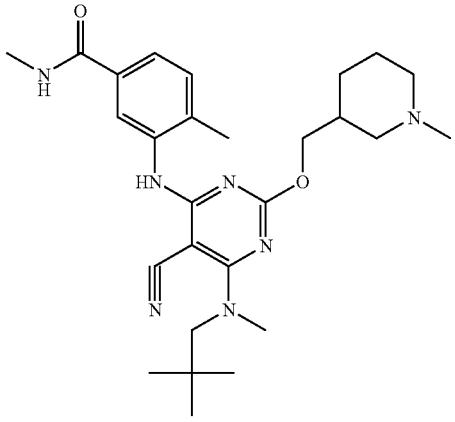 | 494 | 4.83 |

TABLE 1-continued

| Ex # | | m/z | R_t |
|---|---|---|---|
| 39 | (structure) | 468 | 4.69 |
| 40 | (structure) | 396 | |
| 41 | (structure) | 479 | |

TABLE 1-continued
| Ex # | | m/z | R_t |
|---|---|---|---|
| 42 | 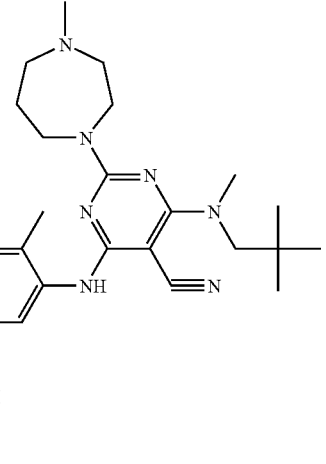 | 495 | |
| 43 | 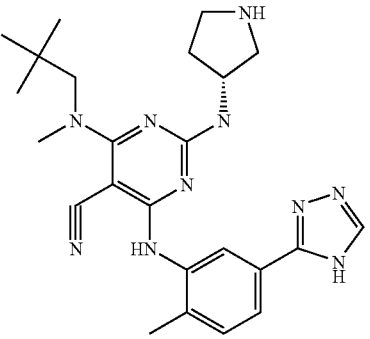 | 460 | 5.51 |
| 44 | 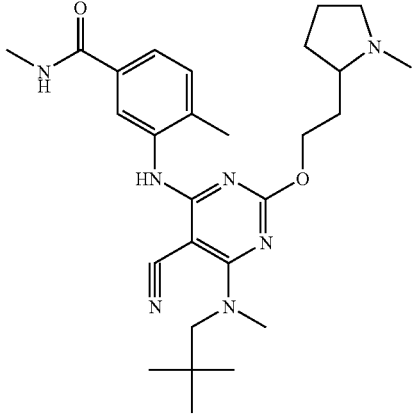 | 494 | 4.84 |

TABLE 1-continued

| Ex # | | m/z | R$_t$ |
|---|---|---|---|
| 45 | (structure) | 495 | 4.46 |
| 46 | (structure) | 493 | 4.20 |
| 47 | (structure) | 422 | |

TABLE 1-continued

| Ex # | | m/z | R$_t$ |
|---|---|---|---|
| 48 | (structure) | 399 | 7.5 |
| 49 | (structure) | 406, 409 | 5.7 |
| 50 | (structure) | 353 | 6.0 |

TABLE 1-continued
| Ex # | | m/z | R$_t$ |
|---|---|---|---|
| 51 | 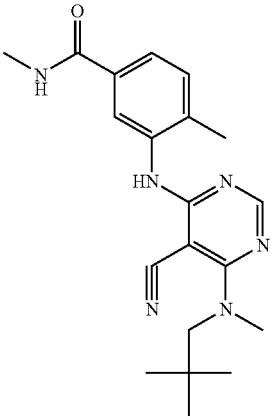 | 367 | 6.4 |
| 52 | 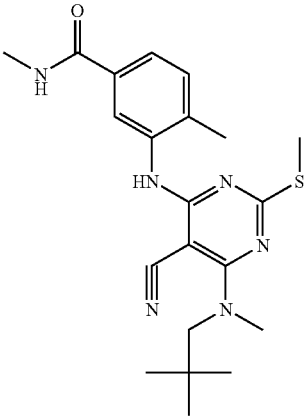 | 413 | 7.7 |
| 53 | 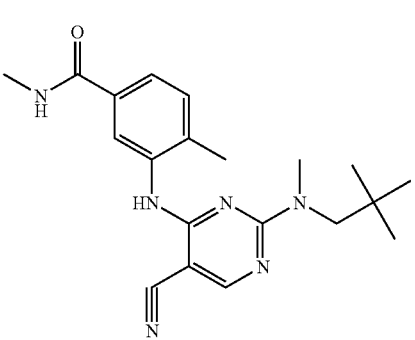 | 367 | 4.53 |

TABLE 1-continued
| Ex # | | m/z | R_t |
|---|---|---|---|
| 54 | 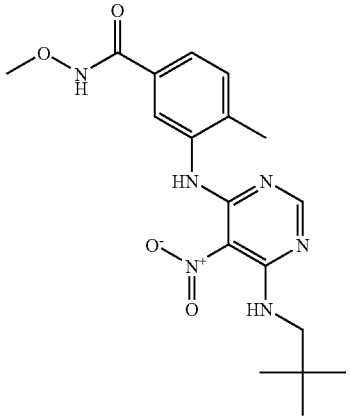 | 389 | |
| 55 | 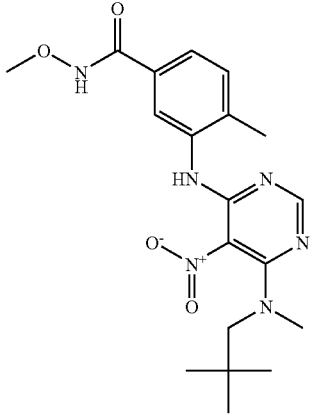 | 403 | |
| 56 | 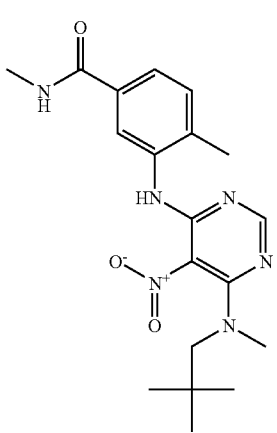 | 387 | 6.9 |

TABLE 1-continued
| Ex # | | m/z | R$_t$ |
|---|---|---|---|
| 57 | 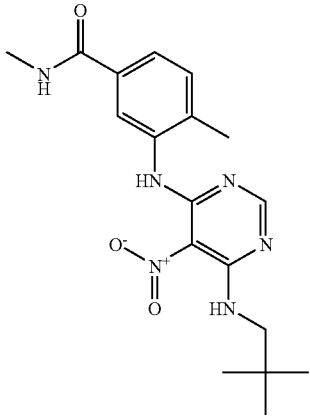 | 373 | 7.0 |
| 58 | 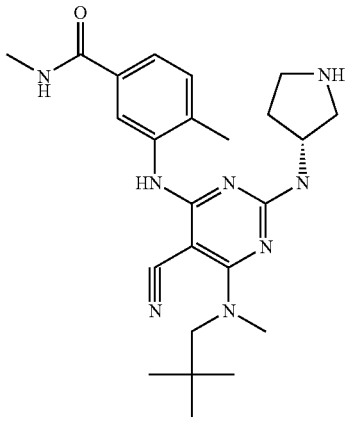 | 451 | |
| 59 | 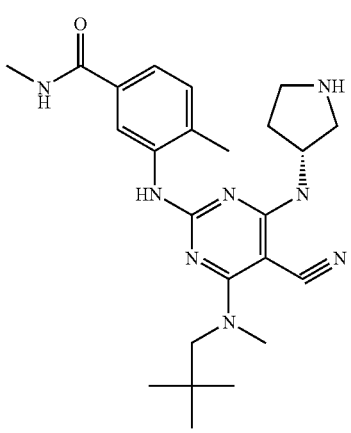 | 451 | |

TABLE 1-continued

| Ex # | | m/z | R$_t$ |
|---|---|---|---|
| 60 | | 451 | |
| 61 | | 509 | 12.5 |
| 62 | | 495 | 12.4 |

TABLE 2
| Example #70 | 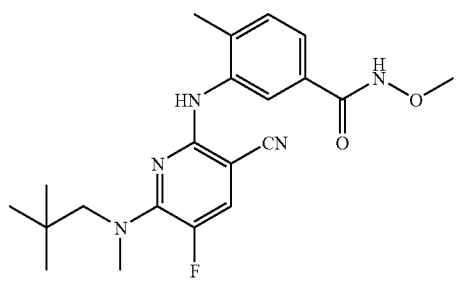 |
|---|---|
| Example #71 | 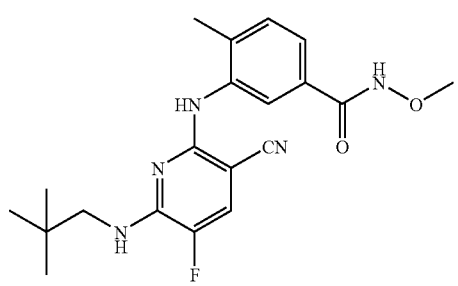 |
| Example #72 | 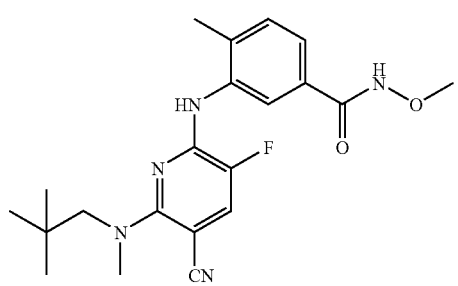 |
| Example #73 | 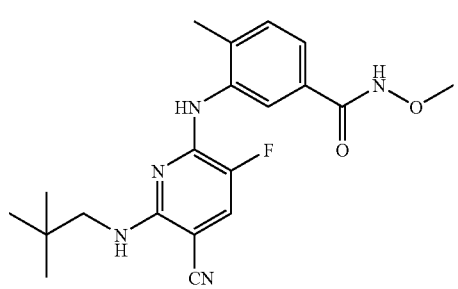 |
TABLE 2-continued
| Example #74 | 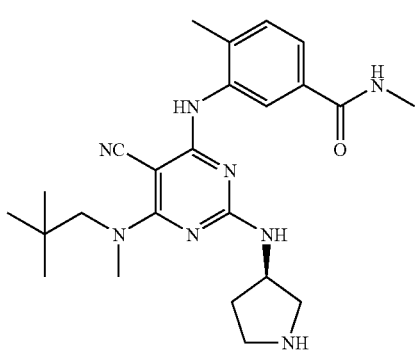 |
|---|---|
| Example #75 | 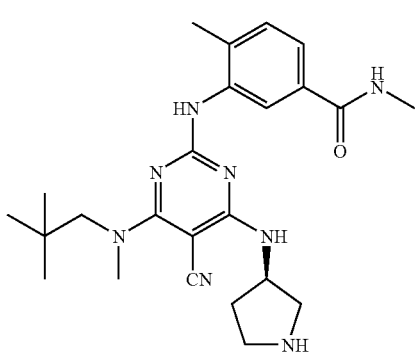 |
| Example #76 | 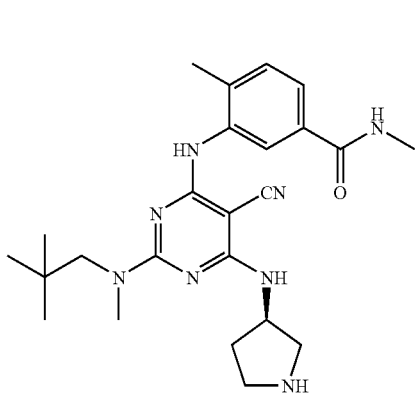 |
| Example #77 | 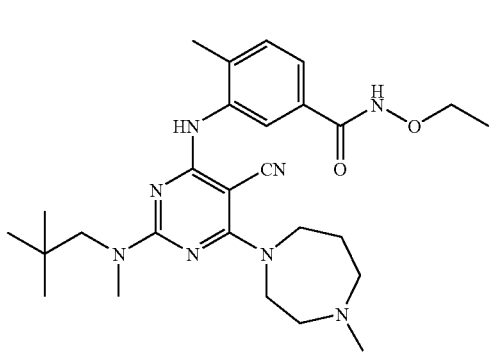 |

TABLE 2-continued

| Example #78 | 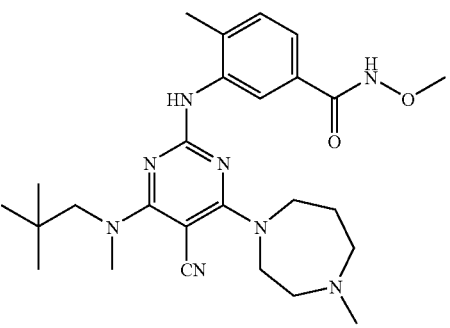 |
|---|---|

EXAMPLE 70

Synthesis of 3-{3-Cyano-6-[(2,2-dimethyl-propyl)-methyl-amino]-5-fluoro-pyridin-2-ylamino}-N-methoxy-4-methyl-benzamide

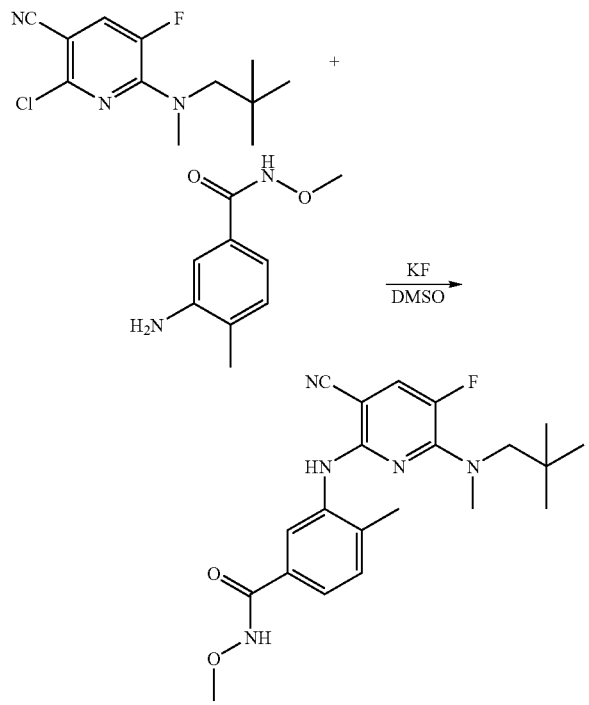

A mixture of 2-chloro-6-[(2,2-dimethyl-propyl)-methyl-amino]-5-fluoro-nicotinonitrile (120 mg, 0.47 mmol), 3-amino-N-methoxy-4-methyl-benzamide (120 mg, 0.66 mmol) and potassium fluoride (30 mg, 0.51 mmol) in DMSO (1 mL) was heated to 150° C. overnight. The reaction mixture was allowed to cool down to room temp and then partitioned between water and ethyl acetate. The organic layer was dried (sodium sulfate) and concentrated under reduced pressure. The product (7.5 mg, 4%) was obtained after purification by silica gel chromatography with 30% EtOAc in hexane as eluent. $C_{21}H_{26}FN_5O_2$ MS m/e=400 (M+H).

EXAMPLE 71

Synthesis of 3-{3-Cyano-6-[(2,2-dimethyl-propyl)-amino]-5-fluoro-pyridin-2-ylamino}-N-methoxy-4-methyl-benzamide

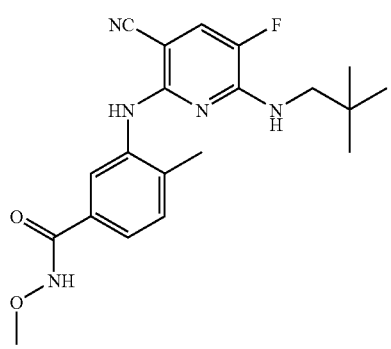

(a) Synthesis of 2-Chloro-6-[(2,2-dimethyl-propyl)-amino]-5-fluoro-nicotinonitrile

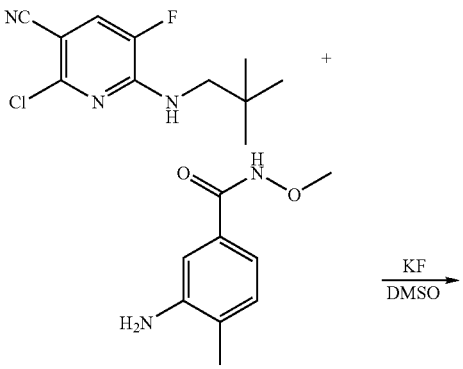

A mixture of 2,6-dichloro-3-cyano-5-fluoropyridine (1.0 g, 5.23 mmol), neopentylamine (530 mg, 6.0 mmol) and triethylamine (1 mL) in acetonitrile (20 mL) was stirred at room temp for 4 h. After the solvent was removed under reduced pressure, the residue was partitioned between ethyl acetate and water. The organic layer was dried (sodium sulfate) and concentrated under reduced pressure to afford the product (1.11 g, 87%). $C_{11}H_{13}ClFN_3$ MS m/e=242 (M+H).

(b) Synthesis of 3-{3-Cyano-6-[(2,2-dimethyl-propyl)-amino]-5-fluoro-pyridin-2-ylamino}-N-methoxy-4-methyl-benzamide -continued

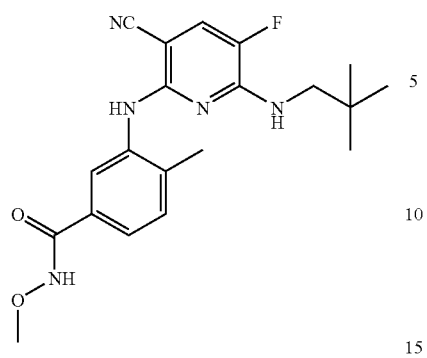

A mixture of 2-chloro-6-[(2,2-dimethyl-propyl)-amino]-5-fluoro-nicotinonitrile (150 mg, 0.62 mmol), 3-amino-N-methoxy-4-methyl-benzamide (150 mg, 0.83 mmol) and potassium fluoride (30 mg, 0.51 mmol) in DMSO (1 mL) was heated to 150° C. overnight. The reaction mixture was allowed to cool to room temp and then partitioned between water and ethyl acetate. The organic layer was dried (sodium sulfate) and concentrated under reduced pressure. The product (2.5 mg, 1%) was obtained after purification by silica gel chromatography with 30% EtOAc in hexane as eluent. $C_{20}H_{24}FN_5O_2$ MS m/e=386 (M+H).

EXAMPLE 73

Synthesis of 3-[5-Cyano-6-(2,2-dimethyl-propylamino)-3-fluoro-pyridin-2-ylamino]-N-methoxy-4-methyl-benzamide

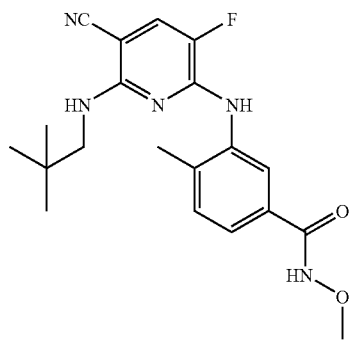

(a) 3-(3-Cyano-6-chloro-5-fluoro-pyridin-2-ylamino)-N-methoxy-4-methyl-benzamide

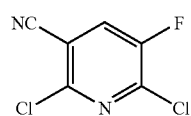 +

-continued

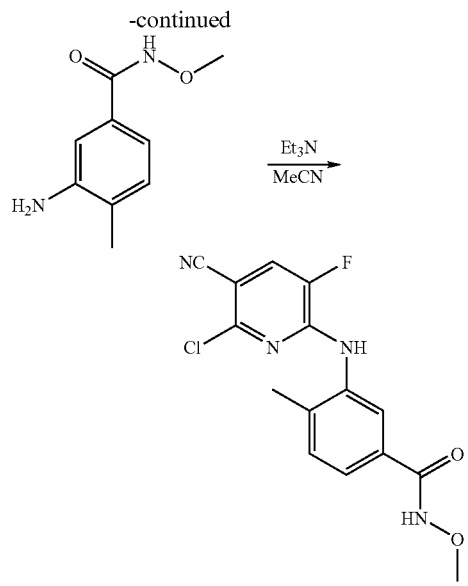

A mixture of 2,6-dichloro-5-fluoro-nicotinonitrile (830 mg, 4.34 mmol), 3-amino-N-methoxy-4-methyl-benzamide (576 mg, 3.2 mmol) and triethylamine (0.5 mL) in acetonitrile (10 mL) was heated to 70° C. overnight. Then the solvent was removed under reduced pressure and the reaction mixture was partitioned between water and ethyl acetate. The organic layer was dried (sodium sulfate) and concentrated under reduced pressure. The product (220 mg, 21%) was isolated after purification by silica gel chromatography. $C_{15}H_{12}ClFN_4O_2$ MS m/e=335 (M+H).

(b) Synthesis of 3-[5-Cyano-6-(2,2-dimethyl-propylamino)-3-fluoro-pyridin-2-ylamino]-N-methoxy-4-methyl-benzamide

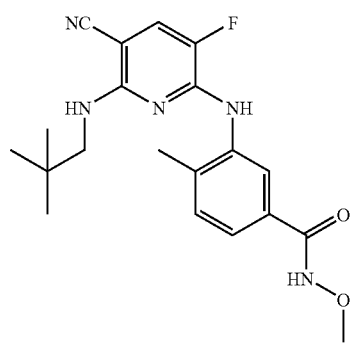

A mixture of 3-(6-chloro-5-cyano-3-fluoro-pyridin-2-ylamino)-N-methoxy-4-methyl-benzamide (52 mg, 0.15 mmol), neopentylamine (0.12 mL) and potassium fluoride (12 mg) in DMSO (1 mL) was heated to 150° C. overnight. The product (1.1 mg, 1.8%) was isolated after purification by HPLC. $C_{20}H_{24}FN_5O_2$ MS m/e=386 (M+H).

EXAMPLE 72

Synthesis of 3-{5-Cyano-6-[(2,2-dimethyl-propyl)-methyl-amino]-3-fluoro-pyridin-2-ylamino}-N-methoxy-4-methyl-benzamide (a) 3-(3-Cyano-6-chloro-5-fluoro-pyridin-2-ylamino)-N-methoxy-4-methyl-benzamide A mixture of 2,6-dichloro-5-fluoro-nicotinonitrile (830 mg, 4.34 mmol), 3-amino-N-methoxy-4-methyl-benzamide (576 mg, 3.2 mmol) and triethylamine (0.5 mL) in acetonitrile (10 mL) was heated to 70° C. overnight. Then the solvent was removed under reduced pressure and the reaction mixture was partitioned between water and ethyl acetate. The organic layer was dried (sodium sulfate) and concentrated under reduced pressure. The product (220 mg, 21%) was isolated after purification by silica gel chromatography. $C_{15}H_{12}ClFN_4O_2$ MS m/e=335 (M+H).

(b) Synthesis of 3-{5-Cyano-6-[(2,2-dimethyl-propyl)-methyl-amino]-3-fluoro-pyridin-2-ylamino}-N-methoxy-4-methyl-benzamide

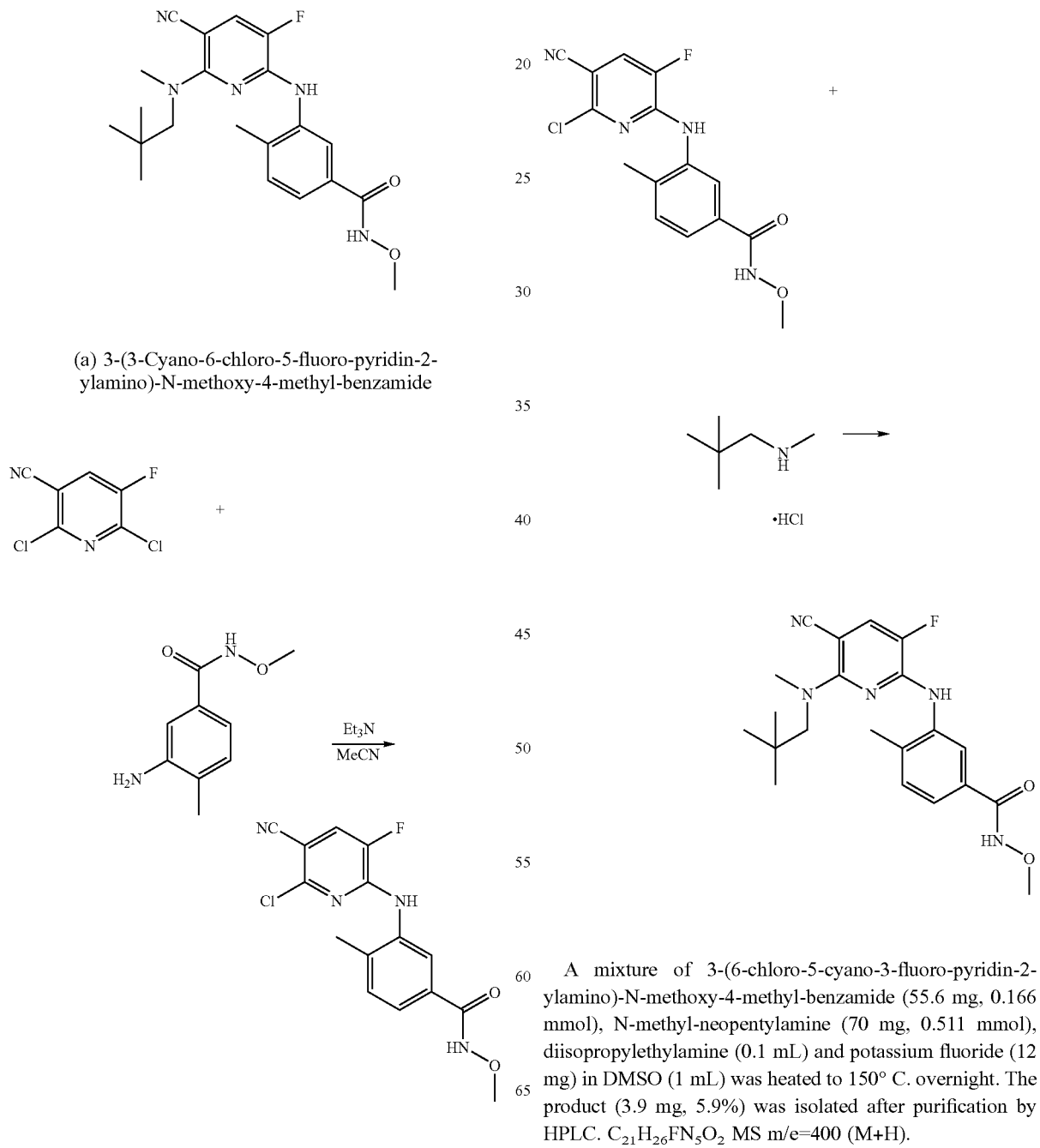

A mixture of 3-(6-chloro-5-cyano-3-fluoro-pyridin-2-ylamino)-N-methoxy-4-methyl-benzamide (55.6 mg, 0.166 mmol), N-methyl-neopentylamine (70 mg, 0.511 mmol), diisopropylethylamine (0.1 mL) and potassium fluoride (12 mg) in DMSO (1 mL) was heated to 150° C. overnight. The product (3.9 mg, 5.9%) was isolated after purification by HPLC. $C_{21}H_{26}FN_5O_2$ MS m/e=400 (M+H).

EXAMPLE 52

Synthesis of 3-{5-Cyano-6-[(2,2-dimethyl-propyl)-methyl-amino]-2-methylsulfanyl-pyrimidin-4-ylamino}-4,N-dimethyl-benzamide

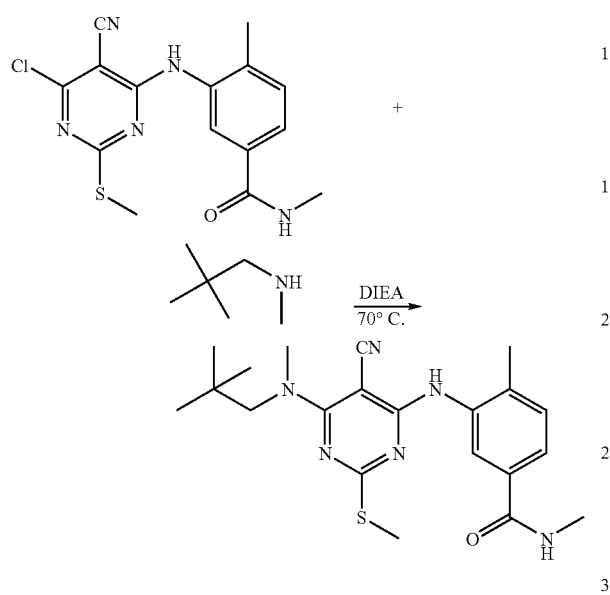

This compound was prepared according to procedure for the synthesis of 3-(6-Chloro-5-cyano-2-methylsulfanyl-pyrimidin-4-ylamino)-4,N-dimethyl-benzamide. MS (m/z): 413 (M+H).

EXAMPLE 21

Synthesis of 3-{5-Cyano-6-[(2,2-dimethyl-propyl)-methyl-amino]-2-methanesulfonyl-pyrimidin-4-ylamino}-4,N-dimethyl-benzamide

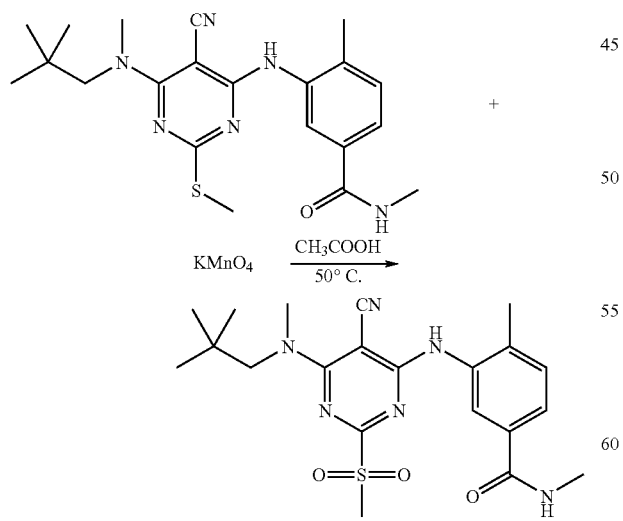

To a solution of 3-{5-cyano-6-[(2,2-dimethyl-propyl)-methyl-amino]-2-methylsulfanyl-pyrimidin-4-ylamino}-4,N-dimethyl-benzamide (0.20 g, 0.48 mmol) in acetic acid (8 mL) was added a solution of potassium permagnate (87 mg, 0.55 mmol) in water (10 mL). The resulting mixture was heated to 50° C. for 10 minutes. The reaction mixture was then diluted with water (20 mL), and the product was extracted with ethyl acetate. The product was obtained (199 mg) after drying and removing the solvent. MS (m/z): 445 (M+H).

EXAMPLE 40

Synthesis of 3-{5-Cyano-6-[(2,2-dimethyl-propyl)-methyl-amino]-2-methylamino-pyrimidin-4-ylamino}-4,N-dimethyl-benzamide

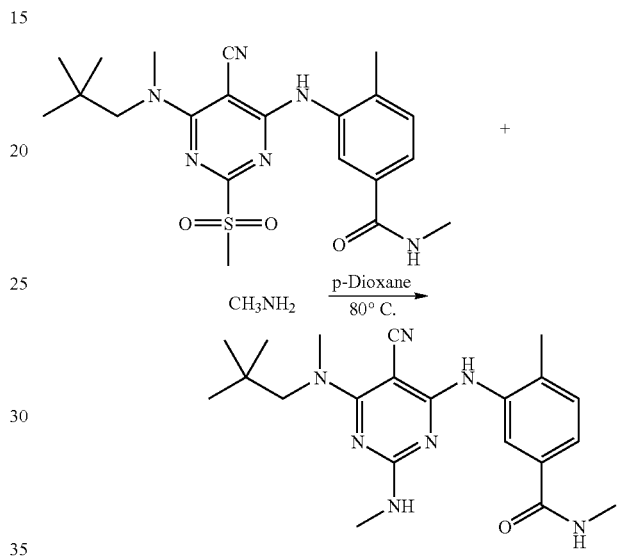

3-{5-Cyano-6-[(2,2-dimethyl-propyl)-methyl-amino]-2-methanesulfonyl-pyrimidin-4-ylamino}-4,N-dimethyl-benzamide (44 mg, 0.1 mmol) and methylamine (1 mL, 1M in THF) were mixed in p-dioxane (1 mL) in a sealed tube. The mixture was heated to 80° C. for overnight. The solvent was removed in vacuo, and the product (23 mg) was purified by the silica gel column chromatography. MS (m/z): 396 (M+H).

EXAMPLE 36

Synthesis of 3-[3-Cyano-2-[(2,2-dimethyl-propyl)-methyl-amino]6-(1-methyl-piperidin-4-yloxy)pyridin-4-ylamino]-4,N-dimethyl-benzamide

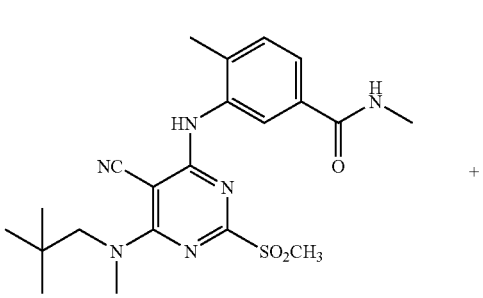

-continued

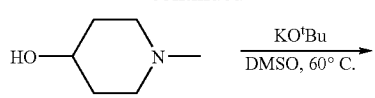

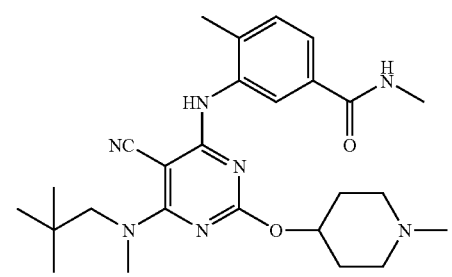

To a portion of 576 mg of 1-methylpiperidine-4-ol (576 mg; 5 mmol) is added 616 mg of potassium tert.-butoxide (5.5 mmol) followed by 4.0 mL of DMSO. After stirring this mixture at r.t. for 1 h a portion of 1.0 mL of this mixture is added at r.t. to 19 mg of 3-{5-cyano-6-[(2,2-dimethyl-propyl)-methyl-amino]-2-methanesulfonyl-pyrimidin-4-ylamino}-4,N-dimethyl-benzamide (0.043 mmol) on 0.2 mL of DMSO. The mixture was heated at 60° C. for 3 h. At r.t. 5 mL of ethyl acetate is added and the organic layer is washed with brine (1×4 mL). The organic layer is dried (MgSO₄), volatiles are removed in vacuo and the product is purified via reversed phase prep. HPLC. (Yield: 18.6 mg; 0.026 mmol; 56%). MS (m/z): 480 (M+H).

EXAMPLE 41

Synthesis of 3-[5-Cyano-6-[(2,2-dimethyl-propyl)-methyl-amino]-2-(4-methyl-[1,4]diazepan-1-yl)-pyrimidin-4-ylamino]-4,N-dimethyl-benzamide

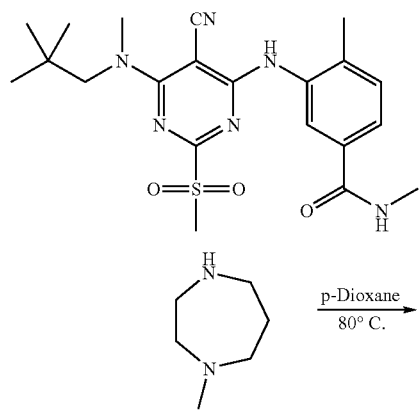

-continued

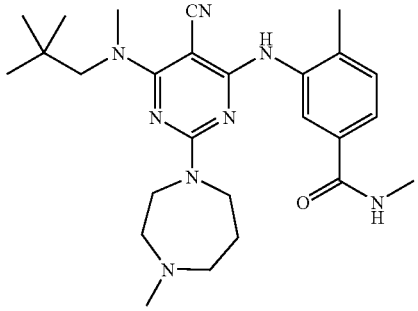

3-[5-Cyano-6-[(2,2-dimethyl-propyl)-methyl-amino]-2-(4-methyl-[1,4]diazepan-1-yl)-pyrimidin-4-ylamino]-4,N-dimethyl-benzamide was synthesized similar to the synthesis of 3-{5-cyano-6-[(2,2-dimethyl-propyl)-methyl-amino]-2-methylamino-pyrimidin-4-ylamino}-4,N-dimethyl-benzamide. MS (m/z): 479 (M+H).

EXAMPLE 42

Synthesis of 3-[5-Cyano-6-[(2,2-dimethyl-propyl)-methyl-amino]-2-(4-methyl-[1,4]diazepan-1-yl)-pyrimidin-4-ylamino]-N-methoxy-4-methyl-benzamide

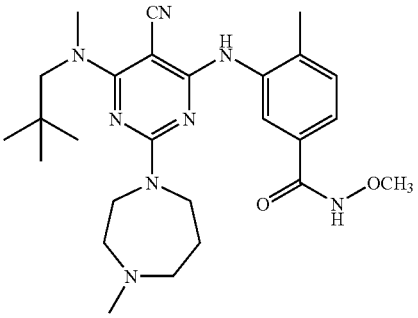

(a) 3-(6-Chloro-5-cyano-2-methylsulfanyl-pyrimidin-4-ylamino)-N-methoxy-4-methyl-benzamide

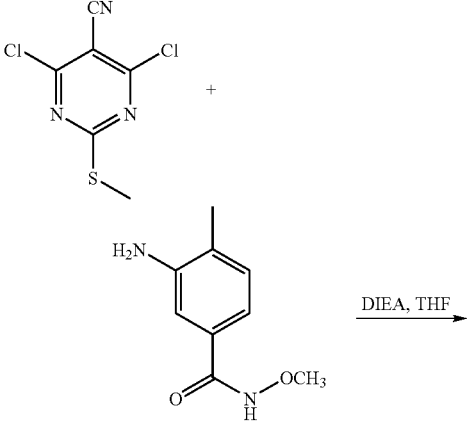

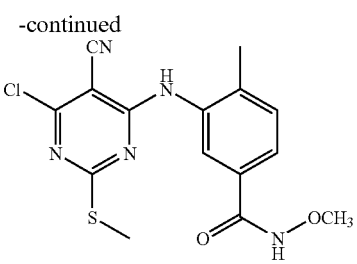

4,6-Dichloro-2-methylsulfanyl-pyrimidine-5-carbonitrile (2.19 g, 10 mmol), 3-amino-N-methoxy-4-methyl-benzamide (1.80 g, 10 mmol) and DIEA (1.9 mL) in THF (80 mL) were stirred at room temperature for overnight. The solvent was removed in vacuo and the product (3.33 g, 92%) was obtained after purification by silica gel column chromatography.

(b) Synthesis of 3-{5-Cyano-6-[(2,2-dimethyl-propyl)-methyl-amino]-2-methylsulfanyl-pyrimidin-4-ylamino}-N-methoxy-4-methyl-benzamide

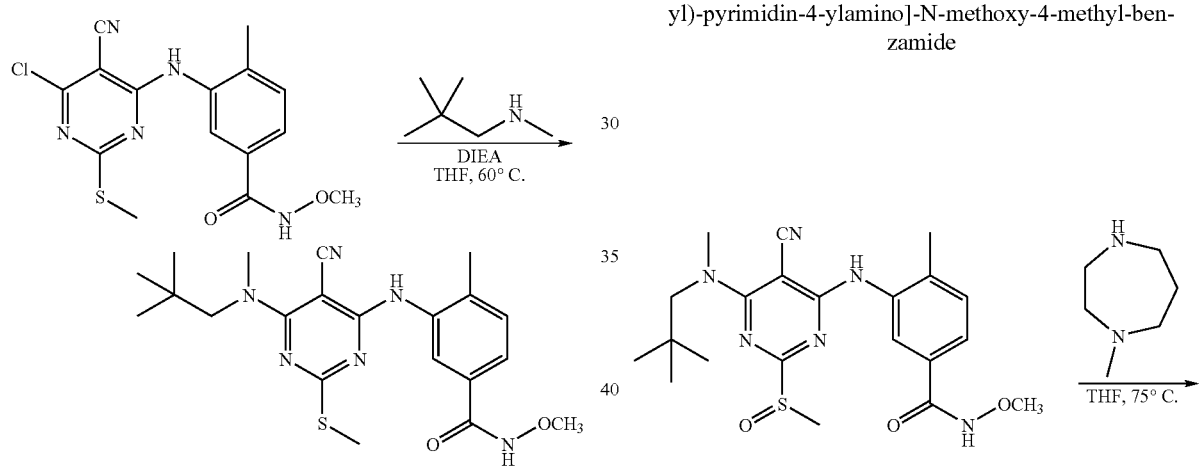

3-(6-Chloro-5-cyano-2-methylsulfanyl-pyrimidin-4-ylamino)-N-methoxy-4-methyl-benzamide (3.33 g, 9.2 mmol), N-methyl-neopentylamine hydrochloride (2.05 g, 15 mmol) and DIEA (3.87 g, 30 mmol) in THF (10 mL) were heated to 60° C. for overnight. The solvent was removed in vacuo and the product (1.75 g) was obtained after purification by silica gel column chromatography.

(c) Synthesis of 3-{5-Cyano-6-[(2,2-dimethyl-propyl)-methyl-amino]-2-methanesulfinyl-pyrimidin-4-ylamino}-N-methoxy-4-methyl-benzamide

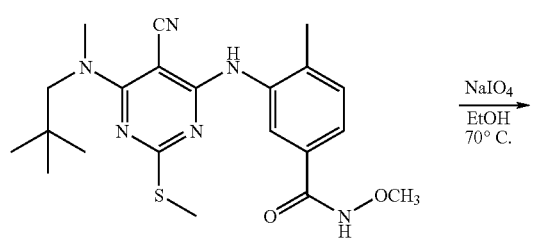

To a solution of 3-{5-Cyano-6-[(2,2-dimethyl-propyl)-methyl-amino]-2-methylsulfanyl-pyrimidin-4-ylamino}-N-methoxy-4-methyl-benzamide (0.10 g) in ethanol (5 mL) was added the solution of sodium periodate (0.2 g) in water (1 mL). The resulting solution was heated to 70° C. for overnight. The solvent was evaporated and the residue was partitioned between water and ethyl acetate. The organic layer was separated, and concentrated, and the residue was purified by silica gel column chromatography to afford the sulfoxide product (90 mg). MS (m/z): 445 (M+H).

(d) Synthesis of 3-[5-Cyano-6-[(2,2-dimethyl-propyl)-methyl-amino]-2-(4-methyl-[1,4]diazepan-1-yl)-pyrimidin-4-ylamino]-N-methoxy-4-methyl-benzamide

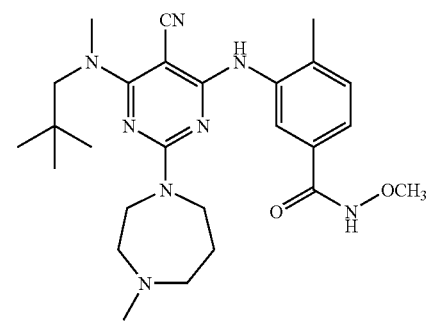

3-{5-Cyano-6-[(2,2-dimethyl-propyl)-methyl-amino]-2-methanesulfinyl-pyrimidin-4-ylamino}-N-methoxy-4-methyl-benzamide (40 mg) and 1-methyl-homopiperazine (0.05 mL) in THF (0.5 mL) were heated in sealed tube at 75° C. for overnight. After the solvent was removed in vacuo, the residue was purified by silica gel column chromatography to afford the product (6.8 mg). MS (m/z): 495 (M+H).

EXAMPLE 32

Synthesis of 3-{5-Cyano-6-[(2,2-dimethyl-propyl)-methyl-amino]-2-methylamino-pyrimidin-4-ylamino}-N-methoxy-4-methyl-benzamide

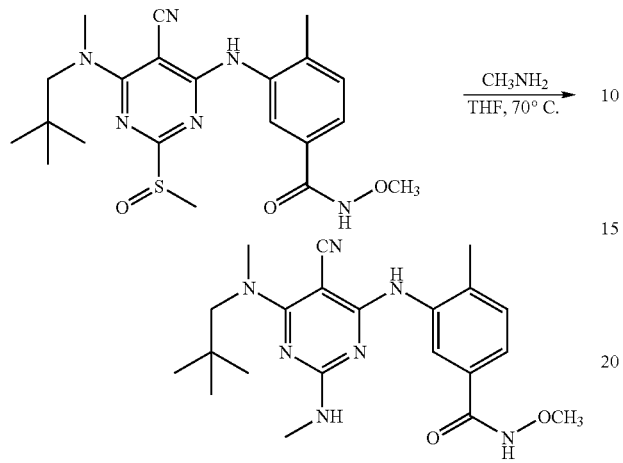

3-{5-Cyano-6-[(2,2-dimethyl-propyl)-methyl-amino]-2-methanesulfinyl-pyrimidin-4-ylamino}-N-methoxy-4-methyl-benzamide (33 mg) and methylamine (2.5 mL, 2 M in THF) were heated in a sealed tube at 75° C. for overnight. After the solvent was removed in vacuo, the residue was purified by silica gel column chromatography to afford the product (7.3 mg). MS (m/z): 412 (M+H).

EXAMPLE 33

Synthesis of 3-[5-Cyano-6-[(2,2-dimethyl-propyl)-methyl-amino]-2-(pyrrolidin-3-ylamino)-pyrimidin-4-ylamino]-N-methoxy-4-methyl-benzamide

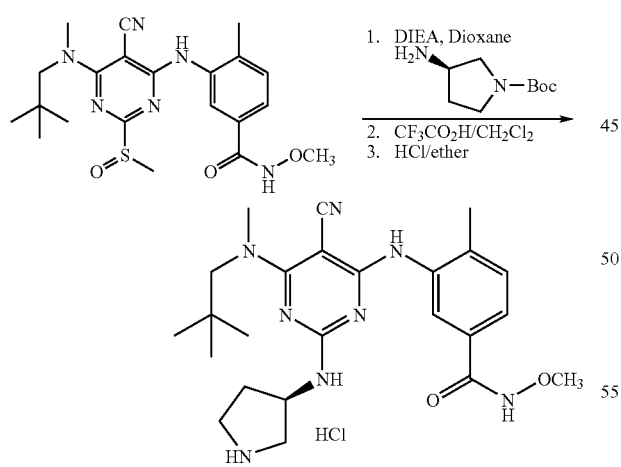

3-{5-Cyano-6-[(2,2-dimethyl-propyl)-methyl-amino]-2-methanesulfinyl-pyrimidin-4-ylamino}-N-methoxy-4-methyl-benzamide (33 mg) and 1-N-Boc-3-(R)-aminopyrrolidine (30 mg), DIEA (0.2 mL) and p-dioxane (2 mL) were heated in a sealed tube at 75° C. for overnight. After the removal of the solvent in vacuo, the product was purified by silica gel column chromatography and treated with TFA/DCM (1:1) in order to remove the Boc-group. The product was then converted to hydrochloride salt by treating it with hydrochloric acid (1 M in ether) (Yield: 20 mg). MS (m/z): 567 (M+H).

EXAMPLE 24

Synthesis of 3-{5-Amino-6-[(2,2-dimethyl-propyl)-methyl-amino]-pyrimidin-4-ylamino}-4,N-dimethyl-benzamide

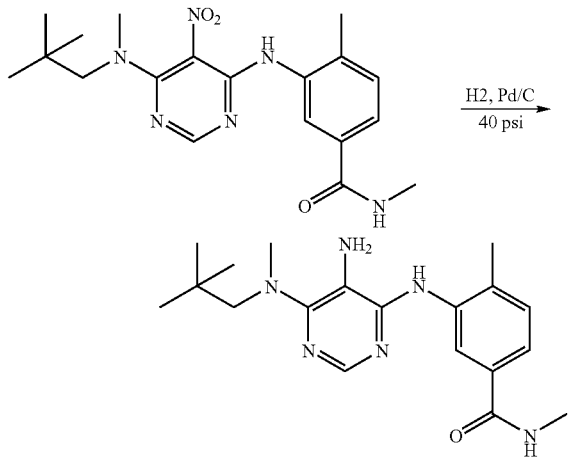

3-{6-[(2,2-Dimethyl-propyl)-methyl-amino]-5-nitro-pyrimidin-4-ylamino}-4,N-dimethyl-benzamide (0.31 g, 0.8 mmol)) was hydrogenated under 40 psi of hydrogen pressure in the presence of 10% Pd/C for 4 hours in Parr instrument. The catalyst was filtered off through celite and the filtrate was concentrated to afford the product (0.24 g, yield 84%). MS (m/z): 357 (M+H).

EXAMPLE 25

Synthesis of 3-{5-(Acetylamino)-6-[(2,2-dimethyl-propyl)-methyl-amino]-pyrimidin-4-ylamino}-4,N-dimethy-l-benzamide

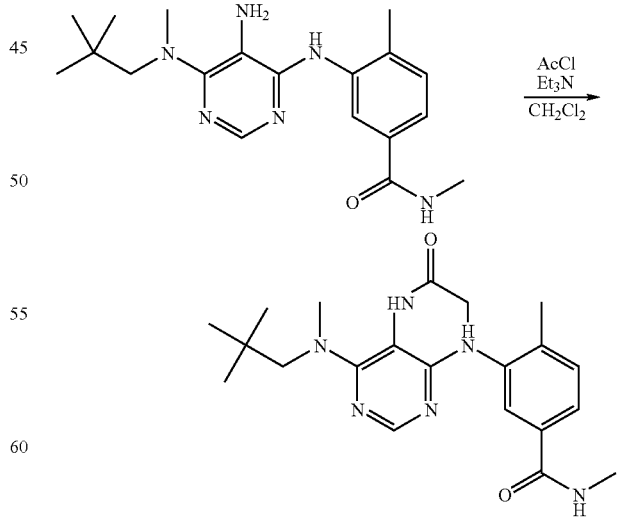

3-{5-Amino-6-[(2,2-dimethyl-propyl)-methyl-amino]-pyrimidin-4-ylamino}-4,N-dimethyl-benzamide (16 mg), acetyl chloride (3.5 mg), triethylamine (0.02 ml) were stirred in methylene chloride (0.2 mL) at room temperature for overnight. The product (2.8 mg) was purified by preparative thin layer chromatography. MS (m/z): 399 (M+H).

EXAMPLE 14

Synthesis of 3-{5-Bromo-6-[(2,2-dimethyl-propyl)-methyl-amino]-2-methylsulfanyl-pyrimidin-4-ylamino}-4,N-dimethyl-benzamide

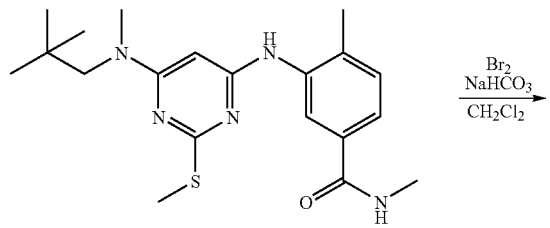

To a solution of 3-{6-[(2,2-dimethyl-propyl)-methyl-amino]-2-methylsulfanyl-pyrimidin-4-ylamino}-4,N-dimethyl-benzamide (0.10 g) in methylene chloride (2 mL), was added sat. aq. sodium bicarbonate (0.05 mL) and bromine (0.013 mL). The resulting mixture was stirred at room temperature for 30 minutes, and ethyl acetate (30 mL) and magnesium sulfate (1 g) was added. After filtration and concentration, the residue was purified by silica gel column chromatography to afford the product (61.9 mg). MS (m/z): 466 (M+H).

EXAMPLE 15

Synthesis of 3-{5-Bromo-6-[(2,2-dimethyl-propyl)-methyl-amino]-2-methylamino-pyrimidin-4-ylamino}-4,N-dimethyl-benzamide

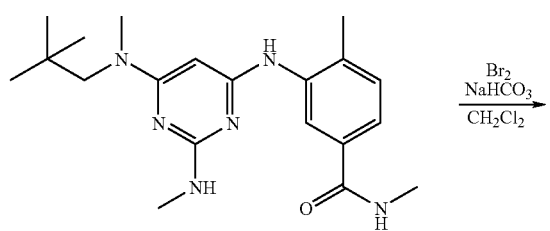

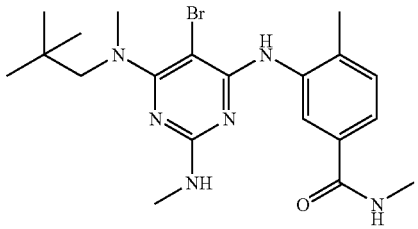

3-{6-[(2,2-Dimethyl-propyl)-methyl-amino]-2-methylamino-pyrimidin-4-ylamino}-4,N-dimethyl-benzamide (33 mg), aq. sat. sodium bicarbonate (0.05 mL) and bromine (14 mg) were stirred in methylene chloride (1 mL) at room temperature for 4 hours. The product (14 mg) was purified with preparative thin layer chromatography. MS (m/z): 449 (M+1).

EXAMPLE 11

Synthesis of 3-[5-Bromo-6-(2,2-dimethyl-propylamino)-2-methylamino-pyrimidin-4-ylamino]-4,N-dimethyl-benzamide

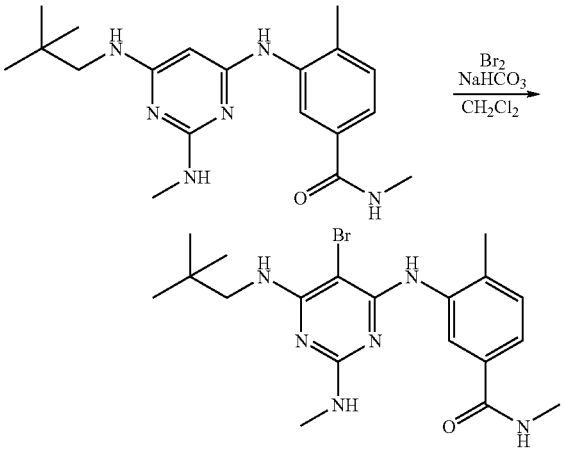

3-[6-(2,2-Dimethyl-propylamino)-2-methylamino-pyrimidin-4-ylamino]-4,N-dimethyl-benzamide (35 mg), aq. sat. sodium bicarbonate (0.05 mL) and bromine (21 mg) were stirred in methylene chloride (1 mL) at room temperature for overnight. The product (4 mg) was purified with preparative thin layer chromatography. MS (m/z): 435 (M+H).

EXAMPLE 49

Synthesis of 3-{5-Bromo-6-[(2,2-dimethyl-propyl)-amino]-pyrimidin-4-ylamino}-4,N-dimethyl-benzamide

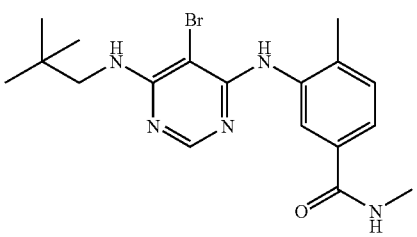

(a) 3-(6-Chloro-pyrimidin-4-ylamino)-4,N-dimethyl-benzamide

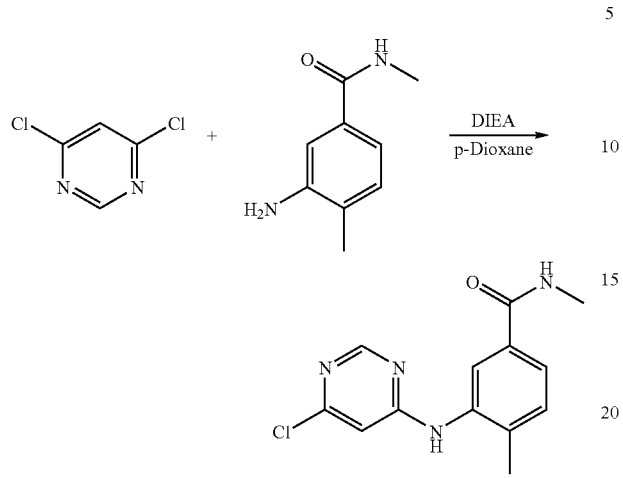

To a solution of 4,6-dichloropyrimidine (2.0 g, 13.4 mmol) in p-dioxane (50 mL), 3-amino-4,N-dimethyl-benzamide (3.0 g, 18.3 mmol) and DIEA (2.3 mL) were added. The resulting mixture was heated to reflux for 4 days. The solvent was removed in vacuo, the residue was taken in water and ethyl acetate, and the ethyl acetate layer was separated and concentrated. The product was purified by silica gel column chromatography using ethyl acetate:hexane (1:1) as eluent to afford the pale white solid product (1.6 g, yield 43%). MS (m/z): 277 (M+H).

(b) Synthesis of 3-[6-(2,2-Dimethyl-propylamino)-pyrimidin-4-ylamino]-4,N-dimethyl-benzamide

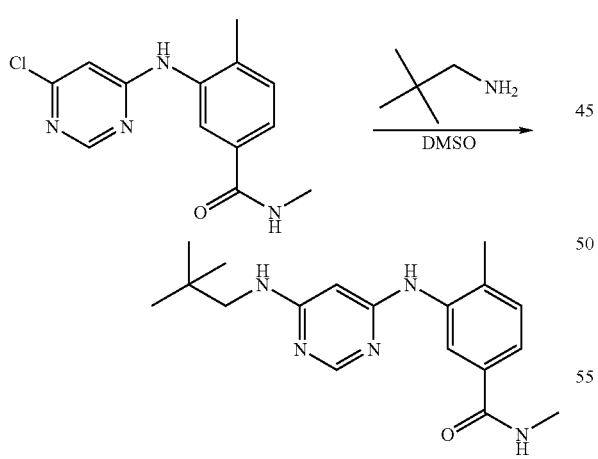

To a solution of 3-(6-chloro-pyrimidin-4-ylamino)-4,N-dimethyl-benzamide (0.4 g, 1.44 mmol) in DMSO (3 mL), neopentylamine (0.4 mL, 3.39 mmol) was added. The resulting solution was heated at 110° C. for 4 days. The product was purified by silica gel column chromatography using ethyl acetate as eluent to afford the product (0.45 g, yield 99%). MS (m/z): 328 (M+H).

(c) Synthesis of 3-{5-Bromo-6-[(2,2-dimethyl-propyl)-amino]-pyrimidin-4-ylamino}-4,N-dimethyl-benzamide

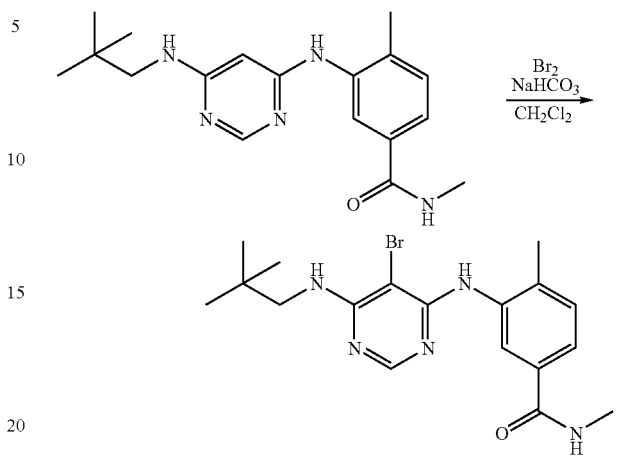

To a solution of 3-{6-[(2,2-dimethyl-propyl)-amino]-pyrimidin-4-ylamino}-4,N-dimethyl-benzamide (0.45 g, 1.37 mmol) in methylene chloride (10 mL), was added sat. aq. sodium bicarbonate (2 mL) and bromine (0.07 mL, 1.37 mmol). The resulting mixture was stirred at room temperature for 18 hours, and the reaction was then diluted with water (20 mL). The organic layer was separated and the aqueous layer was extracted with DCM (10 mL). The combined organic layer was dried (sodium sulfate), filtered and concentrated. The residue was purified by silica gel column chromatography using 2% methanol in DCM as eluent to afford the product (314 mg, yield 56%). MS (m/z): 406 (M+H).

EXAMPLE 2
Synthesis of 3-{5-Bromo-6-[(2,2-dimethyl-propyl)-methyl-amino]-pyrimidin-4-ylamino}-4,N-dimethyl-benzamide

(a) 3-(6-Chloro-pyrimidin-4-ylamino)-4,N-dimethyl-benzamide

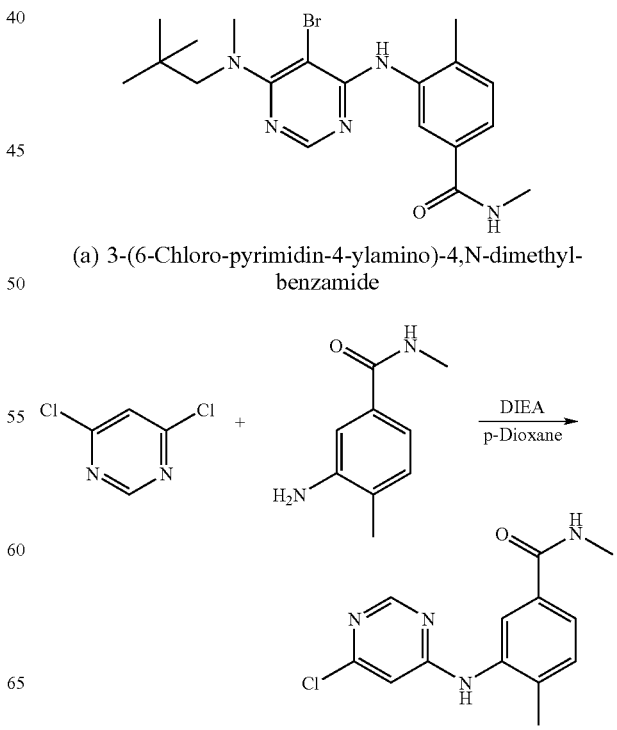

To a solution of 4,6-dichloropyrimidine (2.0 g, 13.4 mmol) in p-dioxane (50 mL), 3-amino-4,N-dimethyl-benzamide (3.0 g, 18.3 mmol) and DIEA (2.3 mL) were added. The resulting mixture was heated to reflux for 4 days. The solvent was removed in vacuo, the residue was taken in water and ethyl acetate, and the ethyl acetate layer was separated and concentrated. The product was purified by silica gel column chromatography using ethyl acetate:hexane (1:1) as eluent to afford the pale white solid product (1.6 g, yield 43%). MS (m/z): 277 (M+H).

(b) Synthesis of 3-{6-[(2,2-dimethyl-propyl)-methyl-amino]-pyrimidin-4-ylamino}-4,N-dimethyl-benzamide

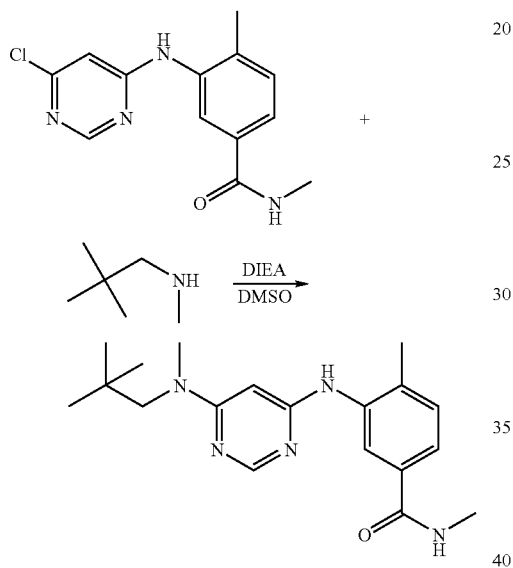

To a solution of 3-(6-chloro-pyrimidin-4-ylamino)-4,N-dimethyl-benzamide (0.4 g, 1.44 mmol) in DMSO (3 mL), N-methylneopentylamine hydrochloride (0.4 g, 2.9 mmol) and DIEA (0.5 mL, 2.9 mmol) were added. The resulting solution was heated at 110° C. for 4 days. The product was purified by silica gel column chromatography using ethyl acetate as eluent to afford the product (0.46 g, yield 99%). MS (m/z): 342 (M+H).

(c) Synthesis of 3-{5-Bromo-6-[(2,2-dimethyl-propyl)-methyl-amino]-pyrimidin-4-ylamino}-4,N-dimethyl-benzamide

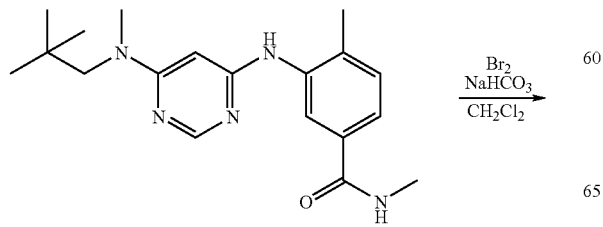

-continued

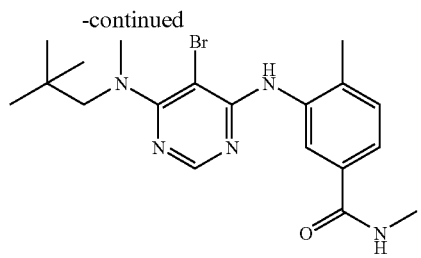

To a solution of 3-{6-[(2,2-dimethyl-propyl)-methyl-amino]-pyrimidin-4-ylamino}-4,N-dimethyl-benzamide (0.46 g, 1.34 mmol) in methylene chloride (10 mL), was added sat. aq. sodium bicarbonate (2 mL) and bromine (0.07 mL, 1.37 mmol). The resulting mixture was stirred at room temperature for 18 hours, and the reaction was then diluted with water (20 mL). The organic layer was separated and the aqueous layer was extracted with DCM (10 mL). The combined organic layer was dried (sodium sulfate), filtered and concentrated. The residue was purified by silica gel column chromatography using 2% methanol in DCM as eluent to afford the product (250 mg, yield 44%). MS (m/z): 420 (M+H).

EXAMPLE 74

Synthesis of 3-(R)-[5-Cyano-6-[(2,2-dimethyl-propyl)-methyl-amino]-2-(pyrrolidin-3-ylamino)-pyrimidin-4-ylamino]-4-N-dimethyl-benzamide

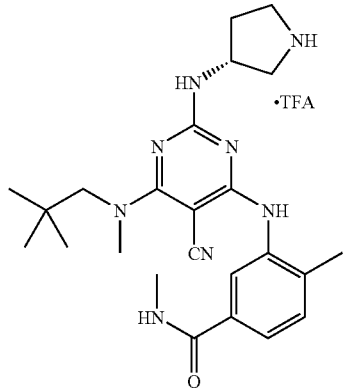

(a) 3-(R)-[4-[(2,2-Dimethyl-propyl)-methyl-amino]-6-(2-methyl-5-methylcarbamoyl-phenylamino)-pyrimidin-2-ylamino]-pyrrolidine-1-carboxylic acid tert-butyl ester

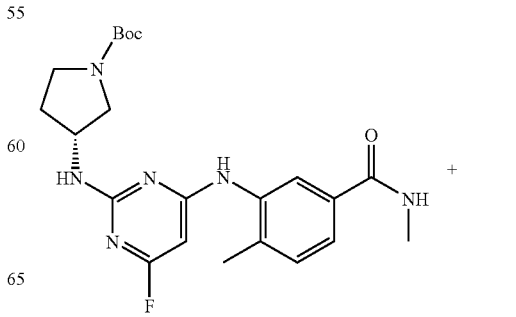

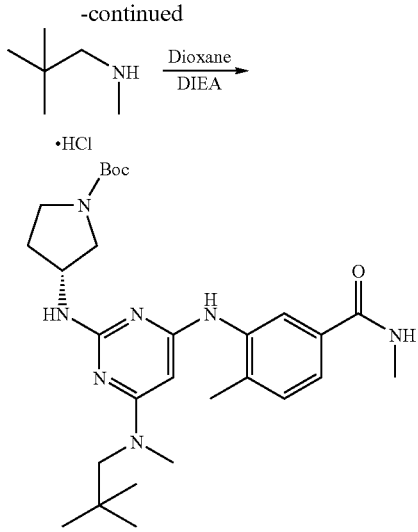

A mixture of 3-(R)-[4-fluoro-6-(2-methyl-5-methylcarbamoyl-phenylamino)-pyrimidin-2-ylamino]-pyrrolidine-1-carboxylic acid tert-butyl ester (0.36 g, 0.81 mmol), N-methyl-neopentylamine hydrochloride (411 mg, 3 mmol) and DIEA(0.4 mL) in 1,4-dioxane (0.5 mL) was stirred at 90° C. overnight. After removing the solvent under reduced pressure the desired product (81 mg) was purified by silica gel chromatography. $C_{28}H_{43}N_7O_3$ MS m/e=526 (M+H).

(b) Synthesis of 3-(R)-[5-Cyano-6-[(2,2-dimethyl-propyl)-methyl-amino]-2-(pyrrolidin-3-ylamino)-pyrimidin-4-

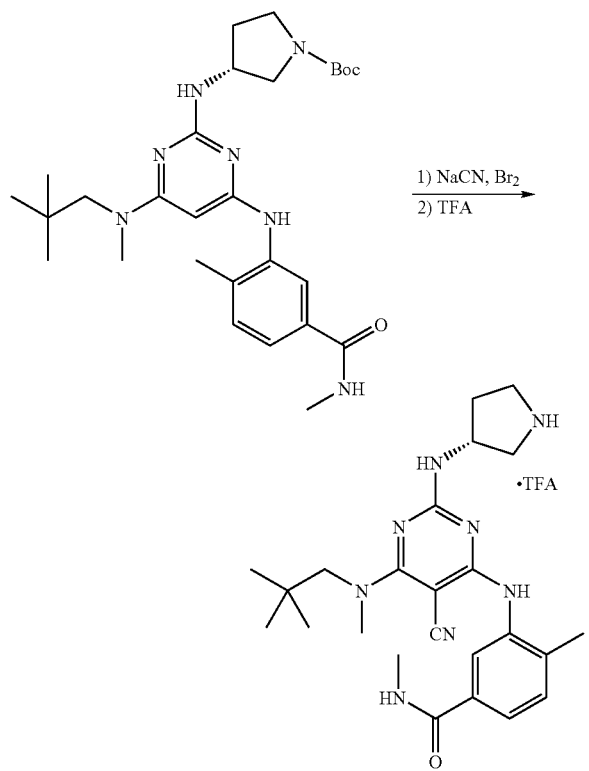

To a mixture of 3-(R)-[4-[(2,2-dimethyl-propyl)-methyl-amino]-6-(2-methyl-5-methylcarbamoyl-phenylamino)-pyrimidin-2-ylamino]-pyrrolidine-1-carboxylic acid tert-butyl ester (70 mg, 0.0001 mmol) and sodium cyanide (0.044 g, 0.89 mmol) in sat. aq. sodium bicarbonate (1 mL) and methylene chloride (3 mL) at room temp was added bromine (0.045 mL, 0.87 mmol). The resulting mixture was stirred for 16 h at room temp, then diluted with water and extracted with methylene chloride (2×15 mL). The combined organic layer was dried (sodium sulfate), filtered and concentrated under reduced pressure. This product was then treated with a mixture of trifluoroacetic acid and methylene chloride (1:1 v/v, 1 mL). The resulting solution was stirred at room temp for 2 h, then the solvent was removed under reduced pressure and the product was purified by HPLC. $C_{24}H_{34}N_8O$ MS m/e=451 (M+H).

EXAMPLE 75

Synthesis of 3-(R)-[5-Cyano-4-[(2,2-dimethyl-propyl)-methyl-amino]-6-(pyrrolidin-3-ylamino)-pyrimidin-2-ylamino]-4-N-dimethyl-benzamide

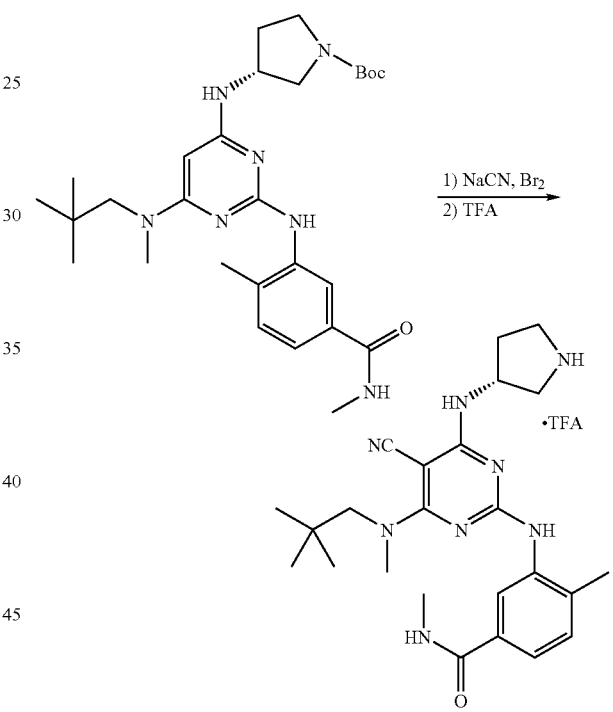

To a mixture of 3-(R)-[6-[(2,2-dimethyl-propyl)-methyl-amino]-2-(2-methyl-5-methylcarbamoyl-phenylamino)-pyrimidin-4-ylamino]-pyrrolidine-1-carboxylic acid tert-butyl ester (128 mg, 0.0002 mmol) and sodium cyanide (0.044 g, 0.89 mmol) in sat. aq. sodium bicarbonate (1 mL) and methylene chloride (3 mL) was added bromine (0.045 mL, 0.87 mmol). The resulting mixture was continued stirring at room temp for 16 h, then diluted with water and extracted with methylene chloride (2×15 mL). The combined organic layer was dried (sodium sulfate), filtered and concentrated under reduced pressure. This product was then treated with a mixture of trifluoroacetic acid and methylene chloride (1:1 v/v, 1 mL). The resulting solution was stirred at room temp for 2 h. The solvent was removed under reduced pressure, and the product was purified by HPLC. $C_{24}H_{34}N_8O$ MS m/e=451 (M+H).

EXAMPLE 62

Synthesis of 3-[5-Cyano-4-[(2,2-dimethyl-propyl)-methyl-amino]-6-(4-methyl-[1,4]diazepan-1-yl)-pyrimidin-2-ylamino]-N-methoxy-4-methyl-benzamide

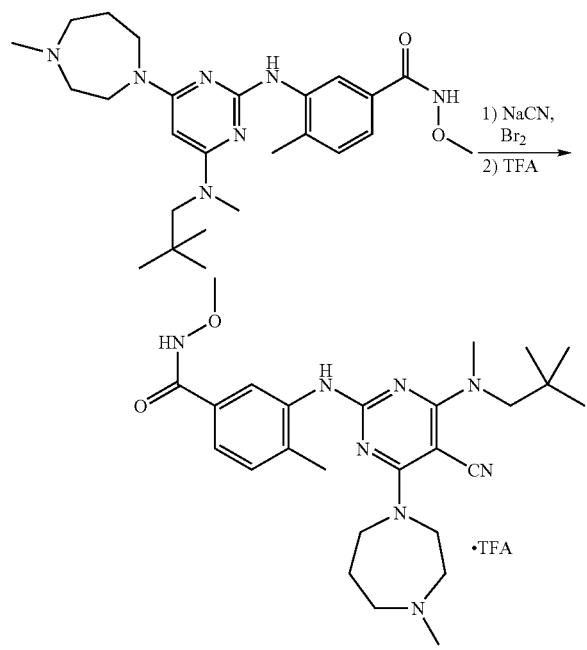

To a stirred mixture of 3-[4-[(2,2-dimethyl-propyl)-methyl-amino]-6-(4-methyl-[1,4]diazepan-1-yl)-pyrimidin-2-ylamino]-N-methoxy-4-methyl-benzamide (140 mg, 0.29 mmol) and sodium cyanide (0.044 g, 0.89 mmol) in sat. aq. sodium-bicarbonate (1 mL) and methylene chloride (3 mL) was added bromine (0.045 mL, 0.87 mmol). The resulting mixture was stirred for 16 h at room temp, then diluted with water and extracted with methylene chloride (2×15 mL). The combined organic layer was dried (sodium sulfate), filtered and concentrated under reduced pressure, and the product was purified by HPLC. $C_{26}H_{38}N_8O_2$ MS m/e=495 (M+H). Deprotection was performed as described in Example 75.

EXAMPLE 61

Synthesis of 3-[5-Cyano-2-[(2,2-dimethyl-propyl)-methyl-amino]-6-(4-methyl-[1,4]diazepan-1-yl)-pyrimidin-4-ylamino]-N-ethoxy-4-methyl-benzamide

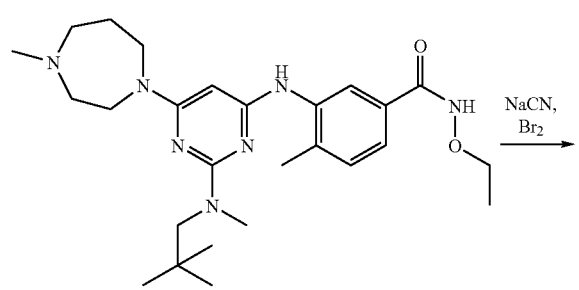

-continued

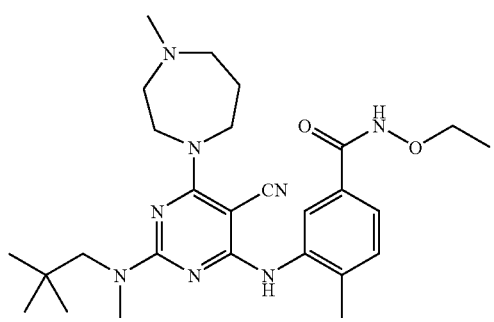

To a stirred mixture of 3-[2-[(2,2-dimethyl-propyl)-methyl-amino]-6-(4-methyl-[1,4]diazepan-1-yl)-pyrimidin-4-ylamino]-N-ethoxy-4-methyl-benzamide (50 mg, 0.1 mmol) and sodium cyanide (0.044 g, 0.89 mmol) in sat. aq. sodium bicarbonate (1 mL) and methylene chloride (3 mL) was added at room temp bromine (0.045 mL, 0.87 mmol). The resulting mixture was continued stirring for 16 h at room temp. The reaction mixture was diluted with water and extracted with methylene chloride (2×15 mL). The combined organic layer was dried (sodium sulfate), filtered and concentrated under reduced pressure, and the product was purified by HPLC. $C_{27}H_{40}N_8O_2$ MS m/e=509 (M+H).

EXAMPLE 43

Synthesis of 4-[(2,2-Dimethyl-propyl)-methyl-amino]-6-[2-methyl-5-(4H-[1,2,4]triazol-3-yl)-phenylamino]-2-(pyrrolidin-3(R)-ylamino)-pyrimidine-5-carbonitrile

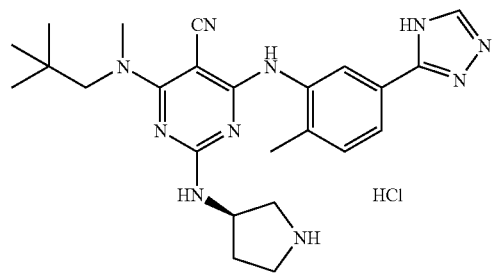

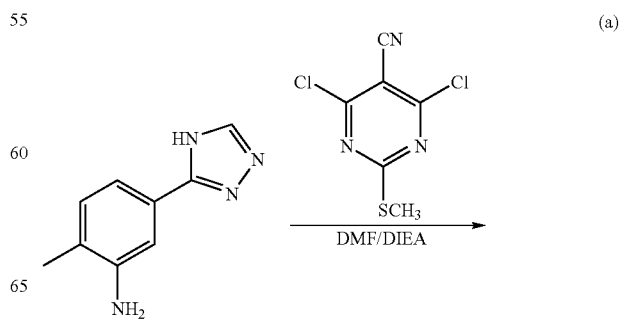

(a)

-continued

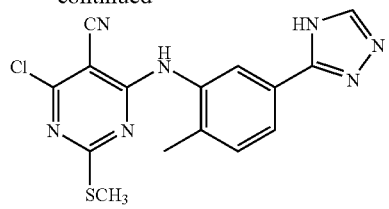

To a solution of 2-methyl-5-(4H-[1,2,4]triazol-3-yl)-phenylamine (174 mg, 1 mmol) in 4 mL of DMF was added 0.17 mL of diisopropylethylamine (1 mmol) and 4,6-dichloro-2-methylsulfanyl-pyrimidine-5-carbonitrile (219 mg, 1 mmol). The resulting solution was stirred at room temperature overnight, then partitioned between ethyl acetate and water. The organic layer was washed with water, brine and dried over MgSO$_4$. Removal of volatiles in vacuo and purification by flash chromatography gave 78 mg of the product (Yield: 22%). MS (m/z) calcd for $C_{15}H_{12}ClN_7S$ (MH+), 358.1, found, 358.3.

(b)

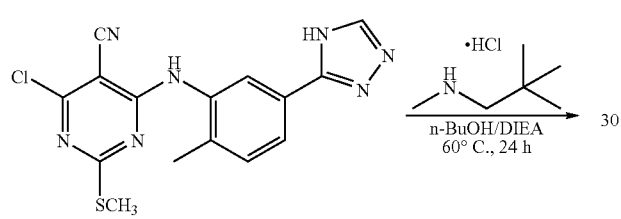

To a solution of 4-chloro-2-methylsulfanyl-6-[2-methyl-5-(4H-[1,2,4]triazol-3-yl)-phenylamino]-pyrimidine-5-carbonitrile (71 mg, 0.2 mmol) in 2 mL of n-BuOH was added 137 mg of N-(2,2-dimethylpropyl)methyl amine HCl salt (1 mmol) and 0.17 mL of diisopropylethylamine (1 mmol) and the resulting solution was stirred at 60° C. for 24 h. Removal of volatiles in vacuo and purification by flash chromatography gave 68 mg of the product (Yield: 81%) MS (m/z) calcd for $C_{21}H_{26}N_8S$ (MH+), 423.2, found, 423.3.

(c)

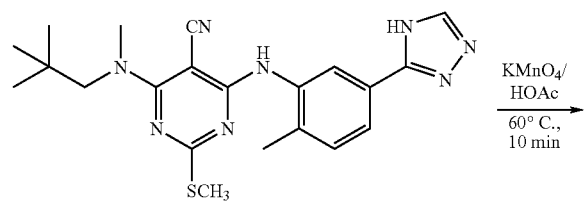

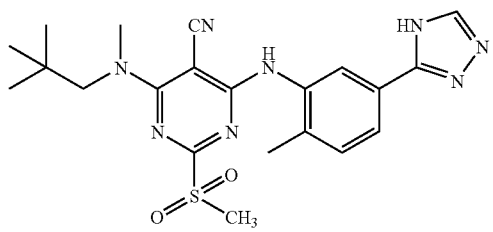

To a solution of 4-[(2,2-dimethyl-propyl)-methyl-amino]-2-methylsulfanyl-6-[2-methyl-5-(4H-[1,2,4]triazol-3-yl)-phenylamino]-pyrimidine-5-carbonitrile (76 mg, 0.18 mmol) in 3 mL of acetic acid was added 0.5 mL water followed by 50 mg of potassium permanganate (0.36 mmol). This solution was stirred at 60° C. for 10 minutes, then diluted with water and extracted with ethyl acetate. The organic layer was washed with water, brine and dried over MgSO$_4$. Removal of volatiles in vacuo gave 58 mg of the crude product which was used in the next step without further purification (Yield: 71%). MS (m/z) calcd for $C_{21}H_{26}N_8O_2S$ (MH+), 455.2, found, 455.3.

(d)

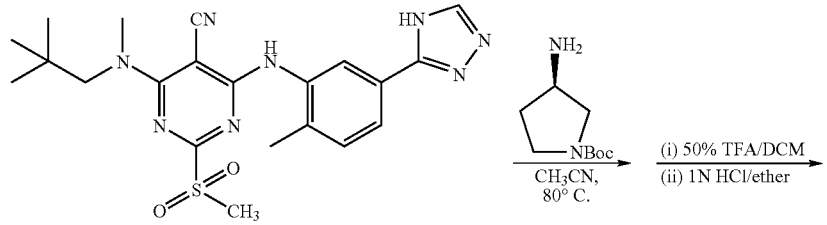

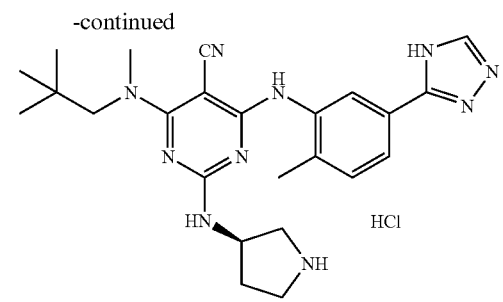

A solution of 4-[(2,2-dimethyl-propyl)-methyl-amino]-2-methanesulfonyl-6-[2-methyl-5-(4H-[1,2,4]triazol-3-yl)-phenylamino]-pyrimidine-5-carbonitrile (10 mg, 0.022 mmol) and 1-tert-butoxycarbony-3(R)-amino-pyrrolidine (0.08 g, 0.4 mmol) in 2 mL of acetonitrile was heated with stirring at 80° C. for 18 h. Volatiles were the removed in vacuo and the product was purified by flash chromatography.

This purified product was then dissolved in 3 mL of a solution of 50% TFA in CH$_2$Cl$_2$ (v/v) and stirred at room temp for 30 min. Removal of volatiles in vacuo and purification via prep. HPLC gave the product as TFA salt. The purified product was then dissolved in 1N HCl (g) in diethyl ether and evaporated to give 0.8 mg of the final product. (Yield: 8%). MS (m/z) calcd for C$_{24}$H$_{32}$N$_{10}$ (MH+), 461.3, found, 461.4.

EXAMPLE 17

Synthesis of 4-[(2,2-Dimethyl-propyl)-methyl-amino]-6-[2-methyl-5-(4H-[1,2,4]triazol-3-yl)-phenylamino]-pyrimidine-5-carbonitrile

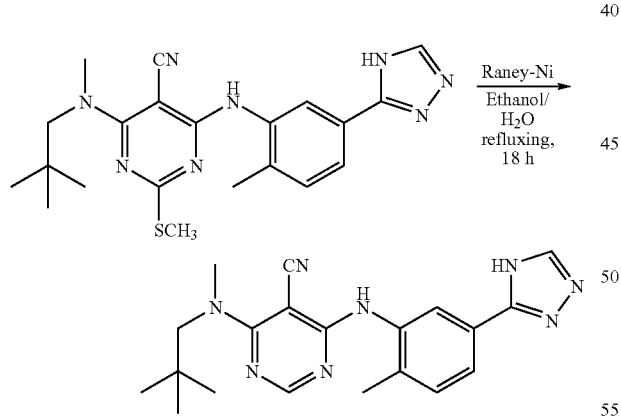

To a solution of 4-[(2,2-dimethyl-propyl)-methyl-amino]-2-methylsulfanyl-6-[2-methyl-5-(4H-[1,2,4]triazol-3-yl)-phenylamino]-pyrimidine-5-carbonitrile (60 mg, 0.142 mmol) in 3 mL of 50% ethanol/water (v/v) was added 0.4 mL of 50% Raney-Ni in water solution. The solution was refluxed under argon for 18 hours. The solution was evaporated under vacuum. The resulting residue was purified by flash chromatography to afford 5.6 mg of the final product (Yield: 10%). MS (m/z) calcd for C$_{20}$H$_{24}$N$_8$ (MH+), 377.2, found, 377.4.

EXAMPLE 80

Synthesis of 3-{5-Bromo-2-[2,2-dimethyl-propyl)-methyl-amino]-pyrimidin-4-ylamino}-4,N-dimethyl-benzamide

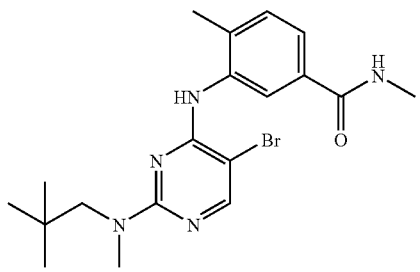

(a) 3-(5-Bromo-2-chloro-pyrimidin-4-ylamino)-4,N-dimethyl-benzamide

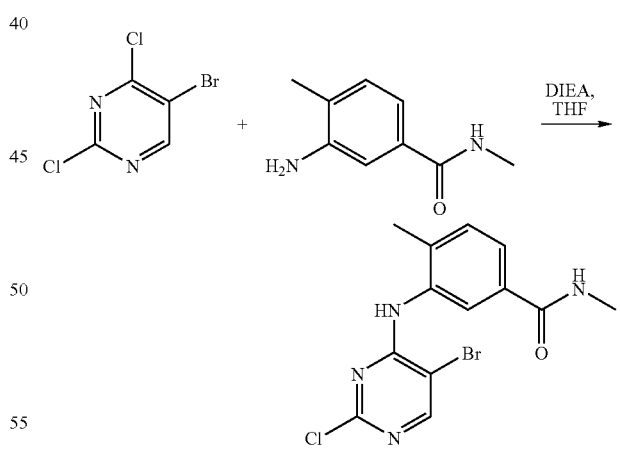

To a solution of 0.38 mL of 5-Bromo-2,4-dichloropyrimidine (70 mg; 3.1 mmol) in 5 mL of THF at 0° C. is added dropwise a solution of 0.644 mL of N,N-diisopropylethylamine (478 mg; 3.7 mmol) and of 506 mg of 3-Amino-4,N-dimethyl-benzamide ((3.1 mmol) in 2 mL of THF. This solution is continued stirring at 0° C. for 1 h, then at 25° C. for 30 min. After removal of volatiles in vacuo the product was purified via silica gel chromatography (20% ethyl acetate in hexanes) to yield 304 mg of a white powder (0.85 mmol; 25% yield). MS (m/z): 355 (M+H).

(b) Synthesis of 3-{5-Bromo-2-[2,2-dimethyl-propyl)-methyl-amino]-pyrimidin-4-ylamino}-4,N-dimethyl-benzamide

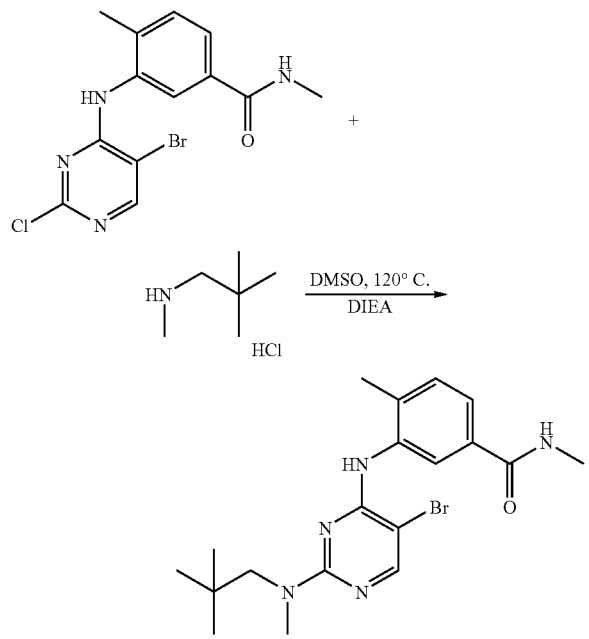

A mixture of 51 mg of 3-(5-Bromo-2-chloro-pyrimidin-4-ylamino)-4,N-dimethyl-benzamide (0.143 mmol), 59 mg of (2,2-dimethylpropyl)-methylamine, hydrochloride (0.430 mmol) and 0.112 mL of N,N-diisopropylethylamine (83 mg; 0.645 mmol) is heated to 120° C. for 18 h, then allowed to cool to r.t. 5 ml of ethyl acetate are added and the organic layer is washed with brine (1×5 ml). The aqueous layer is extracted with ethyl acetate (3×5 ml) and the combined organic layers are dried (MgSO$_4$). After removal of volatiles in vacuo the product was purified via silica gel chromatography (20% ethyl acetate in hexanes) to yield 41 mg of an colorless oil (0.097 mmol; yield: 68%). MS (m/z): 420 (M+H).

EXAMPLE 4

Synthesis of 3-[5-Bromo-2-(pyrrolidin-3(R)-(ylamino)-pyrimidin-4-ylamino]-4,N-dimethyl-benzamide

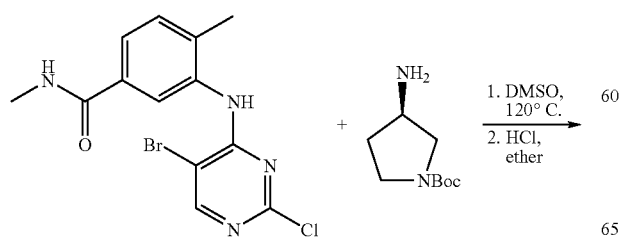

-continued

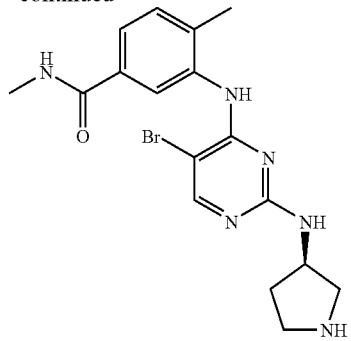

A solution of 22 mg of 3-(5-bromo-2-chloro-pyrimidin-4-ylamino)-4,N-dimethyl-benzamide (0.06 mmol) and 46 mg of 3-amino-pyrrolidine-1-carboxylic acid tert.-butyl ester (0.247 mmol) is heated at 120° C. in 0.3 mL DMSO for 3 d. After addition of 5 mL of ethyl acetate at r.t. the organic layer is washed with a sat. solution of NaHCO$_3$ in water (3×4 mL). The organic layer is dried (MgSO$_4$), volatiles are removed in vacuo and the product is purified via prep. HPLC. (Yield: 5.7 mg; 0.013 mmol; 22 MS (m/z): 444 (M$^+$); 455 (M+Na).

The purified product is dissolved in 1 mL of MeOH and 3 mL of a 1N solution of HCl in diethyl ether is added. The resulting solution is stirred at r.t for 30 min, then volatiles are removed in vacuo and the product is purified via prep. HPLC. (Yield: 4.3 mg; 0.0002 mmol; 0.4%). MS (m/z): 405 (M+H).

EXAMPLE 3

Synthesis of 3-[Bromo-2-(1-methyl-piperidin-4-yloxy)-pyrimidin-4-ylamino]4,N-dimethylbenzamide

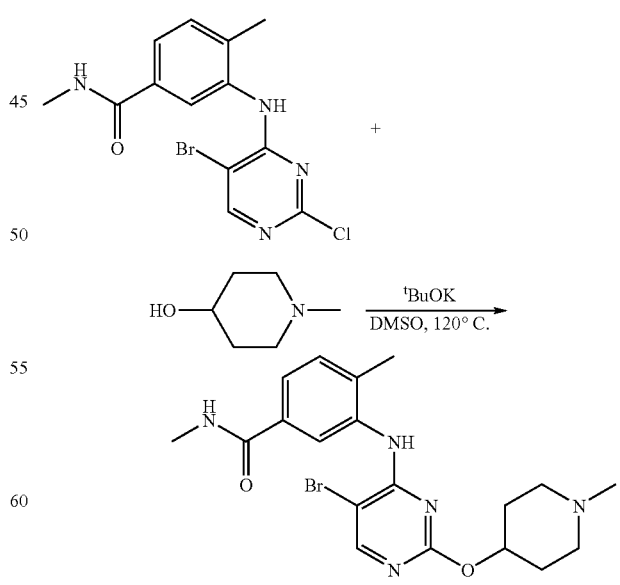

To a portion of 576 mg of 1-methylpiperidine-4-ol (576 mg; 5 mmol) is added 616 mg of potassium tert.-butoxide (5.5 mmol) followed by 4.0 mL of DMSO. After stirring this mixture at r.t. for 1 h a portion of 1.0 mL of this mixture is added at r.t. to 21 mg of 3-(5-Bromo-2-chloro-pyrimidin-4-ylamino)-4,N-dimethyl-benzamide (0.06 mmol). The resulting mixture is heated at 120° C. for 18 h and then allowed to cool to r.t. A portion of 5 mL of ethyl acetate is added and the resulting solution is washed with a sat. solution of NaHCO3 in water (3×4 mL). The organic layer is dried (MgSO₄), volatiles are removed in vacuo and the product is purified via prep. HPLC. (Yield: 5.7 mg; 0.013 mmol; 22%). MS (m/z): 444 (M⁺); 455 (M+Na).

EXAMPLE 53

Synthesis of 3-{5-Cyano-2-[2,2-dimethyl-propyl)-methyl-amino]-pyrimidin-4-ylamino}-4,N-dimethyl-benzamide

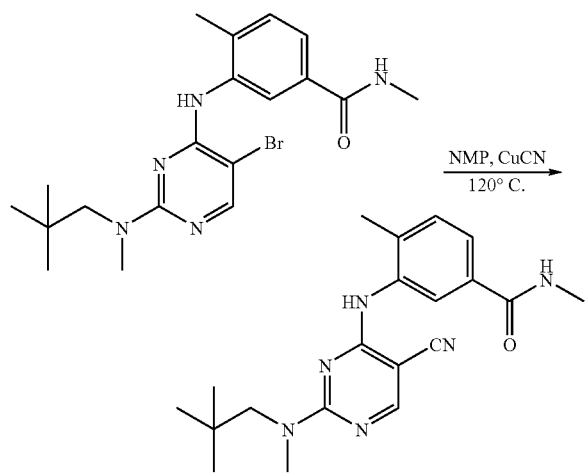

A mixture of 15 mg of 3-{5-Bromo-2-[2,2-dimethyl-propyl)-methyl-amino]-pyrimidin-4-ylamino}-4,N-dimethyl-benzamide (0.036 mmol) and 100 mg of CuCN (1.12 mmol) in 1.0 mL of 1-methyl-2-pyrrolidinone is heated to 140° C. for 18 h. The mixture was allowed to cool to r.t. and 2.0 mL of MeOH were added. After removing the precipitate by filtration volatiles were evaporated and the product was purified by prep. HPCL. Yield: 1.7 mg (0.005 mmol; 13%). MS (m/z): 367 (M+H).

EXAMPLE 1

Synthesis of 3-{5-cyano-4-[-(2,2-dimethyl)(-propyl)-methyl-amino]-pyrimidin-2-ylamino}-4,N-dimethyl-benzamide

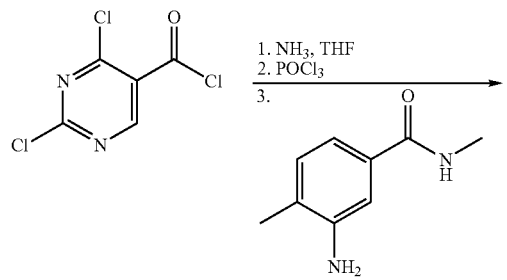

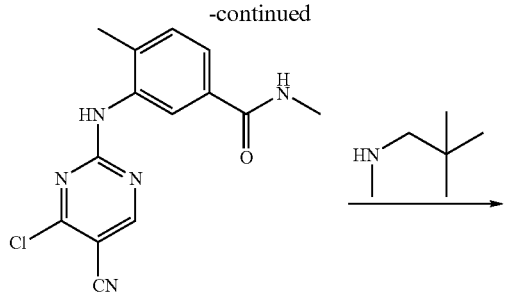

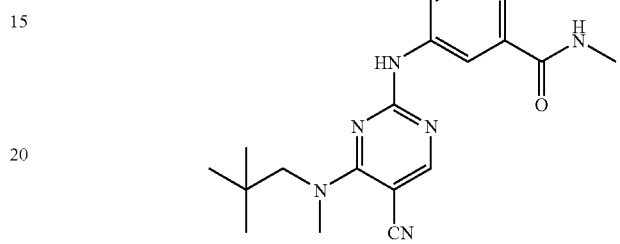

To a solution of 1.0 g of 2,4-dichloropyrimidine-5-carbonyl chloride (4.73 mmol) in 5 ml of THF at 0° C. is added dropwise a 0.5 M solution of NH₃ in 1,4-dioxane. The progress of the amide formation is followed via HPLC and the solution of NH₃ in 1,4-dioxane is added until all of the acid chloride is consumed. Then volatiles are removed in vacuo to yield a white solid.

To the crude product from above is added at r.t. 25 mL of POCl₃ and the resulting mixture is heated to 100° C. for 4 h. Volatiles are removed in vacuo, the crude product is absorbed on silica gel and washed off with 20% ethyl acetate in hexane to give a white solid.

To 20 mg of the product so obtained in 0.5 mL of THF is added at r.t. 0.022 mL of N,N-diisopropylethylamine 16.3 mg; 0.126 mmol) followed by 21 mg of 3-amino-4,N-dimethylbenzamide (0.126 mmol). The mixture is stirred at r.t. for 2 h, then 0.5 mL of THF are added followed by 32 mg of (2,2-dimethyl-propyl)-methyl-amine, hydrochloride (0.232 mmol) and 0.044 mL of N,N-diisopropylethylamine (32.6 mg; 0.252 mmol). The resulting mixture is heated at 60° C. for 18 h. Volatiles are removed in vacuo and the crude mixture containing two separable regioisomers is purified via reversed phase prep. HPLC. (Yield: 3.9 mg: 0.011 mmol; 8%). MS (m/z): 367 (M+H).

EXAMPLE 56

Synthesis of 3-{6-[(2,2-Dimethyl-propyl)-methyl-amino]-5-nitro-pyrimidin-4-ylamino}-4,N-dimethyl-benzamide

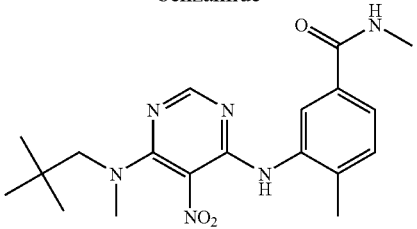

(a) (6-Chloro-5-nitro-pyrimidin-4-yl)-(2,2-dimethyl-propyl)-methyl-amine 4,6-Dichloro-5-nitro-pyrimidine (0.20 g, 1.0 mmol), N-methyl-neopentylamine hydrochloride (0.14 g) and DIEA (0.2 mL) were stirred in acetone (5 mL) at 0° C. for 4 hours. The solvent was removed in vacuo and the crude product was used for the next reaction without purification.

(b) Synthesis of 3-{6-[(2,2-Dimethyl-propyl)-methyl-amino]-5-nitro-pyrimidin-4-ylamino}-4,N-dimethyl-benzamide

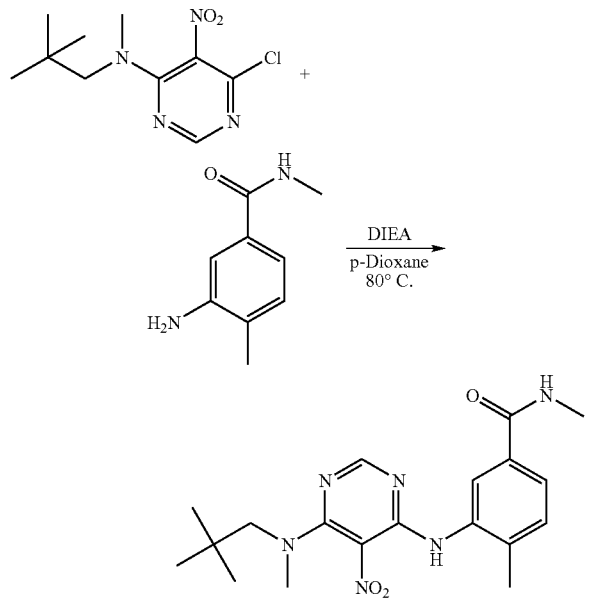

(6-Chloro-5-nitro-pyrimidin-4-yl)-(2,2-dimethyl-propyl)-methyl-amine (1.0 mmol) was dissolved in p-dioxane (2 mL), and 3-amino-4,N-dimethyl-benzamide (0.2 g, 1.2 mmol) and DIEA (0.3 mL) were added. The resulting mixture was heated to 80° C. for overnight. The product (0.31 g, yield 80%) was purified by column silica gel chromatography. MS (m/z): 387 (M+H).

EXAMPLE 26

Synthesis of N-(2,2-Dimethyl-propyl)-N-methyl-N'-[2-methyl-5-(4H-[1,2,4]triazol-3-yl)-phenyl]-5-nitro-pyrimidine-4,6-diamine

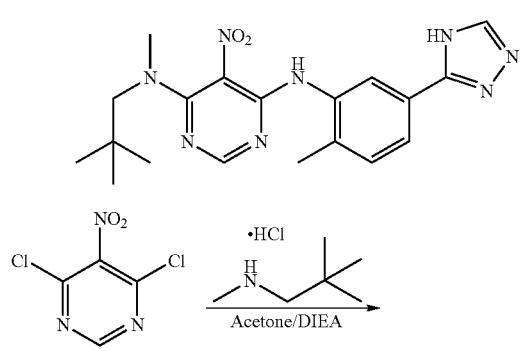

(a)

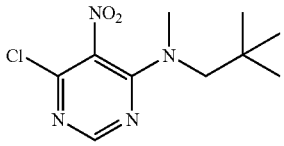

4,6-Dichloro-5-nitro-pyrimidine (193 mg, 1 mmol) was dissolved in 4 mL acetone at 0° C. To the solution was added N-(2,2-dimethylpropyl)methyl amine HCl salt (137 mg, 1 mmol) and diisopropylethylamine (0.17 mL, 1 mmol). The solution was stirred at 0° C. for 10 minutes, then room temperature for 3 hours, and evaporated in vacuo. The crude product was purified by flash chromatography to afford 180 mg of the product (Yield: 69%). MS (m/z) calcd for $C_{10}H_{15}ClN_4O_2$ (MH+), 259.1, found, 259.3.

(b)

A solution of (6-Chloro-5-nitro-pyrimidin-4-yl)-(2,2-dimethyl-propyl)-methyl-amine (185 mg, 0.72 mmol), diisopropylethylamine (0.13 mL, 0.72 mmol) and 2-Methyl-5-(4H-[1,2,4]triazol-3-yl)-phenylamine (126 mg, 0.72 mmol) in 3 mL of n-BuOH was heated with stirring at 80° C. for 18 h. The solvent was then evaporated in vacuo and the crude product was purified by flash chromatography to afford 87 mg of the product (30%). MS (m/z) calcd for $C_{19}H_{24}N_8O_2$ (MH+), 397.2, found, 397.3.

EXAMPLE 28

Synthesis of N-(2,2-Dimethyl-propyl)-N-methyl-N''-[2-methyl-5-(4H-[1,2,4]triazol-3-yl)phenyl]-pyrimidine-4,5,6-triamine

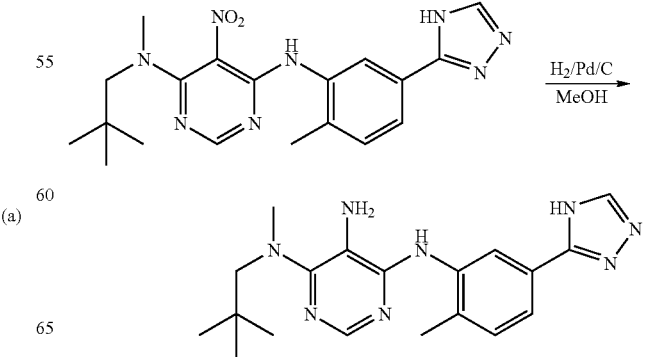

To a solution of N-(2,2-dimethyl-propyl)-N-methyl-N'-[2-methyl-5-(4H-[1,2,4]triazol-3-yl)phenyl]-5-nitro-pyrimidine-4,6-diamine (20 mg, 0.05 mmol) in 5 mL of methanol was added a catalytic amount of 10% Pd/C. The vessel was placed under a hydrogen atmosphere of 20 psi for 1 h at room temperature. The solution was filtered, and the filtrate was evaporated under vacuum to afford 4.6 mg of the product (Yield: 25%). MS (m/z) calcd for $C_{19}H_{26}N_8$ (MH+), 367.2, found, 367.4.

EXAMPLE 12

Synthesis of 3-{2-(3-Dimethylamino-propylamino)-6-[(2,2-dimethyl-propyl)-methyl-amino]-5-nitro-pyrimidin-4-ylamino}-4,N-dimethyl-benzamide

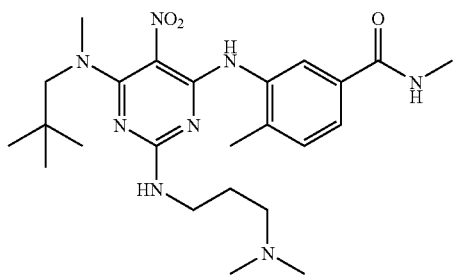

(a)

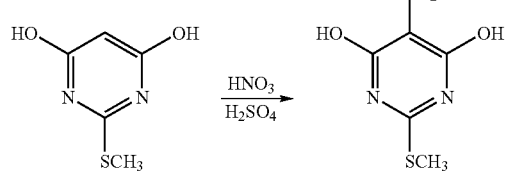

2-Methylsulfanyl-pyrimidine-4,6-diol (1.58 g, 10 mmol) was dissolved in 10 mL of con. $H_2SO_4$ at 0° C. To the solution was added 0.84 mL of nitric acid drop-wise. The solution was stirred at 0° C. for 30 minutes, then room temperature for 2 h. The solution was poured into ice water. The yellowish solid precipitated out of the solution was collected, washed with cold water and dried to afford 400 mg of the product (Yield: 20%).

(b)

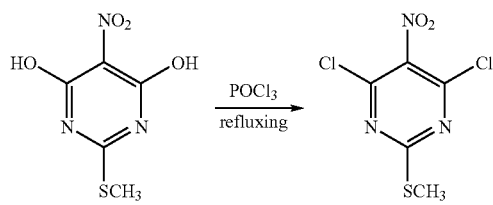

2-Methylsulfanyl-5-nitro-pyrimidine-4,6-diol (203 mg, 1 mmol) was dissolved in 4 mL of phosphorus oxychloride. The solution was refluxed at 120° C. for two hours. The solution was evaporated under vacuum. The oily residue was purified by flash chromatography to afford 80 mg of the product (Yield: 35%).

(c)

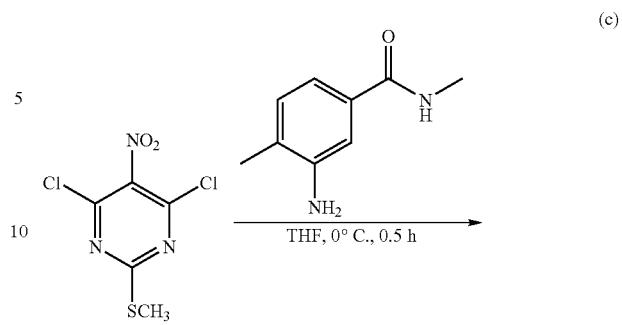

4,6-Dichloro-2-methylsulfanyl-5-nitro-pyrimidine (30 mg, 0.13 mmol) and 3-amino-4,N-dimethyl-benzamide (22 mg, 0.13 mmol) were dissolved in 2 mL of THF. The solution was stirred at 0° C. for 30 minutes, and evaporated under vacuum. The product thus obtained was directly used for the next reaction without purification.

(d)

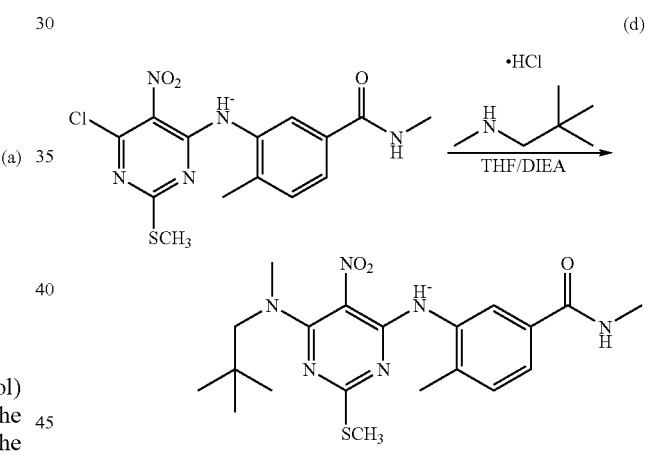

The intermediate so obtained was dissolved in 2 mL of THF. To the solution was added N-(2,2-dimethylpropyl) methyl amine HCl salt (36 mg, 0.26 mmol) and diisopropylethylamine (0.05 mL, 0.26 mmol). The solution was stirred at room temperature for 1 h, and evaporated under vacuum. The residue was purified by flash chromatography to afford 5.5 mg of the product (Yield: 10%, two steps). MS (m/z) calcd for $C_{20}H_{28}N_6O_3S$ (MH+), 433.2, found, 433.2.

(e)

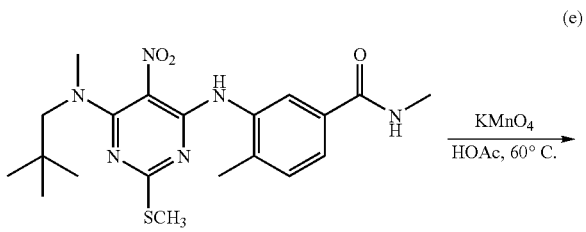

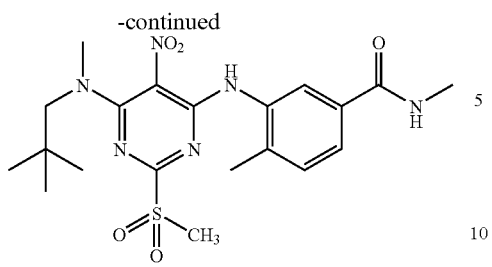

3-{6-[(2,2-dimethyl-propyl)-methyl-amino]-2-methylsulfanyl-5-nitro-pyrimidin-4-ylamino}-4,N-dimethyl-benzamide (24 mg, 0.06 mmol) was dissolved in 1 mL acetic acid. To the solution was added two drops of water and potassium permanganate (18 mg, 0.12 mmol). The solution was stirred at 60° C. for 10 minutes. The solution was diluted with water and extracted with ethyl acetate. The organic layer was washed with water, brine, dried over MgSO₄, and evaporated under vacuum. The residue was further purified by flash chromatography to afford 4.2 mg of the product (Yield: 15%). MS (m/z) calcd for $C_{20}H_{28}N_6O_5S$ (MH+), 465.2, found, 465.2.

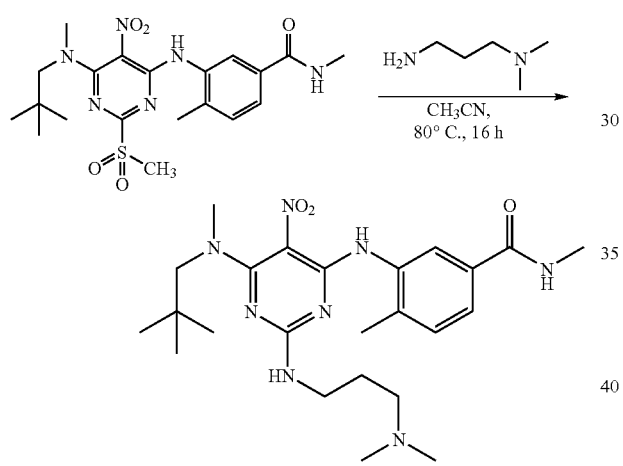

A solution of 3-{6-[(2,2-Dimethyl-propyl)-methylamino]-2-methanesulfonyl-5-nitro-pyrimidin-4-ylamino}-4,N-dimethyl-benzamide (4.2 mg, 0.01 mmol) and 3-(Dimethylamino)propylamine (0.2 mL) in 2 mL of acetonitrile was heated with stirring at 80° C. for 16 h. The solvent was then evaporated under vacuum and the crude product was purified by flash chromatography to afford 2.8 mg of the product (Yield: 64%). MS (m/z) calcd for $C_{24}H_{38}N_8O_3$ (MH+), 487.3, found, 487.3.

EXAMPLE 5

Synthesis of 3-[6-[(2,2-Dimethyl-propyl)-methyl-amino]-2-(1-methyl-piperidin-4-yloxy)-5-nitro-pyrimidin-4-ylamino]-4,N-dimethyl-benzamide

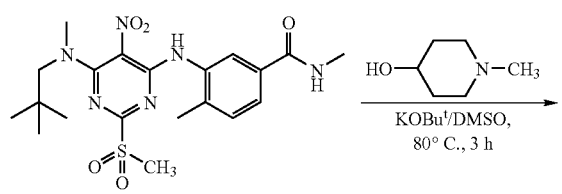

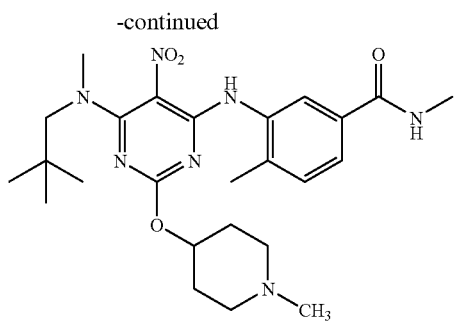

1-Methyl-piperidin-4-ol (56 mg, 0.5 mmol) was dissolved in 2 mL of DMSO. To the solution was added potassium tert-butoxide (56 mg, 0.5 mmol). The solution was stirred at room temperature for 1 h. The solution was then added to a solution of 3-{6-[(2,2-Dimethyl-propyl)-methyl-amino]-2-methanesulfonyl-5-nitro-pyrimidin-4-ylamino}-4,N-dimethyl-benzamide (4 mg, 0.01 mmol) in 0.5 mL of DMSO. The solution was stirred at 80° C. for 3 h, and extracted with ethyl acetate and water. The organic layer was washed with water, brine, dried over MgSO4, and evaporated under vacuum. The residue was purified by semi-preparative hplc column to afford 0.7 mg of the product (Yield: 16%). MS (m/z) calcd for $C_{25}H_{37}N_7O_4$ (MH+), 500.2, found, 500.1.

Although the present invention has been described in some detail by way of illustration and example, for purposes of clarity and understanding, it will be apparent that certain changes and modifications may be practiced within the scope of the appended claims.

What is claimed is:

1. A compound of Formula (I),

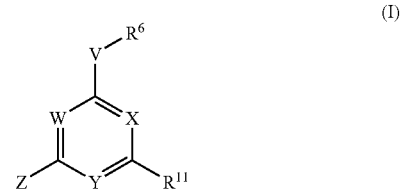

or enantiomers, diastereomers, tautomers, and pharmaceutically acceptable salts thereof, wherein:

Y and X are =N—;

is selected from =C—CN, =C—F, =C—Br, =C—NH₂, =C—NHC(O)CH₃ and =C—Cl;

V is —NR⁵—;

Z is halogen or —N(R¹)(R²);

R¹ and R² are the same or different and are selected from hydrogen, alkyl, substituted alkyl, cycloalkyl, substituted cycloalkyl, saturated heterocyclyl or substituted saturated heterocyclyl;

$R^5$ is hydrogen or alkyl;

$R^6$ is

[structure with $R^7$, $R^8$, $R^9$ substituents on phenyl ring]

$R^7$ is alkyl, substituted alkyl, alkoxy, or halogen;

$R^8$ is hydrogen, alkyl, alkyloxy or cyano;

$R^9$ is —C(O)$R^{10}$ or unsubstituted or substituted heterocyclyl;

$R^{10}$ is —N($R^{31}$)($R^{32}$);

$R^{31}$ and $R^{32}$ are the same or different and are selected from hydrogen, alkyl, substituted alkyl, alkoxy, aryl, substituted aryl, cycloalkyl, substituted cycloalkyl, heterocyclyl or substituted heterocyclyl; and $R^{11}$ is hydrogen or halogen.

2. A compound of claim 1, or enantiomers, diastereomers, tautomers, and pharmaceutically acceptable salts thereof, wherein:

V is —NH—;

Z is —N($R^1$)($R^2$);

$R^1$ and $R^2$ are the same or different and are selected from hydrogen, alkyl or substituted alkyl, wherein alkyl is of 1 to 8 carbons;

$R^7$ is alkyl of 1 to 4 carbons, alkoxy of 1 to 4 carbons, or halogen;

$R^8$ is hydrogen; and $R^{10}$ is —NH$_2$ or unsubstituted or substituted —NH-alkyl, —NH-alkoxy, —NH-heterocyclyl, —NH-phenyl, or —NH—CH$_2$-phenyl, wherein alkyl and alkoxy are of 1 to 6 carbons.

3. A compound of claim 2, or enantiomers, diastereomers, tautomers, and pharmaceutically acceptable salts thereof, wherein:

$R^1$ and $R^2$ are the same or different and are selected from hydrogen or alkyl of 1 to 8 carbons;

$R^7$ is methyl, methoxy, Cl, Br, or F; and $R^{10}$ is —NH$_2$, or unsubstituted or substituted —NH-alkyl, —NH-alkoxy, —NH-phenyl, or —NH—CH$_2$-phenyl, wherein alkyl and alkoxy are of 1 to 6 carbons; and $R^{11}$ is hydrogen or halogen.

4. A compound of claim 3, or enantiomers, diastereomers, tautomers, and pharmaceutically acceptable salts thereof, wherein:

$R^{10}$ is —NH$_2$, —NH—CH$_3$, —NH—C$_2$H$_5$, —NH—OCH$_3$, or —NH—OC$_2$H$_5$.

5. A compound of claim 3, or enantiomers, diastereomers, tautomers, and pharmaceutically acceptable salts thereof, wherein:

$R^9$ is unsubstituted or substituted triazole, thiazole, oxadiazole or imidazole.

6. A compound of claim 1, or enantiomers, diastereomers, tautomers, and pharmaceutically acceptable salts thereof, wherein said compound is selected from:

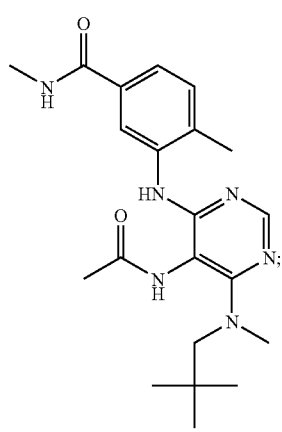

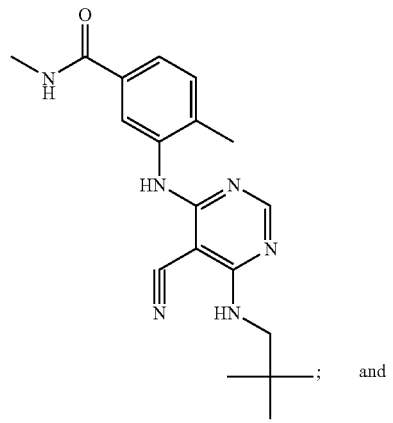

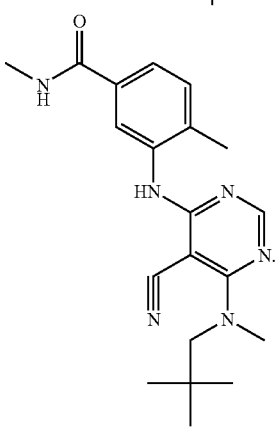

7. A pharmaceutical composition comprising, as an active ingredient, a compound, or a salt thereof, according to claim 1, and a pharmaceutically acceptable carrier.

8. A method of treating a TNF-α mediated disorder, comprising administering to a mammal in need of such treatment an effective amount of a composition according to claim 7, wherein the TNF-α mediated disorder is rheumatoid arthritis, psoriasis, Crohn's Disease, osteoarthritis or osteoporosis.

* * * * *

UNITED STATES PATENT AND TRADEMARK OFFICE
CERTIFICATE OF CORRECTION

PATENT NO. : 7,253,174 B2 Page 1 of 1
APPLICATION NO. : 11/485075
DATED : August 7, 2007
INVENTOR(S) : Ahmed Gulzar et al.

It is certified that error appears in the above-identified patent and that said Letters Patent is hereby corrected as shown below:

In the Claims:

Claim 1 Column 122 Line 59: insert --W-- before "is selected from"

Signed and Sealed this

Twenty-ninth Day of April, 2008

JON W. DUDAS
*Director of the United States Patent and Trademark Office*